US010000545B2

(12) United States Patent
Nassif et al.

(10) Patent No.: US 10,000,545 B2
(45) Date of Patent: Jun. 19, 2018

(54) **CD147 AS RECEPTOR FOR PILUS-MEDIATED ADHESION OF *MENINGOCOCCI* TO VASCULAR ENDOTHELIA**

(71) Applicants: INSTITUT NATIONAL DE LA SANTE ET DE LA RECHERCHE MEDICALE, Paris (FR); UNIVERSITE PARIS DESCARTES, Paris (FR)

(72) Inventors: Xavier Nassif, Paris (FR); Sandrine Bourdoulous, Paris (FR); Olivier Join-Lambert, Paris (FR)

(73) Assignees: INSTITUT NATIONAL DE LA SANTE ET DE LA RECHERCHE MEDICALE, Paris (FR); UNIVERSITE PARIS DESCARTES, Paris (FR)

( * ) Notice: Subject to any disclaimer, the term of this patent is extended or adjusted under 35 U.S.C. 154(b) by 0 days. days.

(21) Appl. No.: 14/405,444

(22) PCT Filed: Jul. 15, 2013

(86) PCT No.: PCT/EP2013/064900
§ 371 (c)(1),
(2) Date: Dec. 4, 2014

(87) PCT Pub. No.: WO2014/016152
PCT Pub. Date: Jan. 30, 2014

(65) Prior Publication Data
US 2015/0110806 A1 Apr. 23, 2015

(30) Foreign Application Priority Data
Jul. 27, 2012 (EP) .................... 12305920

(51) Int. Cl.
*A61K 39/095* (2006.01)
*C07K 14/705* (2006.01)
*C07K 14/22* (2006.01)
*C07K 16/28* (2006.01)
*A61K 39/395* (2006.01)
*A61K 39/40* (2006.01)
*C12N 15/113* (2010.01)
*G01N 33/50* (2006.01)
*A61K 39/00* (2006.01)

(52) U.S. Cl.
CPC ...... *C07K 14/70503* (2013.01); *A61K 39/095* (2013.01); *A61K 39/3955* (2013.01); *A61K 39/40* (2013.01); *C07K 14/22* (2013.01); *C07K 14/70596* (2013.01); *C07K 16/2803* (2013.01); *C12N 15/1138* (2013.01); *G01N 33/5041* (2013.01); *A61K 2039/505* (2013.01); *C07K 2317/76* (2013.01); *C07K 2319/30* (2013.01); *C07K 2319/32* (2013.01); *C12N 2310/11* (2013.01); *G01N 2333/195* (2013.01); *G01N 2333/70596* (2013.01); *G01N 2500/02* (2013.01); *G01N 2500/10* (2013.01)

(58) Field of Classification Search
CPC .... A61K 39/095; A61K 38/00; A61K 38/164; A61K 47/48246; A61K 47/48415; A61K 47/48561; A61K 2039/505; A61K 39/08; A61K 39/3955; A61K 39/40
USPC ................ 424/190.1, 164.1, 172.1; 530/350; 435/6.13, 7.21
See application file for complete search history.

(56) References Cited

U.S. PATENT DOCUMENTS

| | | | |
|---|---|---|---|
| 4,622,223 | A | 11/1986 | Schoolnik |
| 6,013,263 | A | 1/2000 | Barney |
| 6,017,536 | A | 1/2000 | Barney |
| 6,054,265 | A | 4/2000 | Barney |
| 6,060,065 | A | 5/2000 | Barney |
| 6,068,973 | A | 5/2000 | Barney |
| 6,093,794 | A | 7/2000 | Barney |
| 6,228,983 | B1 | 5/2001 | Barney |
| 6,333,395 | B1 | 12/2001 | Barney |
| 6,479,055 | B1 | 11/2002 | Bolggnesi |
| 6,518,013 | B1 | 2/2003 | Barney |
| 6,750,008 | B1 | 6/2004 | Trimeris |
| 6,824,783 | B1 | 11/2004 | Bolognesi |
| 6,951,717 | B1 | 5/2005 | Barney |

(Continued)

FOREIGN PATENT DOCUMENTS

| | | |
|---|---|---|
| EP | 0164920 | 9/2001 |
| EP | 1442047 | 6/2005 |

(Continued)

OTHER PUBLICATIONS

Proc Natl Acad Sci U S A. Dec. 18, 2001; 98(26): 15276-15281.*
U. Vogel, XVIIIth International Pathogenic Neisseria Conference (IPNC)abstracts.pdf Sep. 11, 2012.*
Trends in Microbiology, Sep. 2011, 19 (9) :456-463.*
International Search Report for PCT/EP2013/064900 dated Aug. 13, 2013.
Ana Cehovin et al: "Testing the vaccine potential of PilV, PilX and ComP, minor subunits of type IV pili", Vaccine, Elsevier Ltd, GB, vol. 29, No. 40, (Jul. 16, 2011) pp. 6858-6865.

(Continued)

*Primary Examiner* — Padmavathi Baskar
(74) *Attorney, Agent, or Firm* — B. Aaron Schuman, Esq.; Stites & Harbison, PLLC

(57) ABSTRACT

The present invention concerns the use of an inhibitor of an interaction between type IV pilus-associated protein and CD147 for preventing or treating meningoccal bacteraemia and/or infection. The present invention also relates to the combined use of such inhibitor and of an anti-bacterial compound, such as one used to prevent or treat a meningococcal infection. The invention also relates to a method for the prevention and/or treatment of meningococcal bacteraemia and/or infection, and to a method for screening inhibitors of the interaction between type IV pilus-associated protein and CD147.

5 Claims, 8 Drawing Sheets

(56) References Cited

U.S. PATENT DOCUMENTS

Figure 1:
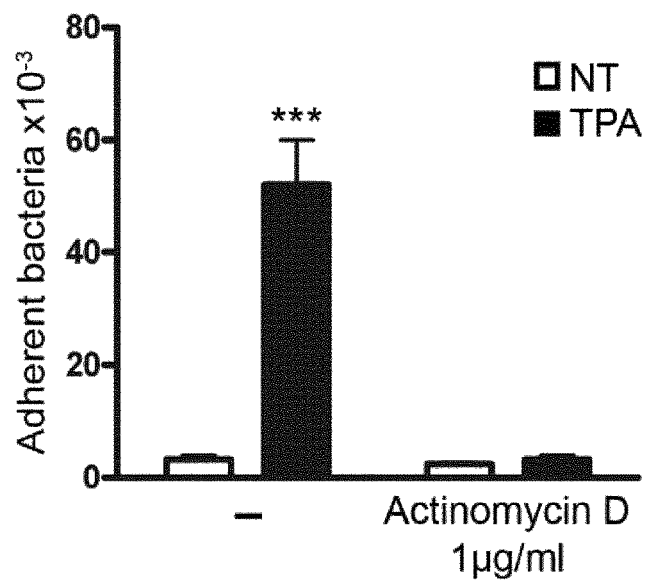

| | | |
|---|---|---|
| 6,994,860 B1 | 2/2006 | Ruelle et al. |
| 7,118,757 B1 | 10/2006 | Seid |
| 7,122,190 B2 | 10/2006 | Bolognesi |
| 7,238,345 B1 | 7/2007 | Seid |
| 7,244,411 B2 | 7/2007 | Nunez |
| 7,273,614 B2 | 9/2007 | Bolognesi |
| 7,368,261 B1 | 5/2008 | Rappuoli |
| 7,424,370 B2 | 9/2008 | Sachdeva |
| 7,504,111 B2 | 3/2009 | Fontana |
| 7,514,397 B1 | 4/2009 | Barney |
| 7,576,176 B1 | 8/2009 | Fraser |
| 7,604,810 B2 | 10/2009 | Rappuoli |
| 7,612,192 B2 | 11/2009 | Fraser |
| 7,655,245 B2 | 2/2010 | Scarlato |
| 7,785,608 B2 | 8/2010 | Zlotnick |
| 7,794,725 B1 | 9/2010 | Barney |
| 7,803,387 B2 | 9/2010 | Arico |
| 7,807,183 B2 | 10/2010 | Hong et al. |
| 7,838,015 B2 | 11/2010 | O'Hagan |
| 7,862,827 B2 | 1/2011 | Giuliani |
| 7,915,218 B2 | 3/2011 | Capecchi |
| 8,309,100 B2 | 11/2012 | Aujame et al. |
| 8,357,791 B2 | 1/2013 | Nassif |
| 8,547,536 B2 | 10/2013 | D'Ascenzi et al. |
| 8,574,597 B2 | 11/2013 | Zlotnick |
| 8,663,656 B2 | 3/2014 | Pizza |
| 8,895,577 B2 | 11/2014 | Wu et al. |
| 9,045,470 B2 | 6/2015 | Wu et al. |
| 9,180,204 B2 | 11/2015 | Contorni |
| 2003/0215469 A1 | 11/2003 | Robinson |
| 2004/0033235 A1 | 2/2004 | Bolognesi |
| 2004/0052820 A1 | 3/2004 | Bolognesi |
| 2004/0092711 A1 | 5/2004 | Arico |
| 2004/0167068 A1 | 8/2004 | Zlotnick |
| 2004/0265328 A1 | 12/2004 | Robinson et al. |
| 2005/0176085 A1 | 8/2005 | Nunez |
| 2005/0191316 A1 | 9/2005 | Fraser |
| 2005/0222385 A1 | 10/2005 | Pizza |
| 2005/0232936 A1 | 10/2005 | Arico |
| 2005/0244436 A1 | 11/2005 | Giuliani |
| 2005/0260581 A1 | 11/2005 | Fontana |
| 2005/0288866 A1 | 12/2005 | Sachdeva |
| 2006/0040264 A1 | 2/2006 | Nassif et al. |
| 2006/0051840 A1 | 3/2006 | Arico |
| 2006/0104974 A1* | 5/2006 | Davis ............ C07K 14/70596 424/144.1 |
| 2006/0166344 A1 | 7/2006 | Pizza |
| 2006/0171957 A1 | 8/2006 | Pizza |
| 2006/0251670 A1 | 11/2006 | Comanducci |
| 2006/0257413 A1 | 11/2006 | Zlotnick |
| 2006/0257852 A1 | 11/2006 | Rappuoli |
| 2007/0026021 A1 | 2/2007 | Fraser |
| 2007/0059329 A1 | 3/2007 | Norais et al. |
| 2007/0082006 A1 | 4/2007 | Zlotnick |
| 2007/0082007 A1 | 4/2007 | Zlotnick |
| 2007/0082014 A1 | 4/2007 | Costantino |
| 2007/0082866 A1 | 4/2007 | Zlotnick |
| 2007/0148729 A1 | 6/2007 | Farley |
| 2007/0202127 A1 | 8/2007 | Bolognesi |
| 2007/0219347 A1 | 9/2007 | Fraser |
| 2007/0224205 A1 | 9/2007 | Powell |
| 2007/0253982 A1 | 11/2007 | Song |
| 2007/0274994 A1 | 11/2007 | Masignani |
| 2008/0063657 A1 | 3/2008 | Powell |
| 2008/0131421 A1 | 6/2008 | Scarlato |
| 2008/0132448 A1 | 6/2008 | Rappuoli |
| 2008/0193971 A1 | 8/2008 | Serruto |
| 2008/0241180 A1 | 10/2008 | Costantino |
| 2008/0260769 A1 | 10/2008 | Capecchi |
| 2009/0148469 A1 | 6/2009 | Robinson |
| 2009/0162400 A1 | 6/2009 | Powell |
| 2009/0176699 A1 | 7/2009 | Masignani |
| 2009/0202593 A1 | 8/2009 | Zlotnick |
| 2009/0232820 A1 | 9/2009 | Fraser |
| 2009/0285845 A1 | 11/2009 | Masignani |
| 2009/0298099 A1 | 12/2009 | Fontana |
| 2010/0151151 A1 | 1/2010 | Rappuoli |
| 2010/0041868 A1 | 2/2010 | Rappuoli |
| 2010/0105875 A1 | 4/2010 | Scarselli |
| 2010/0143418 A1 | 6/2010 | Contorni |
| 2010/0150912 A1 | 6/2010 | Rappuoli |
| 2010/0189737 A1 | 7/2010 | Arico |
| 2010/0221256 A1 | 9/2010 | Arico |
| 2010/0233205 A1 | 9/2010 | Pizza |
| 2010/0267931 A1 | 10/2010 | Arico |
| 2010/0029168 A1 | 11/2010 | Trimeris |
| 2010/0285069 A1 | 11/2010 | Contorni |
| 2010/0303847 A1 | 12/2010 | Nakaar |
| 2011/0008279 A1 | 1/2011 | Masignani |
| 2011/0008383 A1 | 1/2011 | Powell |
| 2011/0020390 A1 | 1/2011 | Pizza |
| 2011/0033491 A1 | 2/2011 | Robinson |
| 2011/0052716 A1 | 3/2011 | Pallaoro |
| 2011/0053893 A1 | 3/2011 | Wu |
| 2011/0076299 A1 | 3/2011 | Zlotnick |
| 2011/0076300 A1 | 3/2011 | Pizza |
| 2011/0081365 A1 | 4/2011 | Cortez |
| 2011/0104193 A1 | 5/2011 | Giuliani |
| 2011/0250237 A1 | 10/2011 | O'Hagan et al. |
| 2011/0280949 A1 | 11/2011 | Malyala et al. |
| 2012/0064104 A1 | 3/2012 | Costantino |
| 2012/0070457 A1 | 3/2012 | Daugherty et al. |
| 2012/0237546 A1 | 9/2012 | Singh et al. |
| 2013/0287808 A1 | 10/2013 | Coureuil et al. |
| 2013/0331548 A1 | 12/2013 | Nakaar et al. |
| 2014/0037668 A1 | 2/2014 | Giuliani |
| 2015/0099859 A1 | 4/2015 | Song et al. |
| 2015/0110806 A1 | 4/2015 | Nassif |
| 2015/0118264 A1 | 4/2015 | Baumhof |
| 2016/0185827 A1 | 6/2016 | Coureuil et al. |
| 2016/0228529 A1 | 8/2016 | Contorni |
| 2016/0354457 A1 | 12/2016 | Costantino |

FOREIGN PATENT DOCUMENTS

| | | |
|---|---|---|
| EP | 1605061 | 12/2005 |
| EP | 1589341 | 4/2006 |
| EP | 1714974 | 10/2006 |
| EP | 1777233 | 4/2007 |
| EP | 1645631 | 10/2007 |
| EP | 1860191 | 11/2007 |
| EP | 1947187 | 7/2008 |
| EP | 1618185 | 5/2009 |
| EP | 2258390 | 12/2010 |
| EP | 2258851 | 12/2010 |
| EP | 2261239 | 12/2010 |
| EP | 2258717 | 1/2011 |
| EP | 2270031 | 1/2011 |
| EP | 2270172 | 1/2011 |
| EP | 2270173 | 1/2011 |
| EP | 2270174 | 1/2011 |
| EP | 2277538 | 1/2011 |
| EP | 2279746 | 2/2011 |
| EP | 2289546 | 3/2011 |
| EP | 1961426 | 4/2011 |
| EP | 2248822 | 4/2011 |
| EP | 2275552 | 8/2011 |
| EP | 2261340 | 1/2012 |
| EP | 2261353 | 1/2012 |
| EP | 2270030 | 5/2012 |
| EP | 2289545 | 5/2012 |
| EP | 1790660 | 6/2012 |
| EP | 1855715 | 3/2013 |
| EP | 2172213 | 4/2013 |
| EP | 2258389 | 6/2013 |
| EP | 2275129 | 11/2013 |
| EP | 2191844 | 3/2014 |
| EP | 1897555 | 7/2014 |
| EP | 2258716 | 7/2014 |
| EP | 2258388 | 8/2014 |
| EP | 2290083 | 8/2014 |
| EP | 1944371 | 3/2015 |
| EP | 2275553 | 5/2015 |
| WO | WO-99/55875 | 11/1999 |

(56) References Cited

FOREIGN PATENT DOCUMENTS

| WO | WO-99/57280 | 8/2000 |
|---|---|---|
| WO | WO-00/71725 | 11/2000 |
| WO | WO-0066791 | 11/2000 |
| WO | WO-01/64922 | 9/2001 |
| WO | WO-0022430 | 6/2002 |
| WO | WO-0066741 | 6/2002 |
| WO | WO-02/077648 | 10/2002 |
| WO | WO-02/079243 | 10/2002 |
| WO | WO-02/102843 | 12/2002 |
| WO | WO-03020756 | 3/2003 |
| WO | WO-03063766 | 8/2003 |
| WO | WO-03010194 | 10/2003 |
| WO | WO-2004/046177 | 6/2004 |
| WO | WO-2004/048404 | 6/2004 |
| WO | WO-2005032585 | 4/2005 |
| WO | WO-2004/092360 | 8/2005 |
| WO | WO-2005/076010 | 8/2005 |
| WO | WO-2004/113371 | 10/2005 |
| WO | WO-2005/106009 | 3/2006 |
| WO | WO-2006/024954 | 3/2006 |
| WO | WO-2006006074 | 4/2006 |
| WO | WO-2007/060548 | 5/2007 |
| WO | WO-2007103322 | 9/2007 |
| WO | WO-2007/066226 | 1/2008 |
| WO | WO-2008/001224 | 7/2008 |
| WO | WO 2008/125985 | 10/2008 |
| WO | WO-2009/104097 | 12/2009 |
| WO | WO-2009/128952 | 2/2010 |
| WO | WO-2010/028859 | 3/2010 |
| WO | WO-2009128949 | 3/2010 |
| WO | WO-2010030178 | 3/2010 |
| WO | WO-2009/114485 | 4/2010 |
| WO | WO-2010/0046715 | 4/2010 |
| WO | WO-2009144462 | 4/2010 |
| WO | WO-2010/109323 | 9/2010 |
| WO | WO-2010/109324 | 12/2010 |
| WO | WO-2010/144735 | 12/2010 |
| WO | WO-2011/024072 | 3/2011 |
| WO | WO-2011/027116 | 3/2011 |
| WO | WO-2011/051893 | 5/2011 |
| WO | WO-2011/039631 | 6/2011 |
| WO | WO-2009/128950 | 12/2013 |

OTHER PUBLICATIONS

S. Bernard, N. Simpson, C. Federici, M.-P. Laran-Chich, F. Chretien, 0. Join-Lambert, M. Coureuil, F. Nierdergang, et. al.: "XVIIIth International Pathogenic NeisseriaConference (IPNC) Sep. 9-14, 2012", Universitat Wurzburg, (Sep. 9, 2012), XP007921407, Retrieved from the Internet: URL:http://symposium.fmp-berlin.de/bbb2012 /prelprog.pdf [retrieved on Jan. 7, 2013].
Xavier Nassif, et al.; "How do extracellular pathogens cross the blood-brain barrier?" Trends in Microbiology, Elsevier Science Ltd. , vol. 10, No. 5; (May 2002), pp. 227-232.
Xavier Nassif, et al.; "Roles of pilin and PiIC in adhesion of Neisseria menengitidis to human epithelial and endothelial cells" Proc. Natl. Acad. Sci. USA, vol. 91, (Apr. 1994), pp. 3769-3773.
Hong-Chin Yan, et al.; "Human/Severe Combined Immunodeficient Mouse Chimeras" J. Clin. Invest., The American Society for Clinical Investigation, vol. 91 (Mar. 1993), pp. 986-996.
Guillain Mikaty, et al. Extracellular Bacterial Pathogen Induces Host Cell Surface Reorganization to Resist Shear Stress PLOS Pathogens, vol. 5, Iss. 2 (Feb. 2009) pp. 1-14.
Sophie Hélaine, et al., "PiIX, a pilus-associated protein essential for bacterial aggregation, is a key to pilus-facilitated attachment of Neisseria meningitides to human cells", Molecular Microbiology, Blackwell Publishing Ltd., vol. 55, No. 1 (2005) pp. 65-77.
Mélanie Lambotin, et al., "Invasion of endothelial cells by Neisseria meningitides requires cortactin recruitment by a phosphoinositide-3-kinase/Rac1 signalling pathway triggered by the lipo-oligosaccharide", Journal of Cell Science, vol. 118. No. 16 (May 26, 2005) pp. 3805-3816.
Emilie Mairey, et al., "Cerebral microcirculation shear stress levels determine Neisseria meningitidis attachment sites along the blood-brain barrier" Journal of Experimental Medicine, The Rockefeller University Press, vol. 203, No. 8 (Aug. 7, 2006) pp. 1939-1950.
Isabelle Hoffmann, et al., "Activation of ErbB2 receptor tyrosine kinase supports invasion of endothelial cells by Neisseria meningitides", Journal of Cell Biology, The Rockefeller University Press, vol. 155, No. 1 (Oct. 1, 2001) pp. 133-143.
Hervé Lécuyer, et al., "Two Strikingly Different Signaling Pathways Are Induced by Meningococcal Type IV Pili on Endothelial and Epithelial Cells" Infection and Immunity, Journals ASM.org, American Society for Microbiology (Oct. 25, 2011) pp. 175-186 Downloaded from http://iai.asm.org/ on Nov. 21, 2014 by SCD Universite Paris V.
Stephane Angers, et al., "Detection of b2-adrenergic receptor dimerization in living cells using bioluminescence resonance energy transfer (BRET)", PNAS, vol. 97, No. 7, (Mar. 28, 2000) pp. 3684-3689.
Nicolas Doulet, et al., "Neisseria meningitidis infection of human endothelial cells interferes with leukocyte transmigration by preventing the formation of endothelial docking structures", The Journal of Cell Biology, The Rockefeller University Press, vol. 173, No. 4, (May 22, 2006) pp. 627-637.
Jules Gilet, et al., "Role of CCL17 in the Generation of Cutaneous Inflammatory Reactions in Hu-PBMC-SCID Mice Grafted with Human Skin" Journal of Investigative Dermatology, The Society for Investigative Dermatology, vol. 129 (2009) pp. 879-890.
Jérôme Tourret, et al., "A Receptor for Meningococcus: Eliciting ß-Arrestin Signaling for Barrier Breaching", Developmental Cell 20, Elsevier Inc., (Jan. 28, 2011) pp. 7-8.
Winther-Larsen, et al., "Neisseria gonorrhoeae PilV, a type IV pilus-associated protein essential to human epithelial cell adherence", Dec. 18, 2011, pp. 15276-15281, vol. 98, No. 26, PNAS.

* cited by examiner

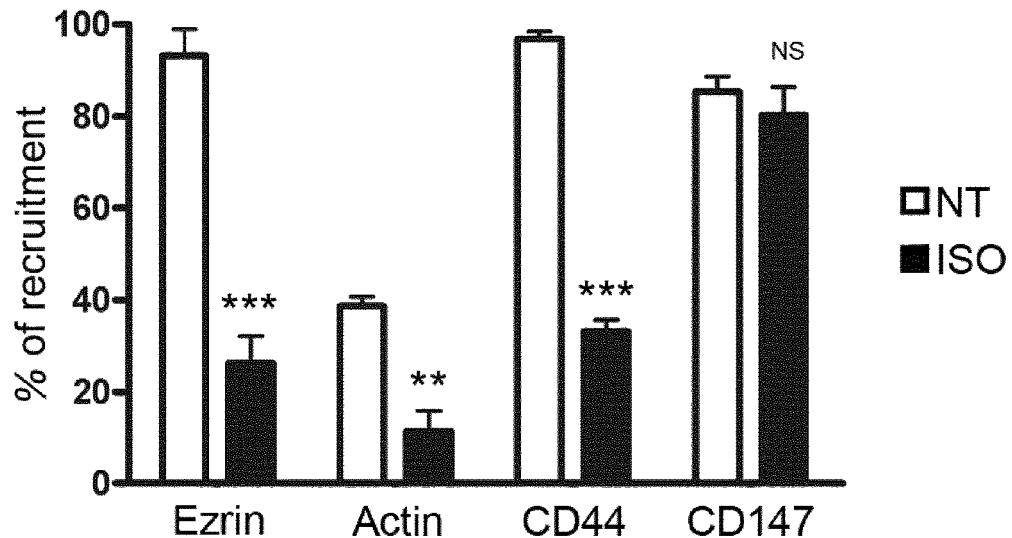
FIG.3
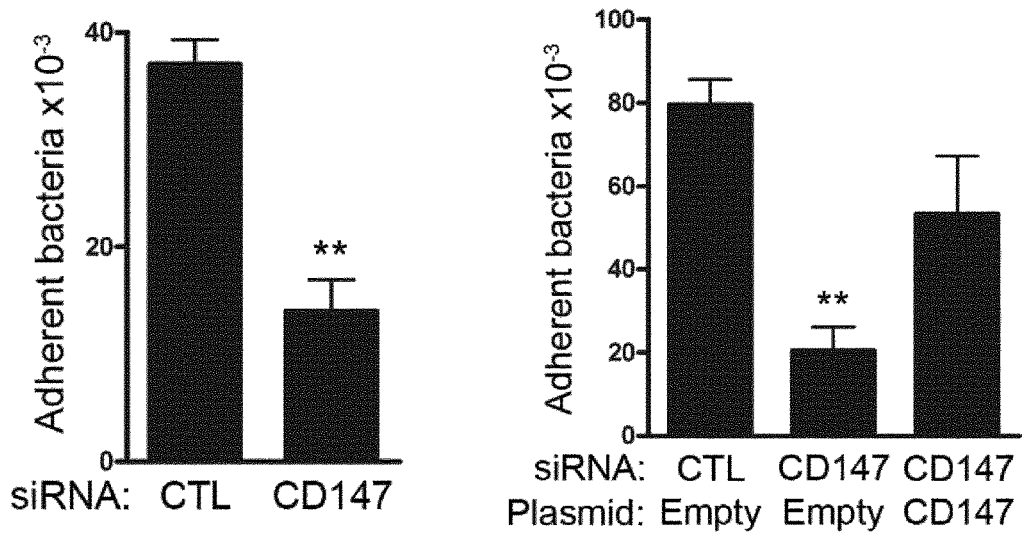
FIG.4
FIG.5

CD147 AS RECEPTOR FOR PILUS-MEDIATED ADHESION OF *MENINGOCOCCI* TO VASCULAR ENDOTHELIA

FIELD OF THE INVENTION

The present invention concerns the use of an inhibitor of an interaction between type IV pilus-associated protein and CD147 for preventing or treating meningococcal bacteraemia and/or infection. The present invention also relates to the combined use of such inhibitor and of an anti-bacterial compound, such as one used to prevent or treat a meningococcal infection. The invention also relates to a method for the prevention and/or treatment of meningococcal bacteraemia and/or infection, and to a method for screening inhibitors of the interaction between type IV pilus-associated protein and CD147.

BACKGROUND TO THE INVENTION

Meningococcus (*N. meningitidis*, Nm), a cause of epidemic meningitis and sepsis, is a commensal Gram-negative bacterium of the human nasopharynx. After bloodstream invasion, virulent encapsulated bacteria adhere to brain endothelial cells and proliferate onto the apical surface of host cells to form microcolonies at the site of initial bacterial attachment, then cross the Blood Brain Barrier (BBB) to colonize meninges (Nassif et al. 2002, Trends Microbiol, 10:227-232).

The main clinical feature of meningococcal infection is meningitis. Paradoxically, *Neisseria meningitidis* is a frequent asymptomatic colonizer of the human nasopharynx, and only a very small proportion of infections proceed to a sustained bacteraemia. In the majority of bacteremic patients the presence of *N. meningitidis* in the bloodstream will remain asymptomatic. However during the blood phase, the bacteria will interact with the brain endothelial cells and invade the meninges to be responsible for meningitis, which is the first clinical complication of meningococcal dissemination in 70% of patients. In 30% of bacteremic patients the presence of meningococci in the bloodstream will lead to clinical symptoms of septicemia with in some cases a *purpura fulminans*. In the latter case the bacteria cross the blood brain barrier; however, the meningitis symptoms are not at the forefront of the clinical presentation.

The emergence and epidemic potential of Nm are related to the expression of outer membrane components (capsular polysaccharide and lipooligosaccharide [endotoxin]), while the propensity of Nm to interact tightly with peripheral and brain vascular cells relies on the expression of type IV pili. These long filamentous structures, which extend from the bacterial cell surface, exhibit astonishing multifunctionality, including the attachment of virulent capsulated meningococci to cells and the triggering of host signalling events that contribute to the stabilization of bacterial colonies at the endothelial cell surface and promote subsequent translocation through endothelial barriers. Type IV pili are composed of hetero-multimeric pilin subunits, which are assembled into helical fibers by a complex machinery. They are comprised of the major pilin PilE required for piliation, and other low-abundance pilins (such as PilV, PilX or Comp) that structurally resemble PilE and modulate the pilus adhesive and signalling functions. The adhesive properties of type IV pili are also modulated by components of the pilus machinery such as the PilC1 allele, making it difficult to identify the molecular determinants involved in direct interaction with host cell receptors using a genetic approach. As a consequence, the precise adhesive components of the complex pilus structure remain undefined. However, it has been recently identified that the host G-protein-coupled β2-adrenergic receptor is an essential endothelial receptor for meningococcal type IV pili to trigger signalling events (Coureuil et al. 2010, Cell, 143:1149-1160; Lecuyer et al., 2011, Infect Immun, 80:175-186). Moreover, it has been identified that Nm colonies at the cell surface of a human brain endothelial cell line promote the translocation of Parrs to the inner surface of plasma membrane, facing bacteria. Parrs translocated under the colonies serve as a scaffolding platform for signaling events elicited by Nm. Among the GPCRs expressed in the cell line, only the β2-adrenoceptor (β2AR) plays a permissive role in the formation of cortical plaques under colonies and in bacterial crossing of cell monolayers. These observations reveal the requisition of a β2-adrenergic/β-arrestin signaling pathway by Nm to promote stable adhesion onto human brain endothelial cells and subsequent crossing of the BBB. More specifically, it has been shown that interaction of β2AR, in particular of the N-terminus of β2AR, with type IV pilus-associated proteins such as PilE or PilV, initiates the process allowing *N. meningitidis* to open and to traverse the BBB.

However, endothelial cells depleted of β2-adrenergic receptors still support bacterial adhesion, indicating that type IV pili promote the primary attachment of meningococci by interaction with another as yet unknown receptor.

Thus, preventing the primary attachment of meningococci to endothelial cells will prevent meningeal dissemination in the bloodstream, i.e. meningococcal bacteraemia, and/or meningococcal infection and, thereby will prevent bacterial meningitis and/or *purpura fulminans*.

SUMMARY OF THE INVENTION

The inventors have found that primary meningococcal adhesion to endothelial cells is mediated by the interaction between type IV pilus-associated proteins present at the surface of the meningococci and CD147 present at the surface of the host endothelial cells, and that such interaction can be blocked, thereby inhibiting meningococcal bacteraemia, and consequently meningococcal infection.

Thus, the invention relates to an inhibitor of an interaction between type IV pilus-associated proteins and CD147 for use for preventing or treating meningococcal bacteraemia and/or infection. Said inhibitor is preferably (i) a CD147 inhibitor and/or (ii) a type IV pilus-associated protein inhibitor. Preferably, said interaction is a direct interaction.

In an embodiment, said inhibitor comprises a CD147 inhibitor which is a polypeptide able to interact with the CD147 receptor and thereby inhibits interaction between type IV pilus-associated protein and CD147 receptor.

In an embodiment, this polypeptide is an anti-CD147 antibody or antibody fragment, preferably directed against an extracellular portion of CD147, and by this interaction, in particular binding, said antibody inhibits interaction between type IV pilus-associated protein and CD147 receptor or prevent or abolish attachment of the type IV pilus-associated protein to the CD147. In an embodiment, said anti-CD147 antibody is the MEM-M6/6 antibody.

In another embodiment, the polypeptide may be a type IV pilus-associated protein fragment which is able to bind to the CD147 receptor and compete with the bacteria, thereby inhibiting interaction between type IV pilus-associated protein and CD147 receptor or prevent or abolish attachment of the type IV pilus-associated protein to the CD147.

In another embodiment, said inhibitor comprises a CD147 inhibitor which is a nucleic acid, preferably a dsRNA which silences CD147 expression. Said CD147 inhibitor may comprise a siRNA or several siRNA silencing CD47 expression, preferably at least one siRNA of sequence SEQ ID NO: 1, 2, 3, 4 or 5.

In another embodiment, said inhibitor comprises a type IV pilus-associated protein inhibitor which is a polypeptide able to interact with the type IV pilus-associated protein and thereby inhibits interaction between type IV pilus-associated protein and CD147 receptor.

In an embodiment, this polypeptide is an anti-type IV pilus-associated protein antibody or antibody fragment, preferably directed against the binding site to the CD147 receptor, and by this interaction, in particular binding, said antibody inhibits interaction between type IV pilus-associated protein and CD147 receptor or prevents or abolishes attachment of the type IV pilus-associated protein to the CD147.

In another embodiment, this polypeptide is a CD147 polypeptide, preferably a polypeptide comprising CD147 amino acid sequence or a fragment thereof able to bind to a type IV pilus-associated protein, wherein said antibody or polypeptide inhibits interaction between type IV pilus-associated protein and CD147 receptor.

In an embodiment, said CD147 polypeptide comprises or consists of the soluble form of the extracellular domain of CD147, or a fragment thereof wherein said soluble form or fragment inhibits interaction between type IV pilus-associated protein and CD147 receptor. Said soluble form of the extracellular domain of CD147 may comprise or consist of the sequence SEQ ID NO: 6, or a fragment thereof.

Also provided is a pharmaceutical composition comprising an inhibitor of an interaction between type IV pilus-associated proteins and CD147 and a pharmaceutically acceptable vehicle, diluent or carrier.

Also provided is a pharmaceutical composition comprising an inhibitor of an interaction between type IV pilus-associated proteins and CD147 and additionally at least one anti-bacterial compound. Said composition comprises a pharmaceutically acceptable vehicle, diluent or carrier. According to a feature, the composition is for a simultaneous, separate or sequential administration to a mammal, including human. Preferably, said at least one anti-bacterial compound is (i) a meningococcal vaccine antigen, or (ii) a fusion protein comprising at least two meningococcal vaccine antigens. Said meningococcal vaccine antigen may comprise or consist of a meningococcal PilE, PilV, PilX, PilC, ComP, fHbp, PorA, NHBA, NadA, MafA, NspA, HmbR, TbpB, AusP, or a fragment thereof.

Further provided is the use of an inhibitor of an interaction between type IV pilus-associated proteins and CD147 in a method of preventing the adhesion of a meningococcus to endothelial cells. This method may be used in vivo or in vitro.

Also provided is a method for preventing or treating meningococcal bacteraemia and/or meningococcal infection comprising administering to an individual in need thereof (mammal, preferably human) a therapeutically effective amount of an inhibitor of an interaction between type IV pilus-associated proteins and CD147, or a composition as disclosed and provided herein.

Also provided is the use of an inhibitor of an interaction between type IV pilus-associated proteins and CD147 for the manufacture of a medicament for preventing or treating meningococcal bacteraemia and/or meningococcal infection.

Also provided is a method for screening inhibitors of the interaction between a type IV associated-pilus protein and the CD147 receptor, wherein said method comprises the step consisting of:
a) having a medium containing a type IV associated-pilus protein, or a fragment thereof, and CD147 receptor, or a fragment thereof, wherein said type IV associated-pilus protein, or a fragment thereof, and said CD147 receptor, or a fragment thereof, are able to specifically interact together to form a binding pair,
b) contacting said medium with a candidate compound,
c) measuring the inhibition of the interaction between said type IV associated-pilus protein, or a fragment thereof, and said CD147 receptor, or a fragment thereof.

DEFINITIONS

By "meningococcal bacteraemia" is meant the transient passage of a viable meningococcus in the blood of the host without any clinical symptoms.

By "meningococcal infection" it is meant the sustained presence of viable meningococcus in a host with clinical symptoms.

By "a meningococcus" is meant the *Neisseria meningitidis* (Nm) bacteria, preferably a Nm of serogroup A, B, C, Y or W135.

By "type IV pilus-associated protein", is meant a protein that is present at the surface of the pilus of a bacterium. For example, said type IV pilus-associated protein may be the PilE, the PilV, the PilX, the PilC, or the ComP protein. Preferably, said type IV pilus-associated protein is a PilE or PilV protein, and more preferably a PilE or PilV protein derived from any meningococcal serogroup, e.g. from a meningococcus of serogroup A, B, C, Y or W135.

By "CD147", also called Basigin (BSG) or extracellular matrix metalloproteinase inducer (EMMPRIN), is a member of the immunoglobulin superfamily that contains two heavily glycosylated C2 type immunoglobulin-like domains at the N-terminal extracellular portion. In some embodiments, the CD147 comprises or consists of:
a) the sequence SEQ ID NO: 7 (NCBI Reference Sequence NP_001719.2, update Feb. 26, 2012),
b) the sequence SEQ ID NO: 8 (NCBI Reference Sequence NP_940991.1, update Feb. 26, 2012),
c) the sequence encoded by the nucleic acid SEQ ID NO: 9 (NCBI Reference Sequence NM_001728.2, update Feb. 26, 2012),
d) the sequence encoded by the nucleic acid SEQ ID NO: 10 (NCBI Reference Sequence NM_198589.1, update Feb. 26, 2012),
e) a sequence at least 80, 85, 90, 95, 96, 97, 98, 99% identical to the sequence of a) to d).

By "interaction between type IV pilus-associated protein and CD147" is meant the direct interaction between type IV pilus-associated protein present at the surface of the meningococcus and CD147 present at the surface of the endothelial cells, such as peripheral or brain endothelial cells, of the host. In fact, the inventors have found that the direct interaction between type IV pilus-associated protein and CD147 allows the adhesion of meningococcus to the endothelial cells, thereby allowing the meningococcus to infect blood vessels, such as brain blood vessels and peripheral vessels.

By "inhibitor" is meant an agent that is able to reduce or to abolish the interaction between type IV pilus-associated protein and CD147. Said inhibitor may also be able to reduce or abolish the expression of CD147. According to the invention, said inhibitor is (i) a CD147 inhibitor and/or (ii) a type IV pilus-associated protein inhibitor.

Preferably, said inhibitor is able to reduce or to abolish the interaction between type IV pilus-associated protein and CD147, by at least 10, 20, 30, 40%, more preferably by at least 50, 60, 70%, and most preferably by at least 75, 80, 85, 90, 95, 96, 97, 98, 99, or 100%.

Reference herein to polypeptides and nucleic acid includes both the amino acid sequences and nucleic acid sequences disclosed herein and variants of said sequences. Variant proteins may be naturally occurring variants, such as splice variants, alleles and isoforms, or they may be produced by recombinant means. Variations in amino acid sequence may be introduced by substitution, deletion or insertion of one or more codons into the nucleic acid sequence encoding the protein that results in a change in the amino acid sequence of the protein. Optionally the variation is by substitution of 1, 2, 3, 4, 5, 6, 7, 8, 9, 10, 11, 12, 13, 14, 15, 16, 17, 18, 19, 20 or more amino acids with any other amino acid in the protein. Additionally or alternatively, the variation may be by addition or deletion of 1, 2, 3, 4, 5, 6, 7, 8, 9, 10, 11, 12, 13, 14, 15, 16, 17, 18, 19, 20 or more amino acids within the protein.

Variant nucleic acid sequences include sequences capable of specifically hybridizing to the sequence of SEQ ID Nos: 1-5, 9, 10 under moderate or high stringency conditions. Stringent conditions or high stringency conditions may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. Moderately stringent conditions may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C.

Fragments of the proteins and variant proteins disclosed herein are also encompassed by the invention. Such fragments may be truncated at the N-terminus or C-terminus, or may lack internal residues, for example, when compared with a full length protein. Preferably, said fragments are at least about 10, 20, 30, 40, 50, 60, 70, 80, 90, 100, 110, 120, 150, 250, 300, 350, 400, 450, 500 or more amino acids in length.

Fragments of the nucleic acid sequences and variants disclosed herein are also encompassed by the invention. Such fragments may be truncated at 3' or 5' end, or may lack internal bases, for example, when compared with a full length nucleic acid sequence. Preferably, said fragments are at least about 10, 20, 30, 40, 50, 60, 70, 80, 90, 100, 110, 120, 150, 250, 300, 350, 400, 450, 500 or more bases in length.

Variant proteins may include proteins encoded by the variant nucleic acid sequences as described hereabove. Variant proteins may also include proteins that have at least about 80% amino acid sequence identity with a polypeptide sequence disclosed herein. Preferably, a variant protein will have at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a full-length polypeptide sequence or a fragment of a polypeptide sequence as disclosed herein. Amino acid sequence identity is defined as the percentage of amino acid residues in the variant sequence that are identical with the amino acid residues in the reference sequence, after aligning the sequences and introducing gaps, if necessary, to achieve the maximum percent sequence identity, and not considering any conservative substitutions as part of the sequence identity. Sequence identity may be determined over the full length of the variant sequence, the full length of the reference sequence, or both.

Variant nucleic acid sequences may include nucleic acid sequences that have at least about 80% nucleotidic sequence identity with a nucleic acid sequence disclosed herein. Preferably, a variant nucleic acid sequences will have at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a full-length nucleic acid sequence or a fragment of a nucleic acid sequence as disclosed herein. Nucleic acid sequence identity is defined as the percentage of nucleic acids in the variant sequence that are identical with the nucleic acids in the reference sequence, after aligning the sequences and introducing gaps, if necessary, to achieve the maximum percent sequence identity, and not considering any conservative substitutions as part of the sequence identity. Sequence identity may be determined over the full length of the variant sequence, the full length of the reference sequence, or both.

A peptide "substantially homologous" to a reference peptide may derive from the reference sequence by one or more conservative substitutions. Preferably, these homologous peptides do not include two cysteine residues, so that cyclization is prevented. Two amino acid sequences are "substantially homologous" or "substantially similar" when one or more amino acid residue are replaced by a biologically similar residue or when greater than 80% of the amino acids are identical, or greater than about 90%, preferably greater than about 95%, are similar (functionally identical).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

In the context of the present application, the percentage of identity is calculated using a global alignment (i.e. the two sequences are compared over their entire length). Methods for comparing the identity of two or more sequences are well known in the art. The <<needle>> program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

Proteins consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the protein consisting of an amino acid sequence at least 80%, 85%, 90%, 95%, 96%, 97%, 98% or 99% identical to a reference sequence may correspond to a homologous sequence derived from another species than the reference sequence.

Amino acid substitutions may be conservative or non-conservative. Preferably, substitutions are conservative substitutions, in which one amino acid is substituted for another amino acid with similar structural and/or chemical properties. The substitution preferably corresponds to a conservative substitution as indicated in the table below.

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

The term "antibody" refers to immunoglobulin molecules and immunologically active portions of immunoglobulin molecules, i.e., molecules that contain an antigen binding site which immunospecifically binds an antigen. As such, the term antibody encompasses intact monoclonal antibodies, polyclonal antibodies, chimeric, humanized or human antibodies, antibodies, diabodies, multispecific antibodies (e.g. bispecific antibodies) formed from at least two intact antibodies, nanobodies, camelids antibodies, and also antibody fragments. In natural antibodies, two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non hypervariable or framework regions (FR) influence the overall domain structure and hence the combining site. Complementarity determining regions (CDRs) refer to amino acid sequences which, together, define the binding affinity and specificity of the natural Fv region of a native immunoglobulin binding-site. The light and heavy chains of an immunoglobulin each have three CDRs, designated L-CDR1, L-CDR2, L-CDR3 and H-CDR1, H-CDR2, H-CDR3, respectively. Therefore, an antigen-binding site includes six CDRs, comprising the CDR set from each of a heavy and a light chain V region.

Framework Regions (FRs) refer to amino acid sequences interposed between CDRs, i.e. to those portions of immunoglobulin light and heavy chain variable regions that are relatively conserved among different immunoglobulins in a single species, as defined by Kabat, et al (Sequences of Proteins of Immunological Interest (National Institutes of Health, Bethesda, Md., 1991). As used herein, a "human framework region" is a framework region that is substantially identical (about 85%, or more, in particular 90%, 95%, or 100%) to the framework region of a naturally occurring human antibody.

The term "monoclonal antibody" or "mAb" as used herein refers to an antibody molecule of a single amino acid composition, that is directed against a specific antigen and which may be produced by a single clone of B cells or hybridoma. Monoclonal antibodies may also be recombinant, i.e. produced by protein engineering.

The term "chimeric antibody" refers to an engineered antibody which comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens.

The term "humanized antibody" refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody".

"Antibody fragments" comprise a portion of an intact antibody, preferably the antigen binding or variable region of the intact antibody. Examples of antibody fragments include Fv, Fab, F(ab')2, Fab', dsFv, scFv, sc(Fv)2, diabodies and multispecific antibodies formed from antibody fragments.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')$_2$.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques. "dsFv" is a VH::VL heterodimer stabilised by a disulphide bond. Divalent and multivalent antibody fragments can form either spontaneously by association of monovalent scFvs, or can be generated by coupling monovalent scFvs by a peptide linker, such as divalent sc(Fv)$_2$.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "antisense nucleic acid", it is meant a non-enzymatic nucleic acid molecule that binds to target RNA by means of RNA-RNA or RNA-DNA or RNA-PNA (protein nucleic acid; Egholm et al., 1993, Nature 365, 566) interactions and alters the activity of the target RNA (for a review, see Stein and Cheng, 1993, Science 261, 1004, and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop or hairpin, and/or an antisense molecule can bind such that the antisense molecule forms a loop or hairpin. Thus, the antisense molecule can be complementary to 2, 3, 4, 5, 6, 7, 8, 9, 10 or more non-contiguous substrate sequences or 2, 3, 4, 5, 6, 7, 8, 9, 10 or more non-contiguous sequence portions of an antisense molecule can be complementary to a target sequence or both (for example, see Crooke, 2000, Methods Enzymol., 313, 3-45). In addition, antisense DNA can be used to target RNA by means of DNA-RNA interactions, thereby activating RNAse H, which digests the target RNA in the duplex. The antisense oligonucleotides can comprise one or more RNAse H activating region, which is capable of activating RNAse H cleavage of a target RNA.

Upon introduction, the antisense nucleic acid enters a cellular pathway that is commonly referred to as the RNA interference (RNAi) pathway. The term "RNA interference" or "RNAi" refers to selective intracellular degradation of RNA also referred to as gene silencing. RNAi also includes translational repression by small interfering RNAs (siRNAs). RNAi can be initiated by introduction of Long double-stranded RNA (dsRNAs) or siRNAs or production of siRNAs intracellularly, eg from a plasmid or transgene, to silence the expression of one or more target genes. Alternatively RNAi occurs in cells naturally to remove foreign RNAs, eg viral RNAs. Natural RNAi proceeds via dicer directed fragmentation of precursor dsRNA which direct the degradation mechanism to other cognate RNA sequences.

In some embodiments, the antisense nucleic acid may be Long double-stranded RNAs (dsRNAs), microRNA (miRNA) and/or small interferent RNA (siRNA).

As used herein "Long double-stranded RNA" or "dsRNA" refers to an oligoribonucleotide or polyribonucleotide, modified or unmodified, and fragments or portions thereof, of genomic or synthetic origin or derived from the expression of a vector, which may be partly or fully double stranded and which may be blunt ended or contain a 5' and or 3' overhang, and also may be of a hairpin form comprising a single oligoribonucleotide which folds back upon itself to give a double stranded region. In some embodiments, the dsRNA has a size ranging from 150 bp to 3000 bp, preferably ranging from 250 bp to 2000 bp, still more preferably ranging from 300 bp to 1000 bp. In some embodiments, said dsRNA has a size of at least 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, 900, 950, 1000, 1500 bp. In some embodiments, said dsRNA has a size of at most 3000, 2500, 2000, 1500, 1000, 950, 900, 850, 800, 750, 700, 650, 600, 550, 500, 450, 400, 350, 300 bp.

A "small interfering RNA" or "siRNA" is a RNA duplex of nucleotides that is targeted to a gene interest. A RNA duplex refers to the structure formed by the complementary pairing between two regions of a RNA molecule. siRNA is targeted to a gene in that the nucleotide sequence of the duplex portion of the siRNA is complementary to a nucleotide sequence of the targeted gene. In some embodiments, the length of the duplex of siRNAs is ranging from 15 nucleotides to 50 nucleotides, preferably ranging from 20 nucleotides to 35 nucleotides, still more preferably ranging from 21 nucleotides to 29 nucleotides. In some embodiments, the duplex can be of at least 15, 16, 17, 18, 19, 20, 21, 22, 23, 24, 25, 26, 27, 28, 29, 30, 31, 32, 33, 34, 35, 40, 45, 50 nucleotides in length. In some embodiments, the duplex can be of at most 45, 40, 35, 34, 33, 32, 31, 30, 29, 28, 27, 26, 25, 24, 23, 22, 21, 20, 19, 18, 17, 16, 15 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, or 13 nucleotides in length. The hairpin structure can also contain 3 or 5 overhang portions. In some embodiments, the overhang is a 3' or a 5' overhang 0, 1, 2, 3, 4, or 5 nucleotides in length.

Injection and transfection antisense nucleic acid into cells and organisms has been the main method of delivery. However, expression vectors may also be used to continually express antisense nucleic acid in transiently and stably transfected mammalian cells. (See for example, e.g., Brummelkamp et al., 2002, Science, 296:550-553; Paddison et al., 2002, Genes & Dev, 16:948-958).

Antisense nucleic acid may be synthesized chemically or expressed via the use of a single stranded DNA expression vector or equivalent thereof using protocols known in the art as described for example in Caruthers et al., 1992, Methods in Enzymology, 211:3-19; International PCT Publication No. WO 99/54459; Brennan et al., 1998, Biotechnol Bioeng, 61:33-45; and U.S. Pat. No. 6,001,311. In a non-limiting example, small scale syntheses are conducted on a 394 Applied Biosystems, Inc. synthesizer. Alternatively, the antisense nucleic acid molecules of the present invention can be synthesized separately and joined together post-synthetically, for example by ligation (International PCT publication No. WO 93/23569; Bellon et al., 1997, Bioconjugate Chem, 8:204).

The antisense nucleic acid of the invention may be able of decreasing the expression of CD147, by at least 10, 20, 30, 40%, more preferably by at least 50, 60, 70%, and most preferably by at least 75, 80, 85, 90, 95, 96, 97, 98, 99, 100%.

By "meningococcal vaccine antigen" is meant a meningococcal antigen that is capable of raising an immune response against *N. meningitidis*, and that is suitable for use as a vaccine or as an immunogenic compound.

By "immunogenic compound" is meant a compound that provokes or immunomodulates (i.e. immunosuppress or immunostimulate) an immune response when administered to an individual or which induces the production of antibodies when administered to an individual.

By "vaccine" as used herein refers to a compound, such as the immunogenic compound described herein which is administered to immunomodulate an immune response, that will protect or treat an individual from illness, in particular due to that agent. The vaccine may be a therapeutic (treatment) vaccine, i.e. for administration to the individual after development of the disease with the intention to reduce or arrest disease progression, and/or a preventive (prophylactic) vaccine, for administration to the individual prior to the development of the disease, with the intent to prevent initial (and/or recurrent) infection.

The terms "subject", "individual" or "host" are used interchangeably and may be, for example, a human or a non-human mammal. Preferably, the subject is a man, a woman, or a child.

Inhibitor of Interaction Between Type IV Pilus-Associated Protein and CD147

The present invention relates to an inhibitor of an interaction between type IV pilus-associated protein and CD147 receptor for use for preventing or treating a meningococcal bacteraemia and/or infection, wherein said inhibitor is:
(i) a CD147 inhibitor, and/or
(ii) a type IV pilus-associated protein inhibitor.

In some embodiments, the CD147 inhibitor is an anti-CD147 antibody or an antisense nucleic acid, wherein said antibody inhibits interaction between type IV pilus-associated protein and CD147 receptor, and said antisense nucleic acid silences CD147 receptor expression.

In one embodiment, said antisense nucleic acid may comprise or consist of a sequence that is able to inhibit or reduce the expression of a CD147 of sequence SEQ ID NO: 7 or 8, or a CD147 of sequence encoded by the nucleic acid SEQ ID NO: 9 or 10. Said antisense nucleic acid may comprise or consist of a sequence complementary to a nucleic acid encoding a CD147, for example a nucleic acid of sequence SEQ NO: 9 or 10. Preferably, said antisense nucleic acid comprises or consists of a siRNA, in particular at least one siRNA of sequence SEQ ID NO: 1, 2, 3, 4 or 5. In one embodiment, said siRNA comprises or consists of at least 2, 3, 4 or 5 siRNA selected from the group consisting of SEQ ID NOs: 1-5. In one embodiment, said siRNA comprises or consists of at most 5, 4, 3, or 2 siRNA selected from the group consisting of SEQ ID NOs: 1-5. In one embodiment, said siRNA comprises or consists of the four siRNA of sequence SEQ ID NO: 2, 3, 4 and 5.

Preferably, said anti-CD147 receptor antibody is able to prevent or inhibit the interaction between type-IV associated protein and CD147 receptor, thereby preventing or inhibiting the adhesion of meningococci to endothelial cells, and consequently preventing or inhibiting meningococcal bacteraemia and/or infection. Preferably, said anti-CD147 antibody is an antibody directed against the binding site of CD147 to type IV pilus-associated proteins. Preferably, said anti-CD147 antibody is directed against C-terminal domain of CD147 or to a fragment thereof. Still more preferably, said anti-CD147 antibody is directed to the ectodomain of CD147 or to a fragment thereof. Accordingly, said anti-CD147 is directed to the amino acids 16 to 321 of sequence SEQ ID NO: 7 or to a fragment thereof, or to the amino acids 16 to 205 of sequence SEQ ID NO: 8, or to a fragment thereof. Preferably, said anti-CD147 antibody is directed to a fragment of at least 10, 20, 30, 40, 50, 60, 70, 80, 90, 91, 92, 93, 94, 95, 96, 97, 98, 99, 100 contiguous amino acids of said ectodomain of CD147. Still preferably, said anti-CD147 is directed to a fragment consisting of the amino acid 221 to 315 of sequence SEQ ID NO:7 or to the amino acids 105 to 199 of sequence SEQ ID NO:8, i.e. to the membrane proximal Immunoglobulin domain of CD147 (Ig-like V type domain). Still preferably, said anti-CD147 antibody is the anti-CD147 antibody MEM-M6/6 (Abcam®).

In still another embodiment, the type IV pilus-associated protein inhibitor is an anti-type IV pilus-associated protein antibody. Preferably, said anti-type IV pilus-associated protein antibody is an antibody directed against the binding site of type IV pilus-associated protein to CD147 receptor, or to a fragment thereof. Still preferably, said anti-type IV pilus-associated protein antibody is an antibody directed to the binding site of PilE and/or PilV protein to CD147 receptor, or to a fragment thereof.

In still another embodiment, the type IV pilus-associated protein inhibitor is:
an immunogenic fragment of a type IV pilus-associated protein, or
a fusion protein comprising or consisting of at least 2, 3, 4, 5, 6, 7, 8, 9, 10 immunogenic fragments of a type IV pilus-associated protein, wherein said immunogenic fragment or said fusion protein is capable of raising an immune response with antibodies that prevent the interaction between said type IV pilus-associated protein and the CD147 receptor. Preferably, said immunogenic fragment is an immunogenic fragment of PilE or PilV. Consequently, said fusion protein may, for example, comprise or consist of (i) at least 2, 3, 4, 5, 6, 7, 8, 9, 10 immunogenic fragments of PilE, (ii) at least 2, 3, 4, 5, 6, 7, 8, 9, 10 immunogenic fragments of PilV, (iii) one immunogenic fragment of PilE and one immunogenic fragment of PilV, (iv) 2 immunogenic fragments of PilE and 2 immunogenic fragments of PilV, (v) one immunogenic fragment of PilE and 2 immunogenic fragments of PilV, etc.

In still another embodiment, the type IV pilus-associated protein inhibitor is a CD147 polypeptide. Preferably, said CD147 polypeptide is able to prevent or inhibit the interaction between said type-IV associated protein and said CD147 receptor, thereby preventing or inhibiting the adhesion of meningococci to endothelial cells, and consequently preventing or inhibiting meningococcal bacteraemia and/or infection. Accordingly, said CD147 polypeptide may be a CD147 amino acid sequence that (i) differs from a complete CD147 of sequence SEQ ID NO: 7 or 8, or from a complete CD147 of sequence encoded by the nucleic acid SEQ ID NO: 9 or 10, by one or several amino acid(s), and (ii) is not able to bind the endothelial cell membrane, or a fragment thereof.

In some embodiment, said CD147 polypeptide may comprise or consist of the extracellular domain of CD147, or a fragment thereof.

Preferably, said CD147 polypeptide comprises or consist of:
a) the amino acid sequence SEQ ID NO: 6, or
b) an amino acid sequence substantially homologous to SEQ ID NO:6, preferably at least 80, 85, 90, 95, 96, 97, 98, or 99% identical to SEQ ID NO:6.

For example, said fragment may comprise or consist of 10 to 180 contiguous amino acid of said CD147 polypeptide, preferably 50 to 150 amino acids, still preferably 80 to 120 amino acids. For example, said fragment may comprise or consist of at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180 contiguous amino acids of said CD147 polypeptide and/or at most 180, 175, 170, 165, 160, 155, 150, 145, 140, 135, 130, 125, 120, 115, 110, 105, 100, 95, 90, 85, 80, 75, 70, 65, 60, 55, 50, 45, 40, 35, 30, 25, 20, 15, 10 contiguous amino acids of said CD147 polypeptide.

Anti-Bacterial Compounds

In some embodiments, the inhibitor according to the invention is for administration in combination with at least one anti-bacterial compound, either sequentially or simultaneously.

In some embodiments, the inhibitor according to the invention is for administration in combination with at least 2, 3, 4, 5, 6, 7, 8, 9, 10 and/or at most 10, 9, 8, 7, 6, 5, 4, 3, 2 anti-bacterial compounds, either sequentially or simultaneously.

Sequential administration indicates that the components are administered at different times or time points, which may nonetheless be overlapping. Simultaneous administration indicates that the components are administered at the same time.

The anti-bacterial compound may be a biological compound and/or a chemical compound that inhibits or prevents development and/or multiplication of bacteria. Preferably, said anti-bacterial compound is an anti-bacterial compound effective against *Neisseria meningitidis* (Nm), preferably a Nm of serogroup A, B, C, Y or W135.

The anti-bacterial compound may include, but is not limited to, antibiotics, such as the beta-lactamines antibiotics. The beta-lactamines antibiotics may be for example, but without limitation, (a) penicillines, such as benzylpenicilline, phenoxyméthylpenicilline, méticilline, dicloxacilline, flucloxacilline, amoxicilline, ampicilline, co-amoxiclav, pipéracilline, ticarcilline, azlocilline, carbénicilline; (b) cephalosporin, such as cephalexin, cephalotin, cephazolin, cefaclor, cefuroxim, cefamandole, cefotetan, cefoxitin, ceftriaxone, cefixime, cefotaxime, ceftazidime, cefepime, cefpirome; (c) carbapenemes, such as imipeneme, meropeneme, ertapeneme, doripeneme, aztreonam, clanulanic acid, tazobactam, sulbactam.

Preferably, said at least one anti-bacterial compound is (i) a meningococcal vaccine antigen, or (ii) a fusion protein comprising at least two meningococcal vaccine antigens.

The meningococcal vaccine antigens according to the invention are well-known to the skilled in the art. Indeed, several vaccines against meningococci are commercialized and/or under development.

The meningococcal vaccine antigen may comprise or consist of at least one of the polysaccharide or glycoconjugate antigens comprised within the MCV-4 (commercialized under the name of MENACTRA® or MENVEO®), MPSV-4 (MENOMUNE®), MENCEVAX® or NmVac4-A/C/Y/W-135 vaccines.

The meningococcal vaccine antigen may also comprise or consists of the capsule of group B (MenB), A, C, Y, and/or W135 meningococci and/or to the outer membrane vesicle (OMV).

In some embodiments, the meningococcal vaccine antigen comprises or consists of a polypeptide or polypeptides. Several such polypeptides or polypeptidic antigens are currently investigated for their vaccinal potency. The meningococcal vaccine antigen may be any of the proteins of the external surface of the meningococci. Thus the meningococcal vaccine antigen may be for example, the PilE protein (e.g. as described in PCT/EP2011/069463), the PilV protein (e.g. as described in PCT/EP2011/069463), the PilX protein, the PilC protein, the ComP protein, Meningococcal Factor H binding protein (fHbp, previously referred to as GNA1870 or Lp2086), the major immunodominant surface porin (PorA), Neisserial Heparin Binding Antigen (NHBA, previously referred to as GNA2132), Neisseria adhesin A (NadA), MafA, Neisserial surface protein A (NspA), Hemoglobin Receptor (HmbR), Transferrin-binding Protein B (TbPB), Autotransporter serine Protease (AusP), or fragments thereof. Preferably, said fragments are immunogenic fragments.

The PilE protein may derive from any meningococcal serogroup, e.g. from a meningococcus of serogroup A, B, C, Y or W135. For example, said PilE protein may comprise or consist of the sequence of SEQ ID NO: 11 or SEQ ID NO: 12 or a sequence that is at least 80, 85, 90, 95 or 99% identical to the sequence SEQ ID NO: 11 or SEQ ID NO: 12, or an immunogenic fragment thereof.

The PilV protein may derive from any meningococcal serogroup, e.g. from a meningococcus of serogroup A, B, C, Y or W135. For example, said PilV protein may comprise or consist of the sequence of SEQ ID NO: 13 or a sequence that is at least 80, 85, 90, 95 or 99% identical to the sequence SEQ ID NO: 13, or an immunogenic fragment thereof.

The PilX protein may derive from any meningococcal serogroup, e.g. from a meningococcus of serogroup A, B, C, Y or W135. For example, said PilX protein may comprise or consist of the sequence of SEQ ID NO: 14 or a sequence that is at least 80, 85, 90, 95 or 99% identical to the sequence SEQ ID NO: 14, or an immunogenic fragment thereof.

The PilC protein may derive from any meningococcal serogroup, e.g. from a meningococcus of serogroup A, B, C, Y or W135. For example, said PilC protein may comprise or consist of the sequence of SEQ ID NO: 15 or a sequence that is at least 80, 85, 90, 95 or 99% identical to the sequence SEQ ID NO: 15, or an immunogenic fragment thereof.

The ComP protein may derive from any meningococcal serogroup, e.g. from a meningococcus of serogroup A, B, C, Y or W135. For example, said ComP protein may comprise or consist of the sequence of SEQ ID NO: 16 or a sequence that is at least 80, 85, 90, 95 or 99% identical to the sequence SEQ ID NO: 16, or an immunogenic fragment thereof.

The fHBP protein may be a fHBP polypeptide of subfamilyB/Variant1 or of subfamilyA/Variant 2. For example, said fHBP polypeptide may comprise or consist of the sequence SEQ ID NO: 17 or SEQ ID NO: 18 or a sequence at least 80, 85, 90, 95 or 99% identical to the sequence SEQ ID NO: 17 or SEQ ID NO: 18, or an immunogenic fragment thereof.

The PorA protein may derive from any meningococcal serogroup, e.g. from a meningococcus of serogroup A, B, C, Y or W135. For example, said PorA protein may comprise or consist of the sequence SEQ ID NO: 19 or a sequence at least 80, 85, 90, 95 or 99% identical to the sequence SEQ ID NO: 19, or an immunogenic fragment thereof.

The NHBA protein may derive from any meningococcal serogroup, e.g. from a meningococcus of serogroup A, B, C, Y or W135. For example, said NHBA protein may comprise or consist of the sequence SEQ ID NO: 20 or a sequence at least 80, 85, 90, 95 or 99% identical to the sequence SEQ ID NO: 20, or an immunogenic fragment thereof.

The NadA protein may derive from any meningococcal serogroup, e.g. from a meningococcus of serogroup A, B, C, Y or W135. For example, said NadA protein may comprise or consist of the sequence SEQ ID NO: 21 or a sequence at least 80, 85, 90, 95 or 99% identical to the sequence SEQ ID NO: 21, or an immunogenic fragment thereof.

The MafA protein may derive from any meningococcal serogroup, e.g. from a meningococcus of serogroup A, B, C, Y or W135. For example, said MafA protein may comprise or consist of the sequence of SEQ ID NO: 22, SEQ ID NO: 23, or SEQ ID NO: 24 or a sequence that is at least 80, 85, 90, 95 or 99% identical to the sequence SEQ ID NO: 22, SEQ ID NO: 23, or SEQ ID NO: 24, or an immunogenic fragment thereof.

The NspA protein may derive from any meningococcal serogroup, e.g. from a meningococcus of serogroup A, B, C, Y or W135. For example, said NspA protein may comprise or consist of the sequence of SEQ ID NO: 25 or a sequence that is at least 80, 85, 90, 95 or 99% identical to the sequence SEQ ID NO: 25, or an immunogenic fragment thereof.

The HmbR protein may derive from any meningococcal serogroup, e.g. from a meningococcus of serogroup A, B, C, Y or W135. For example, said HmbR protein may comprise or consist of the sequence of SEQ ID NO: 26 or a sequence that is at least 80, 85, 90, 95 or 99% identical to the sequence SEQ ID NO: 26, or an immunogenic fragment thereof.

The TbpB protein may derive from any meningococcal serogroup, e.g. from a meningococcus of serogroup A, B, C, Y or W135. For example, said TbpB protein may comprise or consist of the sequence of SEQ ID NO: 27 or a sequence that is at least 80, 85, 90, 95 or 99% identical to the sequence SEQ ID NO: 27, or an immunogenic fragment thereof.

The AusP protein may derive from any meningococcal serogroup, e.g. from a meningococcus of serogroup A, B, C, Y or W135. For example, said AusP protein may comprise or consist of the sequence of SEQ ID NO: 28 or a sequence that is at least 80, 85, 90, 95 or 99% identical to the sequence SEQ ID NO: 28, or an immunogenic fragment thereof.

The immunogenic fragments according to the invention may be a contiguous portion of a meningococcal vaccine antigen as described herein that has the same or substantially the same immunogenic activity as said meningococcal vaccine antigen. That is to say, the fragment is capable of raising an immune response with antibodies that recognizes PilE, PilV, PilX, PilC, ComP, fHBP, NadA, PorA, NHBA, MafA, NspA, HmbR, TbPB, or AusP. Preferably, the fragment is capable of raising an immune response with antibodies that prevent meningococcal infection. More preferably, said fragment is an immunogenic fragment of PilE or PilV that is capable of raising an immune response with antibodies that prevent meningococci to cross of the BBB or to spread into the meningeal space. Still more preferably, said fragment is an immunogenic fragment of PilE or PilV that is capable of raising an immune response with antibodies that inhibit the interaction between PilE and/or PilV and β2AR.

In some embodiment, said immunogenic fragment of PilE or PilV does not carry the hydrophobic domain of PilE or PilV, respectively. More particularly, said immunogenic fragment of PilE does not carry the hydrophobic domain of sequence FTLIELMIVIAIVGILAAVALPAYQDYTARAQVSEAILLAEGQKSAVTEYYL (SEQ ID NO: 29).

More particularly, said immunogenic fragment of PilV does not carry the hydrophobic domain of sequence FTLLELMIAVAILGILTLITYPSYKTYIRRVRLSEVRTTLLHNAQTMERYYRQ (SEQ ID NO: 30).

In some embodiments, said immunogenic fragment of PilE comprises or consists of:
a) the sequence SAVTEYYLNHGEWPGDNSSAGVATSADIKGKYVQSVTVANGVITAQMASSNVNNEIKSKKLS LWAKRQNGSVKWFCGQPVTRTTATATDVAAANGKTDDKINTKHLPSTCRDDSSAS (SEQ ID NO:31), or
b) a fragment of at least 10, 15, 20, 25, 30, 35, 40, 45, 50, 55, 60, 65, 70, 75, 80, 85, 90, 95, 100, 105, 110, 115 consecutives amino acids of the sequence SEQ ID NO:31, or
c) a sequence that is at least 80, 85, 90, 95 or 99% identical to the sequence of (a) or (b).

In some embodiments, said immunogenic fragment of PilV comprises or consists of:
a) the sequence TMERYYRQKGTFKTYDKNKLKQNKYFNVTLSKVSPDHFTLQADPNPTTNDGETCVVTLDGG TIAASGTNQSCPGFD (SEQ ID NO:32), or
b) a fragment of at least 10, 15, 20, 25, 30, 35, 40, 45, 50, 55, 60, 65, 70, 75 consecutives amino acids of the sequence SEQ ID NO:32, or
c) a sequence that is at least 80, 85, 90, 95 or 99% identical to the sequence of (a) or (b).

In some embodiments, said immunogenic fragment of PilE or PilV carries the recognition domain to the β2AR responsible for meningococcal signaling.

More particularly, said immunogenic fragment of PilE comprises or consists of:
a) the sequence CGQPVTRTTATATDVAAANGKTDDKINTKHLPSTC (SEQ ID NO: 33), or
b) a fragment of at least 10, 15, 20, 25, 30 consecutives amino acids of the sequence SEQ ID NO:33, or
c) a sequence that is at least 80, 85, 90, 95 or 99% identical to the sequence of (a) or (b).

More particularly, said immunogenic fragment of PilV comprises or consists of:
a) the sequence GETCVVTLNDGGTIAASGTNQSCPGFD (SEQ ID NO:34), or
b) a fragment of at least 10, 15, 20, 25 consecutives amino acids of the sequence SEQ ID NO:34, or
c) a sequence that is at least 80, 85, 90, 95 or 99% identical to the sequence of (a) or (b).

In some embodiments, said fusion protein comprises at least 2, 3, 4, 5, 6, 7, 8, 9, 10 or at most 10, 9, 8, 7, 6, 5, 4, 3, 2 meningococcal vaccine antigens as described herein.

For example, said fusion protein comprises or consists of:
a meningococcal PilE protein or an immunogenic fragment thereof, fused in frame with a meningococcal PilV protein or an immunogenic fragment thereof; or
a meningococcal PilE protein or an immunogenic fragment thereof, fused in frame with a PilX, PilC, ComP, fHBP, NadA, PorA, NHBA, MafA, NspA, HmbR, TbpB, or AusP protein or an immunogenic fragment thereof; or
a meningococcal PilV protein or an immunogenic fragment thereof, fused in frame with a PilX, PilC, ComP, fHBP, NadA, PorA, NHBA, MafA, NspA, HmbR, TbpB, or AusP protein or an immunogenic fragment thereof; or
a meningococcal PilE protein or an immunogenic fragment thereof, fused in frame with (i) a meningococcal PilV protein or an immunogenic fragment thereof, and (ii) a PilX, PilC, ComP, fHBP, NadA, PorA, NHBA, MafA, NspA, HmbR, TbpB, or AusP protein or an immunogenic fragment thereof.

For example, said fusion protein comprises or consists of the immunogenic fragment of PilE of sequence SEQ ID NO: 31 fused with the fHBP polypeptide of sequence SEQ ID NO: 18, or of the immunogenic fragment of PilE of sequence SEQ ID NO: 33 fused with the fHBP polypeptide of sequence SEQ ID NO: 18. Consequently, said fusion protein comprises or consists of the sequence SEQ ID NO: 35 or SEQ ID NO: 36.

For example, said fusion protein comprises or consists of the immunogenic fragment of PilV of sequence SEQ ID NO: 32 fused with the fHBP polypeptide of sequence SEQ ID NO: 18, or of the immunogenic fragment of PilV of sequence SEQ ID NO: 34 fused with the fHBP polypeptide of sequence SEQ ID NO: 18. Consequently said fusion protein comprises or consists of the sequence SEQ ID NO: 37 or SEQ ID NO: 38.

The fusion protein may further comprise other moieties such as e.g. peptidic linkers allowing linking the different antigens, proteins or fragments comprised within the fusion protein, a tag useful for purification, a leader sequence, a signal peptide, one or more peptidic fragments enhancing the immunogenicity, etc.

Pharmaceutical Compositions

The invention also relates to a pharmaceutical composition comprising an inhibitor according to the invention and a pharmaceutical acceptable vehicle, diluent, or carrier.

Preferably, said inhibitor comprises or consists of:
(i) at least 1, 2, 3, 4 or 5, or at most 5, 4, 3, 2, or 1 siRNA selected from the group consisting of siRNA of sequence SEQ ID NOs: 1, 2, 3, 4 and 5 as defined hereabove,
(ii) the 4 siRNA of sequence SEQ ID NOs: 2, 3, 4, and 5 as defined hereabove,
(iii) the anti-CD147 antibody MEM-M6/6 as defined hereabove, or
(iv) the variant CD147 of sequence SEQ ID NO: 6 as defined hereabove.

In some embodiments, said pharmaceutical composition further comprises at least one anti-bacterial compound. The active ingredients may be mixed in the same composition comprising a pharmaceutical acceptable vehicle, diluent, or carrier. They may be conditioned separately, for simultaneous, separate or sequential administration to a mammal, including human. Said pharmaceutical composition may also comprise at least 2, 3, 4, 5, 6, 7, 8, 9, 10 and/or at most 10, 9, 8, 7, 6, 5, 4, 3, 2 anti-bacterial compounds.

Said at least one anti-bacterial compound may be a compound as defined above. Preferably, said at least one anti-bacterial compound comprises or consists of:
(a) at least a PilE, PilV, PilX, PilC, ComP, fHBP, NadA, PorA, NHBA, MafA, NspA, HmbR, TbpB, or AusP protein or an immunogenic fragment thereof as defined hereabove, or
(b) a fusion protein as defined hereabove.

In some embodiments, said pharmaceutical composition comprises:
the inhibitor (i) and the anti-bacterial compound (a),
the inhibitor (ii) and the anti-bacterial compound (a),
the inhibitor (iii) and the anti-bacterial compound (a),
the inhibitor (iv) and the anti-bacterial compound (a),
the inhibitor (i) and the anti-bacterial compound (b),
the inhibitor (ii) and the anti-bacterial compound (b),
the inhibitor (iii) and the anti-bacterial compound (b),
the inhibitor (iv) and the anti-bacterial compound (b),
the inhibitors (i) and (iii), and the anti-bacterial compound (a),
the inhibitors (i) and (iv) and the anti-bacterial compound (a),
the inhibitors (i) and (iii), and the anti-bacterial compound (b),
the inhibitors (i) and (iv) and the anti-bacterial compound (b),
the inhibitors (ii) and (iii), and the anti-bacterial compound (a),
the inhibitors (ii) and (iv) and the anti-bacterial compound (a),
the inhibitors (ii) and (iii), and the anti-bacterial compound (b),
the inhibitors (ii) and (iv) and the anti-bacterial compound (b),
the inhibitors (i), (iii) and (iv), and the anti-bacterial compound (a),
the inhibitors (ii), (iii) and (iv), and the anti-bacterial compound (a),
the inhibitors (i), (iii) and (iv), and the anti-bacterial compound (b), or
the inhibitors (ii), (iii) and (iv), and the anti-bacterial compound (b).

The pharmaceutical compositions according to the invention may be administered orally in the form of a suitable pharmaceutical unit dosage form. The pharmaceutical compositions of the invention may be prepared in many forms that include tablets, hard or soft capsules, especially hard or soft gelatin capsules, aqueous solutions, suspensions, and liposomes and other slow-release formulations, such as shaped polymeric gels.

The mode of administration and dosage forms are closely related to the properties of the therapeutic agents or compositions which are desirable and efficacious for the given treatment application. Suitable dosage forms include, but are not limited to, oral, intravenous, rectal, sublingual, mucosal, nasal, ophthalmic, subcutaneous, intramuscular, transdermal, spinal, intrathecal, intra-articular, intra-arterial, subarachnoid, bronchial, and lymphatic administration, and other dosage forms for systemic delivery of active ingredients.

Pharmaceutical compositions of the invention may be administered by any method known in the art, including, without limitation, transdermal (passive via patch, gel, cream, ointment or iontophoretic); intravenous (bolus, infusion); subcutaneous (infusion, depot); transmucosal (buccal and sublingual, e.g., orodispersible tablets, wafers, film, and effervescent formulations; conjunctival (eye drops); rectal (suppository, enema)); or intradermal (bolus, infusion, depot).

The solid unit dosage forms can be of the conventional type. The solid form can be a capsule, such as an ordinary gelatin type containing the inhibitor of the present invention, and optionally an anti-bacterial compound of the present invention, and a carrier, for example, lubricants and inert fillers such as, lactose, sucrose, or cornstarch. In another embodiment, these compounds are tableted with conventional tablet bases such as lactose, sucrose, or corn starch in combination with binders like acacia, corn starch, or gelatin, disintegrating agents such as, corn starch, potato starch, or alginic acid, and a lubricant like stearic acid or magnesium stearate.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

Pharmaceutical compositions of the invention may also be formulated for parenteral administration (e.g., by injection, for example, bolus injection or continuous infusion) and may be presented in unit dosage form in ampoules, pre-filled syringes, small volume infusion containers or multi-dose containers with an added preservative. The pharmaceutical compositions may take such forms as suspensions, solutions, or emulsions in oily or aqueous vehicles, and may contain formulating agents such as suspending, stabilizing and/or dispersing agents. Alternatively, the pharmaceutical compositions of the invention may be in powder form, obtained by aseptic isolation of sterile solid or by lyophilization from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the pharmaceutical composition with the softened or melted carrier(s) followed by chilling and shaping in molds.

For administration by inhalation, the pharmaceutical compositions according to the invention are conveniently delivered from an insufflator, nebulizer or a pressurized pack or other convenient means of delivering an aerosol spray. Pressurized packs may comprise suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the pharmaceutical compositions of the invention may take the form of a dry powder composition, for example, a powder mix of the pharmaceutical composition and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the pharmaceutical compositions of the invention may be administered via a liquid spray, such as via a plastic bottle atomizer. Typical of these are the Mistometerg (isoproterenol inhaler-Wintrop) and the Medihaler® (isoproterenol inhaler-Riker).

For antisense nucleic acid administration, the pharmaceutical compositions of the invention may be prepared in forms that include encapsulation in liposomes, microparticles, microcapsules, lipid-based carrier systems. Non limiting examples of alternative lipid based carrier systems suitable for use in the present invention include polycationic polymer nucleic acid complexes (see, e.g. US Patent Publication No 20050222064), cyclodextrin polymer nucleic acid complexes (see, e.g. US Patent Publication No 20040087024), biodegradable poly 3 amino ester polymer nucleic acid complexes (see, e.g. US Patent Publication No 20040071654), pH sensitive liposomes (see, e.g. US Patent Publication No 20020192274), anionic liposomes (see, e.g. US Patent Publication No 20030026831), cationic liposomes (see, e.g. US Patent Publication No 20030229040), reversibly masked lipoplexes (see, e.g. US Patent Publication No 20030180950), cell type specific liposomes (see, e.g. US Patent Publication No 20030198664), microparticles containing polymeric matrices (see, e.g. US Patent Publication No 20040142475), pH sensitive lipoplexes (see, e.g. US Patent Publication No 20020192275), liposomes containing lipids derivatized with releasable hydrophilic polymers (see, e.g. US Patent Publication No 20030031704), lipid entrapped nucleic acid (see, e.g. PCT Patent Publication No WO 03/057190), lipid encapsulated nucleic acid (see, e.g. US Patent Publication No 20030129221), polycationic sterol derivative nucleic acid complexes (see, e.g. U.S. Pat. No. 6,756,054), other liposomal compositions (see, e.g. US Patent Publication No 20030035829), other microparticle compositions (see, e.g. US Patent Publication No 20030157030), poly-plexes (see, e.g. PCT Patent Publication No WO 03/066069), emulsion compositions (see, e.g. U.S. Pat. No. 6,747,014), condensed nucleic acid complexes (see, e.g. US Patent Publication No 20050123600), other polycationic nucleic acid complexes (see, e.g. US Patent Publication No 20030125281), polyvinylether nucleic acid complexes (see, e.g. US Patent Publication No 20040156909), polycyclic amidinium nucleic acid complexes (see, e.g. US Patent Publication No 20030220289), nanocapsule and microcapsule compositions (see, e.g. PCT Patent Publication No WO 02/096551), stabilized mixtures of liposomes and emulsions (see, e.g. EP1304160), porphyrin nucleic acid complexes (see, e.g. U.S. Pat. No. 6,620,805), lipid nucleic acid complexes (see, e.g. US Patent Publication No 20030203865), nucleic acid micro emulsions (see, e.g. US Patent Publication No 20050037086), and cationic lipid based compositions (see, e.g. US Patent Publication No 20050234232). One skilled in the art will appreciate that modified siRNA of the present invention can also be delivered as a naked siRNA molecule.

Pharmaceutical compositions of the invention may also contain other adjuvants such as flavorings, colorings, or preservatives.

It will be further appreciated that the amount of the pharmaceutical compositions required for use in treatment will vary not only with the therapeutic agent selected but also with the route of administration, the nature of the condition being treated and the age and condition of the patient and will be ultimately at the discretion of the attendant physician or clinician.

Method for Preventing Adhesion of Meningococci to an Endothelial Cell

The inhibitor according to the invention may be used in a method of preventing or inhibiting adhesion of meningococci to an endothelial cell.

Said method may be an in vitro or ex vivo method.

The invention thus provides the use of an inhibitor as defined herein in an in vitro or in vivo method for preventing or inhibiting adhesion of meningococci to an endothelial cell.

In some embodiments, said inhibitor is used in combination with at least one anti-bacterial compound as defined hereabove. In some embodiments, said inhibitor is used in combination with at least 2, 3, 4, 5, 6, 7, 8, 9, 10 and/or at most 10, 9, 8, 7, 6, 5, 4, 3, 2 anti-bacterial compounds as defined hereabove.

Said method may comprise, for example, exposing said cell and/or said meningococcus to said inhibitor. Where the method is an in vivo method, the method may comprise administering said inhibitor to a subject, preferably a patient in need thereof.

In some embodiments, said endothelial cells may be brain endothelial cells, capillaries endothelial cells, human dermal endothelial cells and/or umbilical vein endothelial cells.

Administration and Methods of Treatment

The invention also relates to a method for preventing or treating meningococcal bacteraemia or infection in an individual in need thereof comprising administering a therapeutically effective amount of an inhibitor according to the invention or a pharmaceutical composition of the invention.

By "treatment" is meant a therapeutic use (i.e. on a patient having a given disease) and by "preventing" is meant a prophylactic use (i.e. on an individual susceptible of developing a given disease). The term "treatment" not only includes treatment leading to complete cure of the disease, but also treatments slowing down the progression of the disease and/or prolonging the survival of the patient.

An "effective amount" refers to an amount effective, at dosages and for periods of time necessary, to achieve the desired therapeutic or prophylactic result.

A therapeutically effective amount of an inhibitor of the invention may vary according to factors such as the disease state, age, sex, and weight of the individual, and the ability of the protein, to elicit a desired therapeutic result. A therapeutically effective amount encompasses an amount in which any toxic or detrimental effects of the inhibitor are outweighed by the therapeutically beneficial effects. A therapeutically effective amount also encompasses an amount sufficient to confer benefit, e.g., clinical benefit.

In the context of the present invention, "preventing a meningococcal bacteraemia or infection" may mean prevention of meningococcus adhesion to the endothelial cells of the host.

In the context of the present invention, "treating a meningococcal bacteraemia or infection", may mean reversing, alleviating, or inhibiting meningococcus adhesion to the endothelial cells of the host.

In the context of the invention, meningococcal infection may be reduced by at least 30, 35, 40, 45, 50, 55, 60, 65, 70, 80, 85, 90, 91, 92, 93, 94, 95, 96, 97, 98, 99, 100%.

In some embodiments, the methods of the invention comprise the administration of an inhibitor as defined above, in combination with at least one anti-bacterial compound as defined above, either sequentially or simultaneously. For example, said at least other anti-bacterial compound is (i) a meningococcal vaccine antigen, or (ii) a fusion protein comprising at least two meningococcal vaccine antigens, as described hereabove.

In another embodiment, said method comprises the administration of a pharmaceutical composition according to the invention.

The administration regimen may be a systemic regimen. The mode of administration and dosage forms are closely related to the properties of the therapeutic agents or compositions which are desirable and efficacious for the given treatment application. Suitable dosage forms and routes of administration include, but are not limited to, oral, intravenous, rectal, sublingual, mucosal, nasal, ophthalmic, subcutaneous, intramuscular, transdermal, spinal, intrathecal, intra-articular, intra-arterial, sub-arachnoid, bronchial, and lymphatic administration, and/or other dosage forms and routes of administration for systemic delivery of active ingredients. In a preferred embodiment, the dosage forms are for parenteral administration.

The administration regimen may be for instance for a period of at least 5, 6, 7, 8, 9, 10, 15, 20, 25, 30, 35, 40, 45, 50, 55, 60, 65, 70, 75, 80, 85, 90, 95, 100 days.

The dose range may be between 0.1 mg/kg/day and 100 mg/kg/day. More preferably, the dose range is between 0.5 mg/kg/day and 100 mg/kg/day. Most preferably, the dose range is between 1 mg/kg/day and 80 mg/kg/day. Most preferably, the dose range is between 5 mg/kg/day and 50 mg/kg/day, or between 10 mg/kg/day and 40 mg/kg/day.

In some embodiments, the dose may be of at least 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50 mg/kg/day. In some embodiments, the dose may be of at most 50, 45, 40, 35, 30, 25, 20, 25, 15, 10, 5, 1, 0.5, 0.1 mg/kg/day.

The dose range may also be between 10 to 10000 UI/kg/day. More preferably, the dose range is between 50 to 5000 UI/kg/day, or between 100 to 1000 UI/kg/day.

In some embodiments, the dose may be of at least 10, 25, 50, 75, 100, 150, 200, 250, 300, 350, 400, 450, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000 UI/kg/day. In some embodiments, the dose may be of at most 10000, 9500, 9000, 8500, 8000, 7500, 7000, 6500, 6000, 5500, 5000, 4500, 4000, 3500, 3000, 2500, 2000, 1500, 1000, 900, 800, 600, 500, 450, 400, 350, 300, 250, 200, 150, 100 UI/kg/day.

Screening Method

The invention also relates to a method for screening inhibitors of the interaction between a type IV associated-pilus protein and the CD147 receptor, wherein said method comprises the step consisting of:
a) having a medium containing a type IV associated-pilus protein, or a fragment thereof, and CD147 receptor, or a fragment thereof, wherein said type IV associated-pilus protein, or a fragment thereof, and said CD147 receptor, or a fragment thereof, are able to specifically interact together to form a binding pair,
b) contacting said medium with a candidate compound,
c) measuring the inhibition of the interaction between said type IV associated-pilus protein, or a fragment thereof, and said CD147 receptor, or a fragment thereof.

Preferably, step b) is performed by adding the candidate compound to the medium of step a).

Compounds that inhibits the interaction are selected. This selection may be performed if the measuring in step c) demonstrates a significant inhibition of said interaction.

In some embodiments, said type IV associated-pilus protein comprises or consists of a PilE or PilV protein or to a fragment thereof that is able to interact with CD147 receptor.

In some embodiments, said fragment of CD147 receptor comprises or consists of the ectodomain of CD147 or to the membrane proximal Immunoglobulin domain of CD147, or to the extracellular domain of CD147 of sequence SEQ ID NO: 6.

In some embodiments, the method according to the present invention is characterized in that at step c) the measure of the inhibition of the interaction is carried out by immunoassay (particularly by ELISA or by Immunoradiometric Assay (IRMA)), by Scintillation Proximity Assay (SPA) or by Fluorescence Resonance Energy Transfer (FRET).

Preferably, the method according to the present invention method is based on the ALPHASCREEN® technology. ALPHASCREEN® is based on Donor (D, photosensitizer) and Acceptor (A, chemiluminescer) microbeads, coated with two molecules of interest, susceptible of binding to each other. Laser excitation of the D beads causes ambient oxygen to be converted to the singlet state by the photosensitizer. Singlet oxygen species in turn activate chemiluminescent agents on the A beads. Upon activation, the chemiluminescent agent emits light which is detected by the photodetector in a microplate reader. A signal is produced when the A and D beads are brought into proximity (<200 nm) thus reporting for the interaction between the partners captured on the two beads (Taouji et al., 2009, Curr Genomics, 10(2):93).

Accordingly, in an embodiment, at step a) said type IV associated-pilus protein, or fragment thereof, is bound to an acceptor bead and said CD147 receptor, or fragment thereof, is bound to a donor bead. In another embodiment, at step a) said type IV associated-pilus protein, or fragment thereof, is bound to a donor bead and said CD147 receptor, or fragment thereof, is bound to an acceptor bead. Said type IV associated-pilus protein, or fragment thereof, and CD147, or fragment thereof, may be directly or indirectly bound to said beads.

Step a) is performed in conditions that allow the interaction between said type IV associated-pilus protein and said CD147 receptor. Accordingly, the binding of said type IV associated-pilus protein and said CD147 receptor will result in bringing the donor and acceptor particle at a distance less than 200 nm from each other, thereby providing an energy transfer between the donor and acceptor molecules.

In some embodiments, the donor bead contains phtalocyanine and the acceptor bead contains rubren. The donor bead is submitted to a laser excitation at 680 nm, inducing the conversion of ambient oxygen to a singlet state oxygen. The singlet state oxygen reacts with the chemiluminescent agent, i.e. rubren, on the acceptor bead. Upon energy transfer, activated rubrene emits light at 520-620 which is detected by the photodetector in a microplate reader. The luminescence can for example be measured with a photodetector in a microwell plate reader, such as the ENVISION® multilabel plate reader from Perkin-Elmer.

In some embodiments, the donor and acceptor beads are bound to fluorophores and the energy transfer amounts to fluorescence is emitted upon excitation by a first donor fluorophore, towards a second acceptor fluorophore. The acceptor fluorophore is, thus, activated and emits a second fluorescence. The fluorescence of the second acceptor fluorophore can be measured for example by a spectrofluorometer.

If energy transfer is detected at step a), it is considered that there is an interaction between said type IV associated-pilus protein, or fragment thereof, and said CD147 receptor, or fragment thereof.

The candidate compounds include but are not limited to peptides, small molecules, antibodies, aptamers and nucleic acids such as antisense nucleic acids.

Measuring the inhibition of interaction between said type IV pilus-associated protein, or fragment thereof, and said CD147 receptor, or fragment thereof, at step c) may be performed by measuring the luminescence or the fluorescence. If the level of luminescence or fluorescence at step c) is lower than the level of luminescence or fluorescence at step a), it indicates that the candidate compound is an inhibitor of the interaction of said type IV associated-pilus protein, or fragment thereof, and said CD147 receptor, or fragment thereof.

The invention will now be described in more detail with reference to the following figures and examples. All literature and patent documents cited herein are hereby incorporated by reference.

FIGURES

FIG. 1. Identification of CD147 as $N.$ $meningitidis$ receptor candidate. TPA treatment induces Nm adhesion to BB19 cells: cells were untreated (white) or treated with TPA (10 ng/ml, black) in the absence (−) or in the presence of Actinomycin D (1 µg/ml). Adhesion of wild type meningococci (WT) was measured 48 h after treatment. Mean±s.e.m, n>_3; ***P<0.0001; Two-way Anova.

Figure 2:
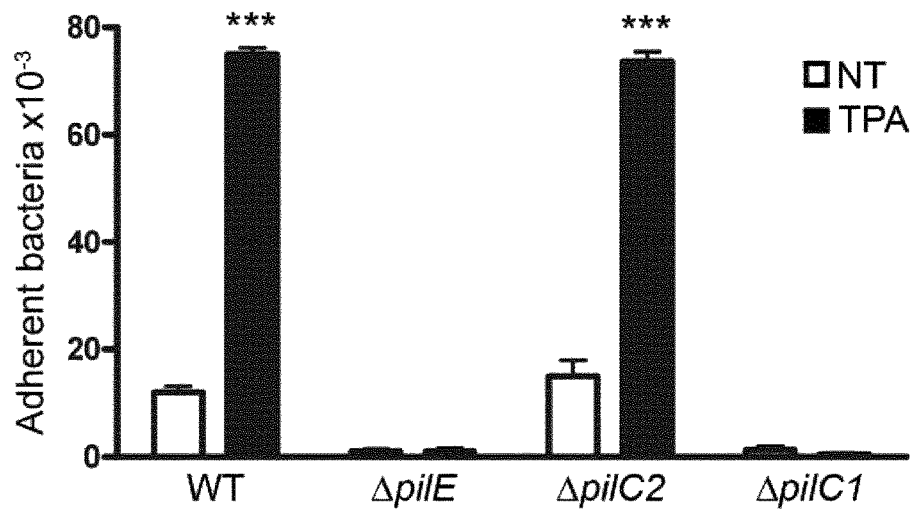

FIG. 2. Identification of CD147 as $N.$ $meningitidis$ receptor candidate. TPA treatment induces Nm adhesion to BB19 cells: cells were untreated (white) or treated with TPA (10 ng/ml, black). Adhesion of wild type meningococci (WT) or of the bacterial mutants dpilE, dpilC1 or dpilC2 was measured 48 h after treatment. Mean±s.e.m, n>_3; ***P<0.0001; Two-way Anova.

FIG. 3. CD147 accumulates at sites of bacterial adhesion independently of the 02-adrenergic receptor-coupled signalling events. Isoproterenol-induced β2-adrenergic receptor endocytosis inhibited type IV pilus-induced signaling events, but did not affect CD147 accumulation at sites of bacterial adhesion. Quantification of Ezrin, Actin, CD44 or CD147 recruitment at sites of Nm adhesion upon cell pretreatement with 10 laM isoproterenol. Mean±s.e.m, n=3; *P<0.001; P<0.01; NS P>0.05; Two-way Anova.

FIG. 4. CD147 knockdown reduced Nm adhesion to hCMEC/D3s relative to control siRNA (CTL). Mean±s.e.m, n=4; **P<0.05; Two-tailed t test.

FIG. 5. Expression of exogenous CD147 restored bacterial adhesion to CD147 knockdown hBMEC cells. Mean±s.e.m, n=3; **P=0.0025; One-way Anova.

Figure 6:
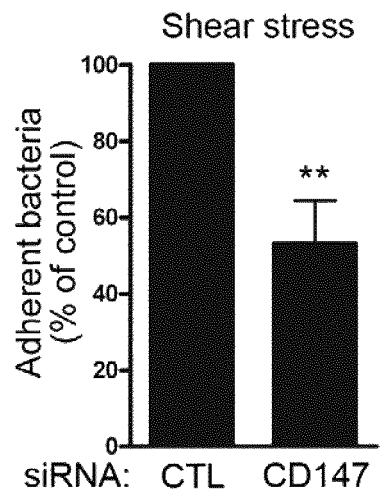

FIG. 6. CD147 knockdown reduced the initial attachment of Nm to hBMEC cells under shear stress. Mean±s.e.m, n=3; **P<0.01. One-way Anova.

Figure 7:
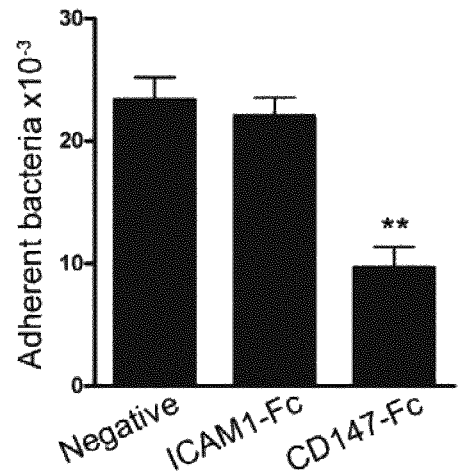

FIG. 7. CD147-Fc but not ICAM-1-Fc (both 5 µg/ml) reduced Nm adhesion to hBMEC cells. Mean±s.e.m, n=3; **P<0.01; One-way Anova.

Figure 8:
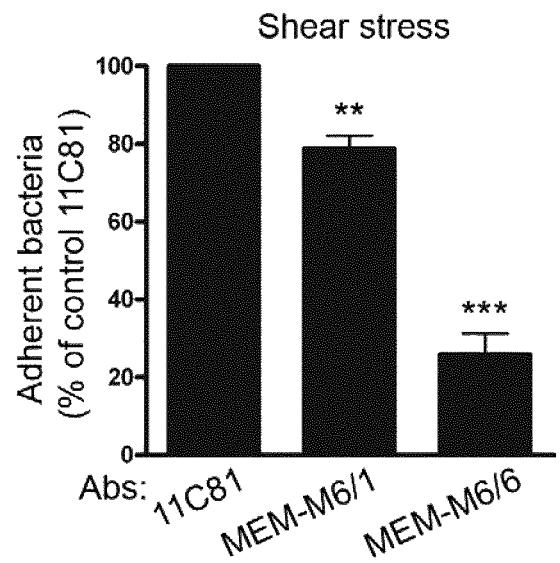

FIG. 8. AntiCD147 MEM-M6/6 [10 µg/ml] potently inhibited Nm adhesion to hBMEC cells, other antibodies [10 µg/ml] scarcely (MEM-M6/1) or did not (anti-ICAM-1, 11C81) affect adhesion. Mean±s.e.m, n=3; *P<0.001; P<0.001; One-way Anova.

Figure 9:
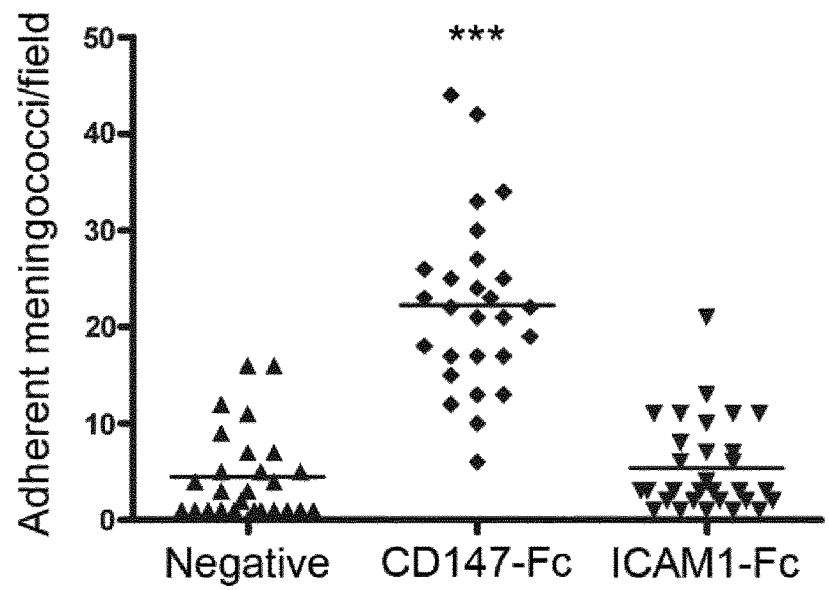

FIG. 9. Nm directly adhere on immobilised CD147-Fc, but not ICAM-1-Fc. Negative: no immobilised proteins. Bar: mean per field. Mean±s.e.m, n=3; ***P<0.001; One-way Anova.

Figure 10:
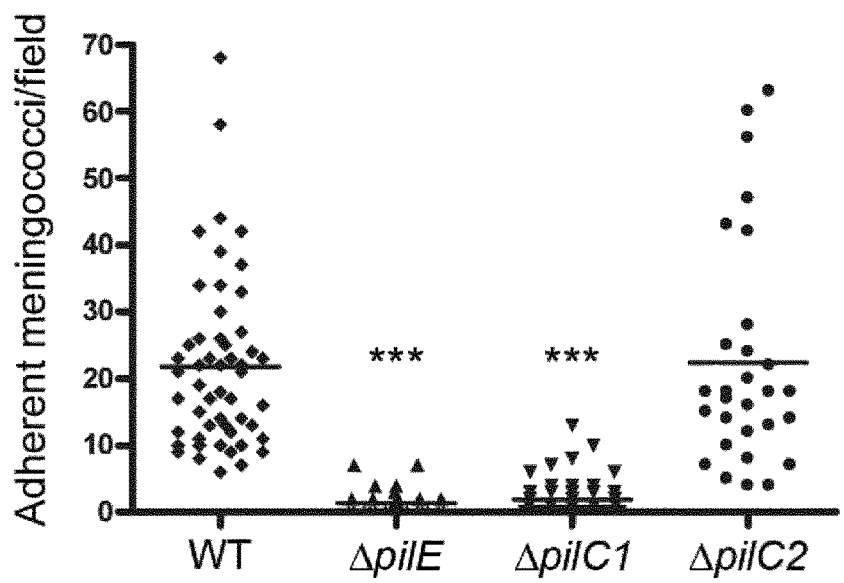

FIG. 10. Wild type (WT), dpilE, dpilC1 or dpilC2 meningococci adhering to immobilised CD147-Fc. Bar: mean per field. Mean±s.e.m, n=4;***P<0.001; One-way Anova.

Figure 11:
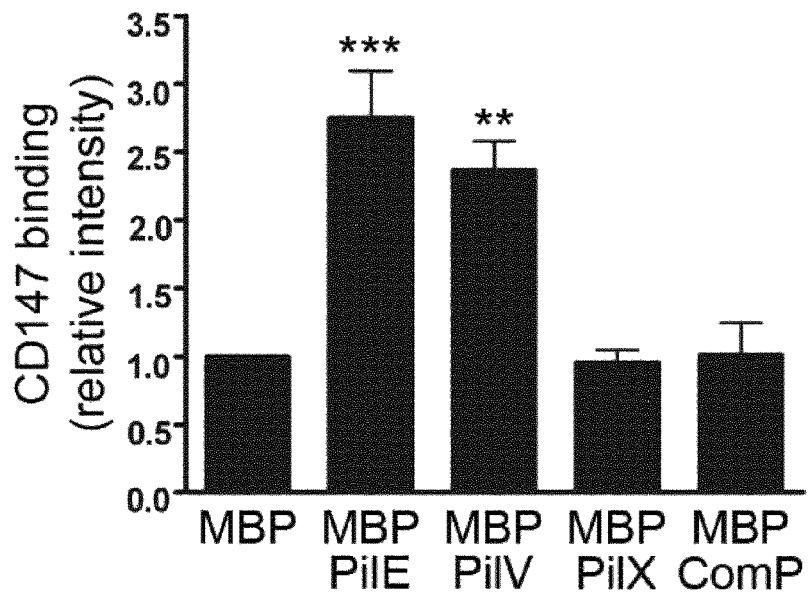

FIG. 11. Purified MBP-PilE and MBP-PilV chimera interact directly with CD147-Fc, whereas MBP-PilX, MBP-ComP and MBP did not. Top: CD147-Fc co-precipitating with staphylococci carrying the MBP-Pilins indicated. Bottom: Quantification of bound CD147-Fc. Mean±s.e.m, n=4; *P<0.001; P<0.01; One-way Anova.

Figure 12:
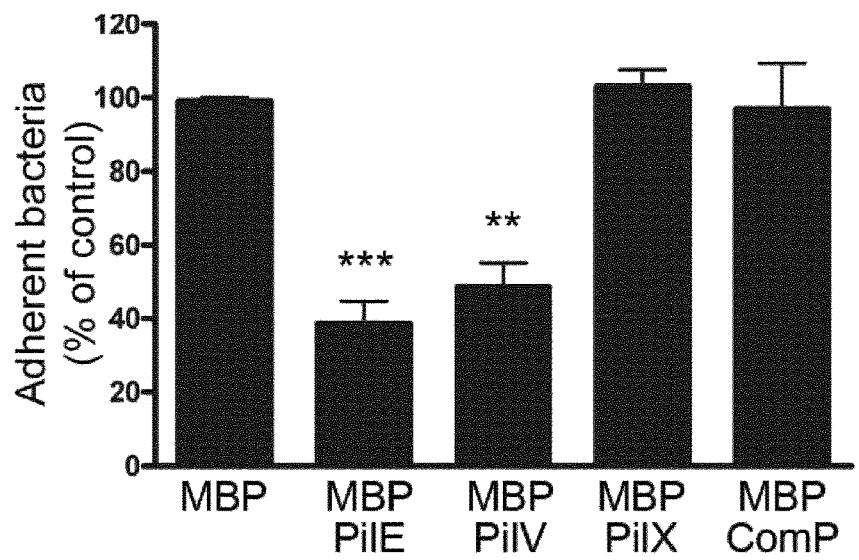

FIG. 12. Soluble MBP-PilE and MBP-PilV potently inhibited bacterial adhesion to hCMEC/D3 cells, whereas MBP-PilX, MBP-ComP and MBP were ineffective. Mean±s.e.m, n=4; *P<0.001; P<0.01; One-way Anova.

Figure 13:
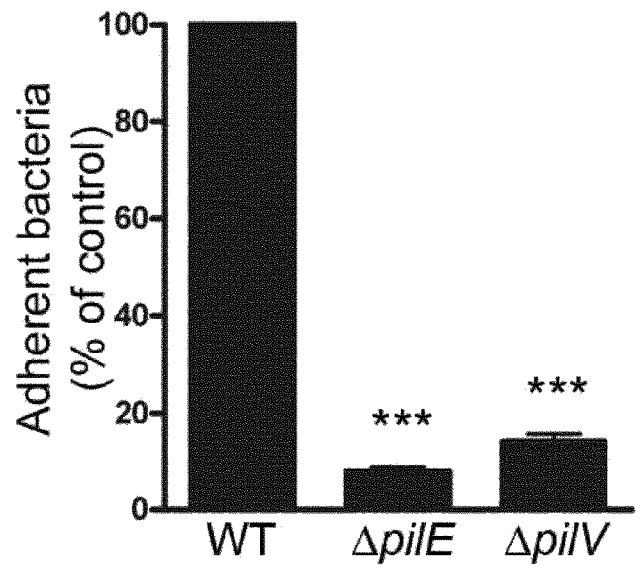

FIG. 13. Bacterial mutants ΔpilE and ΔpilV failed to adhere to hCMEC/D3 cells. Mean±s.e.m, n=4; ***P<0.001; One-way Anova.

Figure 14:
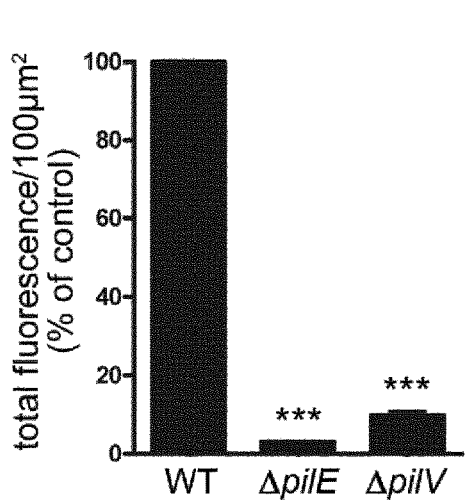

FIG. 14. Quantification of adherent fluorescent meningococci/100 µm2 section, expressed as % of adherent WT. Mean±s.e.m n=3, brain sections from 3 different donors, ***P<0.001; One-way Anova.

Figure 15:
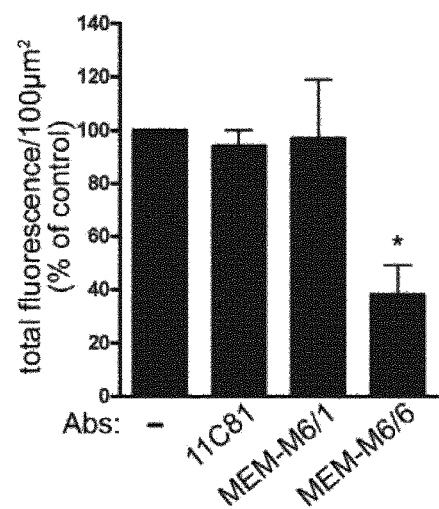

FIG. 15. In Situ infection of fresh human brain sections by *N. meningitidis* required pilus interaction with CD147. Mean±s.e.m of total fluorescence/100 µm2 relative to fluorescence in absence of antibody, n=4, brain sections from 3 different donors, *P<0.05; One-way Anova.

Figure 16:
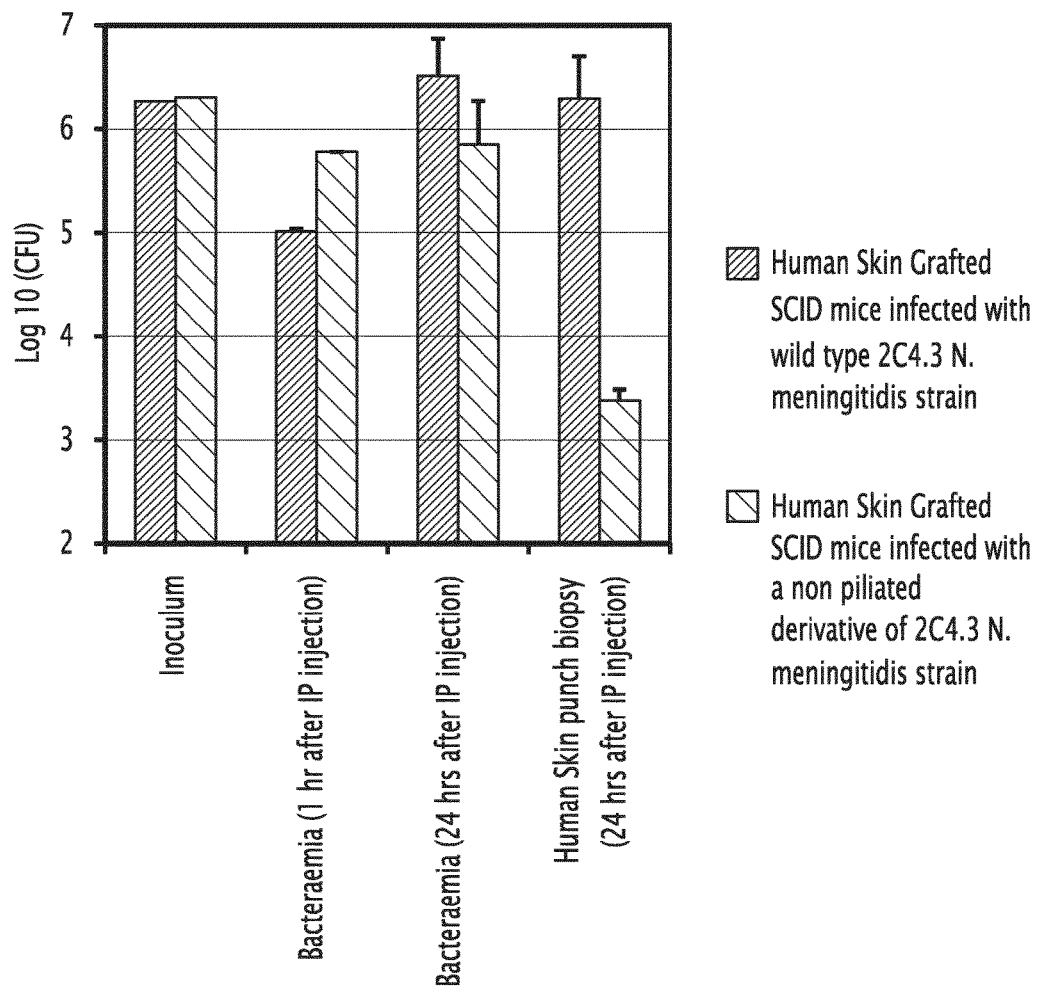

FIG. 16. The pilus of *Neisseria meningitidis* is required for targeting human skin xenografts of SCID mice (Intraperitoneal route, $10^6$ CFUs, 3 mice per group).

Figure 17:
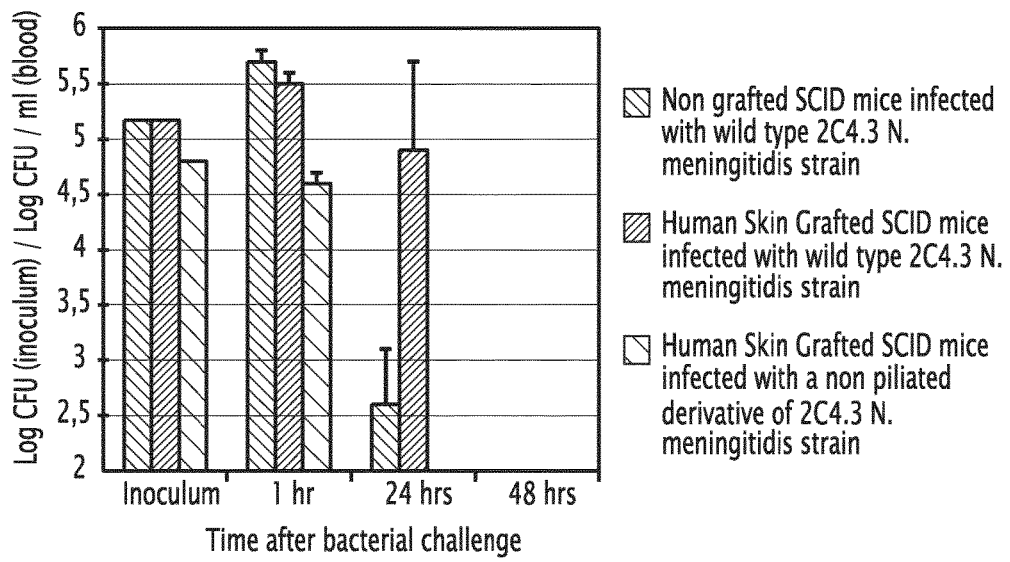

FIG. 17. Impact of human skin xenograft on bacteraemia in SCID mice (Intraveinous route, $10^5$ CFUs, 3 mice per group).

Figure 18:
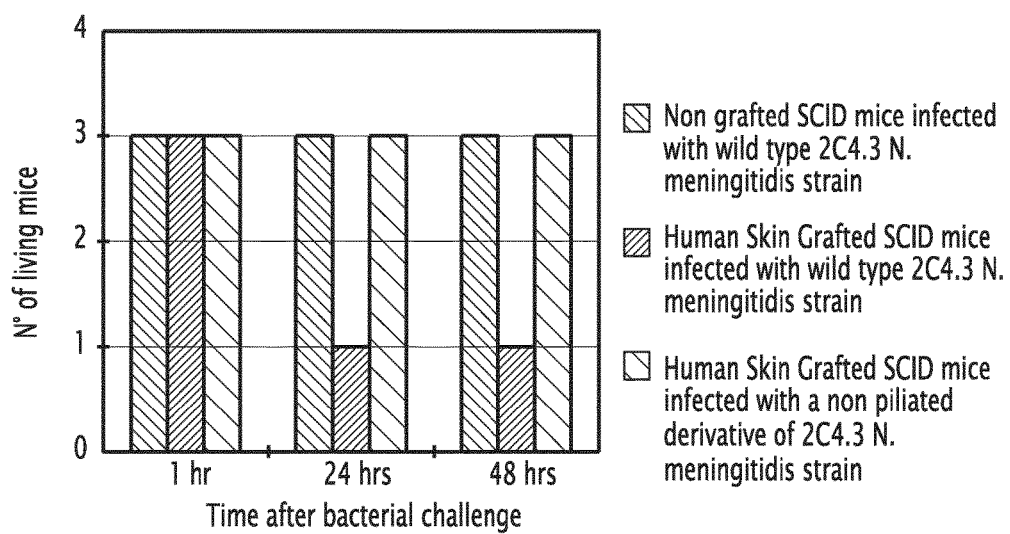

FIG. 18. Survival of *Neisseria meningitidis* infected SCID mice (Intraveinous route, $10^5$ CFUs, 3 mice per group).

BRIEF DESCRIPTION OF THE SEQUENCE LISTING

SEQ ID NOs: 1 to 5 show the sequences of the siRNA against CD147.

SEQ ID NO: 6 shows the sequence of the extracellular domain of CD147.

SEQ ID NO: 7 shows the amino acid sequence of CD147 referenced under the NCBI Reference Sequence Number NP_001719.2.

SEQ ID NO: 8 shows the amino acid sequence of CD147 referenced under the NCBI Reference Sequence Number NP_940991.1.

SEQ ID NO: 9 shows the nucleotidic sequence of CD147 referenced under the NCBI Reference Sequence Number NM_001728.2.

SEQ ID NO: 10 shows the nucleotidic sequence of CD147 referenced under the NCBI Reference Sequence Number NM_198589.1.

SEQ ID NOs: 11 and 12 show amino acid sequences of PilE.

SEQ ID NO: 13 shows the amino acid sequence of PilV.

SEQ ID NO: 14 shows the amino acid sequence of PilX.

SEQ ID NO: 15 shows the amino acid sequence of PilC.

SEQ ID NO: 16 shows the amino acid sequence of ComP.

SEQ ID NOs: 17 and 18 show amino acid sequences of fHBP.

SEQ ID NO: 19 shows the amino acid sequence of PorA.

SEQ ID NO: 20 shows the amino acid sequence of NHBA.

SEQ ID NO: 21 shows the amino acid sequence of NadA.

SEQ ID NOs: 22 to 24 show amino acid sequences of MafA.

SEQ ID NO: 25 shows the amino acid sequence of NspA.

SEQ ID NO: 26 shows the amino acid sequence of HmbR.

SEQ ID NO: 27 shows the amino acid sequence of TbpB.

SEQ ID NO: 28 shows the amino acid sequence of AusP.

SEQ ID NO: 29 shows the sequence of the hydrophobic domain of PilE.

SEQ ID NO: 30 shows the sequence of the hydrophobic domain of PilV.

SEQ ID NOs: 31 and 33 show the sequences of immunogenic fragments of PilE.

SEQ ID NOs: 32 and 34 show the sequences of immunogenic fragments of PilV.

SEQ ID NOs: 35 and 36 show the sequences of the fusion proteins between PilE and fHBP polypeptides.

SEQ ID NOs: 37 and 38 show the sequences of the fusion proteins between PilV and fHBP polypeptides.

SEQ ID NO: 39 shows the sequence of a control siRNA.

EXAMPLES

Material and Methods
Serial Analysis of Gene Expression Adapted for Downsized Extracts (SADE).

200 µg of RNA extracted from 2×107 untreated or TPA treated BB19 cells 16 hours after treatment with TPA, was used as a substrate for SADE. The SADE screen was carried out as described in Virlon et al. 1999, Proc Natl Acad Sci USA, 96:15286-15291. Briefly, total RNA was extracted from cells, poly-adenylated RNA was selected on oligo-dT columns and tagged cDNA was synthesized from the poly-A RNAs. Concatemers of DNA tags were sequenced and the number of sequenced tags differentially represented in the two libraries was determined and analysed using Monte Carlo statistical analysis.

Antibodies and Reagents

Anti-hCD147 antibodies were purchased from AbD Serotec, anti-hCD44 mAb from Immunotech, antihlCAM-1 from R&D Systems, anti-GFAP and anti-vimentin from Sigma Aldrich. Polyclonal antiserum raised against ezrin was obtained from P. Mangeat (CNRS UMR 5539, Montpelier, France). mAb raised against PilE (20D9) and polyclonal antiserum raised against meningococcal 2C4.3 strain were described previously (Coureuil et al. 2010, Cell, 143:1149-1160). Secondary antibodies used for immunofluorescence labeling, chromogenic immunohistochemistry and immunoblotting were from Jackson ImmunoResearch Laboratories. Soluble chimeric CD147-Fc and ICAM-1-Fc molecules were purchased from R&D Systems. DAPI, Rhoda minephalloidin, TPA, Actinomycin D, Isoproterenol, DAB Peroxidase Substrate and NBT/BCIP phosphatase alkaline substrate were purchased from Sigma Aldrich.

Cell Culture, Transfection and Infection

BB19, a human brain endothelial cell line transformed by papilloma virus was kindly provided by Dr J A. Nelson (Oregon Health and Science University, Beaverton, USA) (Prudhomme et al., 1996, Int J Parasitol, 26:647-655). To induce bacterial adhesion, BB19 were treated with TPA (10 ng/ml, for 10 minutes), washed and 48 h after treatment, meningococcal adhesion was measured. When indicated 2 h after TPA treatment the transcriptional inhibitor Actinomycin D was added (1 µg/ml, for 4 h), cells were washed and adhesion was measured 42 h later. The hCMEC/D3 and hBMEC cell lines were transfected and infected as previously described (Coureuil et al., 2010, Cell, 143:1149-1160; Doulet et al., 2006, J Cell Biol, 173-627-637). Plasmid encoding human CD147 was kindly provided by Dr Bukrinsky and plasmid encoding β2-Adrenergic receptor fused to YFP (p2AR-YFP) was described previously (Angers et al., 2000, Proc Natl Acad Sci USA, 97:3684-3689). To silence the expression of CD147, CD44 and ICAM-1, pools of four siRNA duplexes (ON-TARGET plus SMARTpool siRNA from Dharmacon) were used. The siCONTROL siRNA (Dharmacon) were used as control. Two days after transfection, efficiency of knockdown was assessed by FACS analysis and cells were infected concurrently. When indicated hBMEC cells were transfected with siRNA targeting the 3' untranslated region of CD147, 3'-GCUGUCUG-GUUGCGCCAUUUU-5' (SEQ ID NO: 1) or control siRNA 3'-AUGUAUUGGCCUGUAUAG-5' (SEQ ID NO: 39) (Eurogentech) and 40 h later, cells were again either mock transfected (-) or transfected with CD147 coding region cDNA. 8 hours later, surface expression of CD147 was quantified by FACS analysis and cells were infected concurrently with Nm 8013 clone 12, capsulated, Opa-, Opc- serogroup C clinical isolate expressing a class I SB pilin.

Mutants of this strain Api1C1, Api1C2, ApilE, ApilV, ApilX, AcomP and wild type Nm expressing GFP were derived and cultured as described previously (Nassif et al., 1994, Proc Natl Acad Sci USA, 91:3769-3773; Mikaty et al., 2009, PloS Pathog, 5:e1000314; Helaine et al., 2005, Mol Microbiol, 55:65-77; Mairey et al., 2006, J Exp Med, 203:1939-1950).

Adhesion Assays

Meningococcal adhesion on hCMEC/D3, hBMEC and BB19 was assayed under both static and shear stress conditions, as previously described (Coureuil et al. 2010, Cell, 143:1149-1160; Mairey et al. 2006, J Exp Med, 203:1939-1950; Lambotin et al. 2005, J Cell Sci, 118:3805-3816). When indicated meningococci were pre-incubated with 5 µg/ml soluble recombinant recombinant human CD147-Fc and ICAM-1-Fc chimera (comprising the Ig domains of CD147 or of ICAM-1 fused to the Fc domain of human IgG1 and produced as disulfide-linked homodimers) before interaction with hBMECs with additional 2 µg/ml soluble proteins. Meningococcal adhesion was quantified following a 30 min infection in static conditions. To address the inhibitory effect of antibodies, hBMECs were grown on IBIDI chambers, pretreated for 1 h with 10 µg/ml antibodies targeting ICAM-1 (11C81) or CD147 (MEM-M6/1 and MEM-M6/6) and submitted to laminar flow (0.04 dynes/cm$^2$) under an inverted microscope. GFP-expressing bacteria were introduced in the chamber under flow. After 20 min, the number of adherent bacteria was determined. For adhesion assays on immobilised proteins, recombinant human CD147-Fc and ICAM1-Fc chimera were immobilised on glass slides using a modification of the technique described in Steffen et al. 2008, Curr Biol, 18:926-931. Briefly, slides were coated with 0.1% Poly-L Lysine, washed with PBS, crosslinked with glutaraldehyde (0.5%), washed, incubated with anti-Fc in assay buffer (PBS with 3% BSA) for 2 h, washed in assay buffer, and incubated overnight at 4° C. with 2 µg/ml chimeric protein. Slides were washed before infection with meningococcal suspension of $OD_{600}$ 0.05. After incubation with bacteria, slides were washed three times and fixed. Bacteria were labelled and visualized with a Leica DMI6000 microscope using a 63× oil-immersion objective. The number of adherent bacteria per field was quantified for 30 fields using ImageJ software.

Expression, Purification and Immobilisation of MBP-Pilin Recombinant Proteins

Fragments of PilE, PilV, PilX and Comp lacking the region coding for amino acid residues 1 to 28 of the full-length proteins fused to the maltose-binding protein (MBP) were produced in E. Coli, purified on amylose resin (New England Biolabs) and immobilised on Staphylococcus aureus (ATCC 25923) expressing specific receptors for the Fc domain of IgG as described before (Coureuil et al. 2010, Cell, 143:1149-1160). Coated bacteria were incubated with 1 µg of recombinant human CD147-Fc chimera for 30 min on ice. After 3 washes, bacteria were lysed with Laemmli buffer and the quantity of co-precipitated CD147-Fc protein was assessed by immunoblot analysis. Bound CD147-Fc was quantified using Image J software. When indicated, hCMEC/D3 cells were pretreated with 10 µg/ml of MBP-Pilins for 15 min prior to infection with meningococcal suspension of $OD_{600}$ 0.05 for 30 min. After incubation with bacteria, cells were washed three times and the number of adherent bacteria was determined as described above.

Confocal Immunofluorescence Microscopy hCMEC/D3, BB19 or hBMEC were grown to confluence on permanox coverslips or on transwell filters. After the indicated treatments and/or infection, cells were fixed and labelled as previously described (Lambotin et al. 2005, J Cell Sci, 118:3805-3816; Hoffmann et al. 2001, J Cell Biol, 155:133-143). Image acquisition and analysis were performed with a DM16000 microscope (Leica, 63×). Series of optical sections were obtained with a confocal spinning disk microscope (Leica, 63×). 3D reconstructions were obtained using Imaris software and quantification histograms with ImageJ software (NIH). Quantitative analysis of protein recruitment under bacterial colonies was determined as the proportion of colonies positive for the protein of interest indicated. At least 50 colonies were observed per coverslip. Each experiment was repeated at least 3 times in duplicate or triplicate.

Infection of Human Brain Tissues

Fresh human brain sections were obtained from frontal lobe specimens of macroscopically and histologically normal brain (confirmed by a neuropathologist) of individuals referred to the Department of Forensic Medicine for unexplained out-of-hospital sudden death (consent forms ML1094, PFS 10-008, ClinicalTrials.gov NCT00320099 from The Institutional Review Boards of the Poincaré Hospital, Versailles-Saint Quentin University and the French "Agence de la Biomédecine").

After freezing of the brain tissue with isopentane cooled in liquid nitrogen, the sections, 7 µm thick, containing leptomeninges, cortical ribbon and the underlying white matter were immobilised on SUPERFROST® plus microscope slides and store at −80° C. Defrosted sections were rehydrated in PBS for 5 minutes and incubated for 1 h with medium containing 0.1% BSA prior to infection with suspensions of bacteria ($2.10^7$ bacteria in 150 µl of medium containing 0.1% BSA) for 1 h at 37° C. Sections were then gently washed horizontally 5 times and fixed in PAF 4% for 10 min at RT. When indicated, sections were treated for 1 h with 10 µg/ml of antibodies targeting CD147 or ICAM-1 and then washed 3 times prior to infection by bacteria. Adherent meningococci were detected by chromogenic immunohistochemistry and immunofluorescence analysis. To perform chromogenic immunohistochemistry, after tissue rehydratation, sections were incubated overnight with the indicated primary antibodies and revealed using horseradish peroxidase coupled secondary donkey anti-mouse antibody and an alkaline phosphatase donkey anti-rabbit. DAB (brown color) and NBT/BCIP (blue color) were used as chromogens. For immunofluorescence analysis, brain sections were incubated with the primary antibodies indicated for 2 h in PBS/BSA 0.1%. Alexa-conjugated phalloidin and DAPI (0.5 mg/ml) were added to Alexa-conjugated secondary antibodies for 1 h. After additional washing, coverslips were mounted in GLYCERGEL® (Dako). Entire samples were scanned using Nanozoomer 2.0 (Hamamatsu) and were further analysed using optical microscopy, epifluorescence (Zeiss Axiovert, 40×) and confocal (spinning disk Leica, 63×) microscopy. The marker specificities were systematically confirmed by examining sections in which primary antibody was replaced with isotype control Ig at the same concentration, and by immunostaining of non infected tissues from the same donor. Quantification analysis of the fluorescently labelled bacteria that adhered on a 1 mm$^2$ surface area was performed using ImageJ software (NIH). Results are presented as a mean of fluorescence per 100µ$^2$, from two independent experiments. 3D reconstructions were performed on deconvoluted confocal stacks using Imaris software.

ALPHASCREEN® Assay

The ALPHASCREEN® technology was used to assess the interaction between MBP-Pilin recombinant fusion proteins and CD147-Fc-His or ALCAM-1-Fc-His as a control. The binding reaction was performed using white 384-well OPTIPLATES® (PerkinElmer, Whalham, Mass., USA) in 20 µl (total reaction volume). The ALPHASCREEN® reagents (anti-MBP-coated Acceptor beads and Nickel chelate-coated Donor beads) were obtained from PerkinElmer. CD147-Fc-His (or ALCAM-1-Fc-His) and Pilin-MBP were prepared in 20 mM Tris, pH 7.4, 20 mM NaCl. Donor beads (20 µg/ml) were incubated with CD147-His (0, 100 or 500 nM) for 45 min at room temperature. In parallel Acceptor beads (20 µg/ml) were incubated with Pilin-MBP (0, 50 or 500 nM) for 1 h at room temperature in the ALPHASCREEN® reaction buffer (25 mM Tris, pH 7.4 at 20° C., 20 mM NaCl, 0.1% BSA and 0.05% Tween 20). Then, 10 µl of each of the interacting partners were added to the plate, allowed for incubation for either 2 h or overnight in the dark and at room temperature. To perform antibody competition assay, 5 µl of MEM-M-6/6 antibody (at various concentrations) were added to CD147-Fc-His-Donor beads for 30 min at room temperature before incubation with the Pilin-MBP Acceptor beads. Light signal was detected by using the ENVISION® multilabel plate reader (PerkinElmer). All manipulations involving ALPHASCREEN® beads were performed under subdued lighting.

Results and Discussion

To identify candidate receptors responsible for the initial attachment of Nm Type IV pili expressed by endothelial cells, it has been taken advantage of the inducible expression of a functional receptor on BB19, a transformed human brain endothelial cell line that is poorly permissive to Nm adhesion. Treatment of BB19 cells with phorbol ester 12-O-Tetradecanoylphorbol-13-acetate (TPA) strongly potentiated adhesion of Nm 8013 clone 12, a capsulated piliated clinical isolate of serogroup C (FIG. 1). This effect was inhibited by treatment with the transcription inhibitor actinomycin D (FIG. 1). Furthermore, only the wild type strain and the bacterial pilC2 deletion mutant that harbour adhesive pili, adhered to TPA treated cells, in sharp contrast to the non piliated pilE and the non adhesive pilC1 mutants, which failed to do so (FIG. 2). These data highlighted the transcriptional regulation of a putative adhesion receptor for meningococcal type IV pili. Using a differential and quantitative large-scale analysis of expression of 10 478 genes (see Methods), 211 up-regulated and 194 down-regulated genes were identified in TPA-treated BB19 cells compared to untreated cells. Of the up-regulated genes, six encoded membrane-associated proteins, including CD147, a well known marker of the blood brain barrier (BBB), highly enriched on brain endothelial cells to which Nm preferentially adhere. CD147 is a member of the immunoglobulin (Ig) superfamily, containing two glycosylated Ig-like domains, involved in various physiological and pathological processes. It has been confirmed that TPA treatment of BB19 cells up-regulated the expression of CD147. Furthermore adhesion of Nm to TPA-treated cells induced a massive recruitment of CD147 to sites of bacterial adhesion. CD147 thus appeared to be an attractive receptor candidate for type IV pilus-mediated Nm adhesion.

To investigate the role of CD147 in the adhesion of Nm to endothelial cells, two cell lines were used as models. hCMEC/D3 is a fully differentiated human brain endothelial cell line derived from brain capillaries, which recapitulates the major phenotypic features of the BBB, and hBMEC, a human endothelial cell line isolated from bone marrow capillaries. As expected, CD147 was predominantly enriched at cell-cell junctions of a polarized monolayer of hCMEC/D3 cells and a significant fraction of CD147 was present at the luminal surface. In cells infected by Nm, CD147 accumulated at sites of meningococcal adhesion and co-localised with the $\beta2$-adrenergic receptor. Importantly, CD147 was recruited independently of the $\beta2$-adrenergic receptor expression and associated-coupled signalling events, as expected of a putative receptor mediating the initial bacterial adhesion (FIG. 3).

To establish whether CD147 was required for meningococcal adhesion, hCMEC/D3 and hBMEC cells were transfected with CD147-specific small interfering RNAs (siRNA) that knocked down 60 to 70% of the surface expression of CD147 relative to control siRNA. Bacterial adhesion to cells in which CD147 was knocked down was drastically reduced (FIGS. 4 and 5). This effect was restored by the re-expression of exogenous CD147 (FIG. 5). Importantly, CD147 depletion also affected bacterial adhesion under flow conditions, in a quantitative assay of the initial adhesion events (FIG. 6), indicating that CD147 is essential to promote the initial attachment of meningococci to human endothelial cells. In contrast, a similar depletion of CD44 or ICAM-1 expression, two adhesion molecules recruited at sites of bacterial adhesion upon type-IV mediated signalling events, did not affect meningococcal adhesion to either hCMEC/D3 or hBMEC cells, therefore supporting the specific effect of CD147 depletion on meningococcal adhesion to human endothelial cells.

To further confirm the role of CD147 in Nm adhesion to endothelial cells, a recombinant soluble form of the extracellular domain of CD147 (CD147-Fc) was used to specifically compete with the membrane-bound receptor. Addition of CD147-Fc reduced bacterial adhesion to hBMEC cells by 50% compared to non-treated cells or cells treated with control soluble ICAM-1-Fc (FIG. 7). An independent approach relied on the use of two CD147-specific antibodies, MEM-M6/1 and MEMM6/6, binding to the N-terminal and the C-terminal Ig domain of CD147, respectively. Interestingly, when added to hBMECs before infection, MEM-M6/6 inhibited by 75% the initial attachment of Nm under flow conditions compared to cells pre-treated with anti-ICAM-1 control antibody (11C81), whereas MEM-M6/1 only reduced initial attachment by 20% (FIG. 8). Importantly, MEM-M6/1 and MEM-M6/6 both labelled CD147 expressed on hCMEC/D3 cells similarly. However only MEM-M6/1 efficiently labelled CD147 molecules accumulated at sites of bacterial adhesion, indicating that MEM-M6/6 and meningococci compete for the same binding motif on CD147. Overall, our data indicate that CD147 is a critical endothelial receptor for the primary attachment of Nm to human endothelial cells.

Next, we examined whether Nm could directly adhere on purified CD147-Fc molecules immobilised on glass support. Remarkably, the number of meningococci adhering to CD147-Fc was 4 to 5 fold higher than the number of bacteria adhering to ICAM-Fc or to the control condition with no immobilised protein (negative) (FIG. 9). Consistent with a role for meningococcal type IV pili in this direct interaction, wild type and pilC2 mutant strains adhere to immobilised CD147-Fc, in contrast to pilE and pilC1 mutants (FIG. 10). To identify the CD147 'ligand(s)' among pilus components, we assessed the interaction between soluble CD147-Fc molecules and purified recombinant pilins produced as fusion proteins with the maltose binding protein (MBP) and immobilised on staphylococci (as described in Coureuil et al. 2010, Cell, 143:1149-1160) (FIG. 11). Interestingly, purified PilE interacted with CD147-Fc molecules. A similar interaction was observed with the minor pilin PilV, while no significant interaction was detected with the minor pilins PilX or ComP. To further analyse the relative contribution of each pilin to meningococcal adhesion to endothelial cells, infections of hCMEC/D3 cells with wild-type Nm were performed in the presence of purified pilins, to assess their ability to compete for binding to the membrane receptor (FIG. 12). Remarkably, addition of PilE or PilV reduced bacterial adhesion by 60% and 50%, respectively, whereas addition of PilX or ComP proteins had no effect (FIG. 12). Consistently, a pilV deletion mutant, which remains piliated unlike a pilE mutant, abolished bacterial adhesion to hCMEC/D3 cells (FIG. 13). Altogether, these results point to a key role for a selective interaction between PilE and PilV with CD147 in meningococcal initial adhesion to endothelial cells.

To assess the relevance of this finding in Nm infection in humans, the ability of live pathogenic meningococci to adhere on fresh brain sections obtained from frontal specimens of normal human brains was explored. Remarkably, bacteria predominantly established tight association with brain vessels of the leptomeninges (within Virchow-Robin spaces) and of cortical region. Importantly, this localisation, highly reminiscent of neuropathological observations in bacterial meningitis, relied on the expression of both pilins PilE and PilV. Indeed, pilE or pilV deletion mutants adhered poorly to brain sections from the same donor compared to wild type Nm (FIG. 14). Wild type bacteria formed colonies on the luminal side of meningeal and cortical brain vessels which are lined with endothelial cells expressing CD147. In addition, bacterial colonies were found in association with CD147+ leptomeningeal cells, but not with glial nor neuronal cells that do not express CD147, demonstrating that bacterial adhesion to fresh human brain tissues closely correlated with CD147 expression. Finally, pre-treatment of brain sections with MEM-M6/6 prior to infection by Nm drastically reduced brain colonisation, whereas MEM-M6/1 and 11C81 antibodies were ineffective (FIG. 15). These results, in line with our data using cultured endothelial cells, confirmed that the C-terminal domain of CD147 is essential for in situ infection of cerebral blood vessels.

Overall, this study demonstrates that CD147 is an essential receptor for the initial adhesion of Nm to brain and peripheral human endothelial cells by interacting directly with the pilus components PilE and PilV. Importantly, it provides the first demonstration in situ of an elective targeting of cerebral blood vessels by pathogenic meningococci, relying on specific interactions between microbial ligands and a brain receptor. Because of its key position in the pathophysiological cascade of tissue colonization by Nm, CD147 becomes a major pharmacological target to inhibit meningococcal blood-borne infection of the brain and of peripheral capillaries. The lack of animal model of meningococcal infection has hampered the understanding of meningococcal pathogenesis. N. meningitidis interacts only with cells of human origin and only adheres to human cells, thus preventing the study of the role of meningococcal cell interaction in meningococcal pathogenesis using animal models.

A model using severe combined immunodeficient (SCID) mouse grafted with human skin have been set up. Previous reports have shown that 4-6 weeks after engraftment the human skin graft maintained characteristics of normal human skin, including its micro-vasculature (Yan et al. 1993, J Clin Invest, 91: 986; Gilet et al., 2009, J Invest Dermatol, 129: 879. Briefly, normal human adult skin removed during plastic surgery was grafted on the back of SCID mice. One month later, mice are infected by intraperitoneal or intravenous injection of capsulated piliated meningococci. Histopathological examination revealed that N. meningitidis specifically targets draining vessels of the xenograft (but not that of normal mice skin), adhere to the endothelium and form obliterating colonies within the lumen of vessels. FIG. 16 clearly shows that in SCID mice grafted with human skin, piliated capsulated bacteria which are able to interact with cells are in much higher number in the human skin than non piliated capsulated bacteria unable to interact with human skin. This was confirmed by histological examination. Indeed non piliated bacteria were unable to adhere in vivo to the human endothelial cells of the graft. These data demonstrate that piliation is required for bacterial interaction in vivo with human cells.

The high level of the bacteraemia is believed to be of the utmost importance for meningococcal pathogenesis. The virulence factors known to allow the establishment of this bacteraemia are the capsule, the lipooligosaccharide, the factor H binding proteins and the iron chelation systems. These virulence factors allow the bacteria to survive in the extracellular fluids. Using the SCID mice model, we tested the hypothesis that the ability of the bacteria to interact and to multiply within the blood vessels was also participating in the establishment of the bacteraemia. As shown FIG. 17, when piliated bacteria are injected in grafted human skin mice, the bacteraemia remains much higher than when similar bacteria are injected in non-grafted mice, thus suggesting that the interaction of the bacteria with the human skin allows the establishment of the bacteraemia. The role of the type IV pili was confirmed by the fact that injection of non piliated meningococci (unable to adhere to endothelial cells) are clearing the bacteria from the bloodstream unlike what is observed with piliated bacteria. To confirm the role of this interaction in meningococcal pathogenesis, the virulence of piliated meningococci between injected grafted mice or injected non-grafted mice has been compared. As shown FIG. 18, 2 out of 3 grafted mice died whereas all non grafted mice survived.

Altogether these data demonstrate that the establishment of a meningococcal bacteraemia requires not only the capsule, lipooligosaccharide, factor H binding proteins and iron chelation system, but also pili which promote the interaction of the bacteria with the endothelial cells. In addition, this interaction with endothelial cells is essential for meningococcal pathogenesis (FIG. 18). These data suggest that inhibiting this interaction will prevent meningococcal infection, and that a vaccine aiming at decreasing the meningococcal cell interaction will be efficient at preventing meningococcal infection.

Finally, an Alphascreen test allowing to measure the interaction between pilins and CD147 ectodomain has been developed. A dose dependent interaction between CD147-Fc and both PilE and PilV, and not with the other minor pilins PilX and Comp, was detected using Alphascreen® technology, while no interaction was detected between PilE or PilV with a control protein. As expected, purified MBP-PilE-SA and MBP-PilE-SB chimera similarly interacted with CD147-Fc. Furthermore, interaction between CD147 and PilE can be successfully inhibited by the addition of the MEM-M6/6 antibody directed against the Ig proximal domain of CD147. These results suggest that the Alphascreen test can be used for the high-throughput screening of inhibitors of the interaction between type IV pilus-associated proteins and CD147.

SEQUENCE LISTING

<160> NUMBER OF SEQ ID NOS: 39

<210> SEQ ID NO 1
<211> LENGTH: 21
<212> TYPE: RNA
<213> ORGANISM: Artificial Sequence
<220> FEATURE:
<223> OTHER INFORMATION: siRNA

<400> SEQUENCE: 1
gcugucuggu ugcgccauuu u                                             21

<210> SEQ ID NO 2
<211> LENGTH: 21
<212> TYPE: RNA
<213> ORGANISM: Artificial Sequence
<220> FEATURE:
<223> OTHER INFORMATION: siRNA

<400> SEQUENCE: 2
ggucagagcu acacauugau u                                             21

<210> SEQ ID NO 3
<211> LENGTH: 21
<212> TYPE: RNA
<213> ORGANISM: Artificial Sequence
<220> FEATURE:
<223> OTHER INFORMATION: siRNA

<400> SEQUENCE: 3
gaagucguca gaacacaucu u                                             21

<210> SEQ ID NO 4
<211> LENGTH: 21
<212> TYPE: RNA
<213> ORGANISM: Artificial Sequence
<220> FEATURE:
<223> OTHER INFORMATION: siRNA

<400> SEQUENCE: 4
guacaagauc acugacucuu u                                             21

<210> SEQ ID NO 5
<211> LENGTH: 21
<212> TYPE: RNA
<213> ORGANISM: Artificial Sequence
<220> FEATURE:
<223> OTHER INFORMATION: siRNA

<400> SEQUENCE: 5
ggacaaggcc cucaugaacu u                                             21

<210> SEQ ID NO 6
<211> LENGTH: 190
<212> TYPE: PRT
<213> ORGANISM: Artificial Sequence
<220> FEATURE:
<223> OTHER INFORMATION: CD147 extracellular domain

<400> SEQUENCE: 6

Thr His Gly Ala Ser Gly Ala Ala Gly Thr Val Phe Thr Thr Val Glu
1               5                   10                  15

Asp Leu Gly Ser Lys Ile Leu Leu Thr Cys Ser Leu Asn Asp Ser Ala
            20                  25                  30

Thr Glu Val Thr Gly His Arg Trp Leu Lys Gly Gly Val Val Leu Lys

```
                    35                  40                  45
Glu Asp Ala Leu Pro Gly Gln Lys Thr Glu Phe Lys Val Asp Ser Asp
 50                  55                  60

Asp Gln Trp Gly Glu Tyr Ser Cys Val Phe Leu Pro Glu Pro Met Gly
 65                  70                  75                  80

Thr Ala Asn Ile Gln Leu His Gly Pro Pro Arg Val Lys Ala Val Lys
                 85                  90                  95

Ser Ser Glu His Ile Asn Glu Gly Glu Thr Ala Met Leu Val Cys Lys
                100                 105                 110

Ser Glu Ser Val Pro Pro Val Thr Asp Trp Ala Trp Tyr Lys Ile Thr
            115                 120                 125

Asp Ser Glu Asp Lys Ala Leu Met Asn Gly Ser Glu Ser Arg Phe Phe
            130                 135                 140

Val Ser Ser Ser Gln Gly Arg Ser Glu Leu His Ile Glu Asn Leu Asn
145                 150                 155                 160

Met Glu Ala Asp Pro Gly Gln Tyr Arg Cys Asn Gly Thr Ser Ser Lys
                165                 170                 175

Gly Ser Asp Gln Ala Ile Ile Thr Leu Arg Val Arg Ser His
                180                 185                 190

<210> SEQ ID NO 7
<211> LENGTH: 385
<212> TYPE: PRT
<213> ORGANISM: Homo sapiens

<400> SEQUENCE: 7

Met Ala Ala Ala Leu Phe Val Leu Leu Gly Phe Ala Leu Leu Gly Thr
  1               5                  10                  15

His Gly Ala Ser Gly Ala Ala Gly Phe Val Gln Ala Pro Leu Ser Gln
                 20                  25                  30

Gln Arg Trp Val Gly Gly Ser Val Glu Leu His Cys Glu Ala Val Gly
             35                  40                  45

Ser Pro Val Pro Glu Ile Gln Trp Trp Phe Glu Gly Gln Gly Pro Asn
 50                  55                  60

Asp Thr Cys Ser Gln Leu Trp Asp Gly Ala Arg Leu Asp Arg Val His
 65                  70                  75                  80

Ile His Ala Thr Tyr His Gln His Ala Ala Ser Thr Ile Ser Ile Asp
                 85                  90                  95

Thr Leu Val Glu Glu Asp Thr Gly Thr Tyr Glu Cys Arg Ala Ser Asn
                100                 105                 110

Asp Pro Asp Arg Asn His Leu Thr Arg Ala Pro Arg Val Lys Trp Val
            115                 120                 125

Arg Ala Gln Ala Val Val Leu Val Leu Glu Pro Gly Thr Val Phe Thr
            130                 135                 140

Thr Val Glu Asp Leu Gly Ser Lys Ile Leu Leu Thr Cys Ser Leu Asn
145                 150                 155                 160

Asp Ser Ala Thr Glu Val Thr Gly His Arg Trp Leu Lys Gly Gly Val
                165                 170                 175

Val Leu Lys Glu Asp Ala Leu Pro Gly Gln Lys Thr Glu Phe Lys Val
            180                 185                 190

Asp Ser Asp Asp Gln Trp Gly Glu Tyr Ser Cys Val Phe Leu Pro Glu
            195                 200                 205

Pro Met Gly Thr Ala Asn Ile Gln Leu His Gly Pro Pro Arg Val Lys
210                 215                 220
```

```
Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
            245                 250                 255

Lys Ile Thr Asp Ser Glu Asp Lys Ala Leu Met Asn Gly Ser Glu Ser
        260                 265                 270

Arg Phe Phe Val Ser Ser Ser Gln Gly Arg Ser Glu Leu His Ile Glu
    275                 280                 285

Asn Leu Asn Met Glu Ala Asp Pro Gly Gln Tyr Arg Cys Asn Gly Thr
290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
                325                 330                 335

Val Leu Val Thr Ile Ile Phe Ile Tyr Glu Lys Arg Arg Lys Pro Glu
            340                 345                 350

Asp Val Leu Asp Asp Asp Ala Gly Ser Ala Pro Leu Lys Ser Ser
            355                 360                 365

Gly Gln His Gln Asn Asp Lys Gly Lys Asn Val Arg Gln Arg Asn Ser
370                 375                 380

Ser
385

<210> SEQ ID NO 8
<211> LENGTH: 269
<212> TYPE: PRT
<213> ORGANISM: Homo sapiens

<400> SEQUENCE: 8

Met Ala Ala Ala Leu Phe Val Leu Leu Gly Phe Ala Leu Leu Gly Thr
1               5                   10                  15

His Gly Ala Ser Gly Ala Ala Gly Thr Val Phe Thr Thr Val Glu Asp
            20                  25                  30

Leu Gly Ser Lys Ile Leu Leu Thr Cys Ser Leu Asn Asp Ser Ala Thr
        35                  40                  45

Glu Val Thr Gly His Arg Trp Leu Lys Gly Gly Val Val Leu Lys Glu
50                  55                  60

Asp Ala Leu Pro Gly Gln Lys Thr Glu Phe Lys Val Asp Ser Asp Asp
65                  70                  75                  80

Gln Trp Gly Glu Tyr Ser Cys Val Phe Leu Pro Glu Pro Met Gly Thr
                85                  90                  95

Ala Asn Ile Gln Leu His Gly Pro Pro Arg Val Lys Ala Val Lys Ser
            100                 105                 110

Ser Glu His Ile Asn Glu Gly Glu Thr Ala Met Leu Val Cys Lys Ser
        115                 120                 125

Glu Ser Val Pro Pro Val Thr Asp Trp Ala Trp Tyr Lys Ile Thr Asp
    130                 135                 140

Ser Glu Asp Lys Ala Leu Met Asn Gly Ser Glu Ser Arg Phe Phe Val
145                 150                 155                 160

Ser Ser Ser Gln Gly Arg Ser Glu Leu His Ile Glu Asn Leu Asn Met
                165                 170                 175

Glu Ala Asp Pro Gly Gln Tyr Arg Cys Asn Gly Thr Ser Ser Lys Gly
            180                 185                 190

Ser Asp Gln Ala Ile Ile Thr Leu Arg Val Arg Ser His Leu Ala Ala
        195                 200                 205
```

```
Leu Trp Pro Phe Leu Gly Ile Val Ala Glu Val Leu Val Leu Val Thr
    210                 215                 220

Ile Ile Phe Ile Tyr Glu Lys Arg Arg Lys Pro Glu Asp Val Leu Asp
225                 230                 235                 240

Asp Asp Asp Ala Gly Ser Ala Pro Leu Lys Ser Ser Gly Gln His Gln
                245                 250                 255

Asn Asp Lys Gly Lys Asn Val Arg Gln Arg Asn Ser Ser
                260                 265

<210> SEQ ID NO 9
<211> LENGTH: 2107
<212> TYPE: DNA
<213> ORGANISM: Homo sapiens

<400> SEQUENCE: 9
gtacatgcga gcgtgtgcgc gcgtgcgcag gcggggcgac cggcgtcccc ggcgctcgcc      60
ccgcccccga gatgacgccg tgcgtgcgcg cgcccggtcc cgcgcctccgc cgcttttttat    120 agcggccgcg ggcggcggcg gcagcggttg gaggttgtag gaccggcgag gaataggaat     180
catggcggct gcgctgttcg tgctgctggg attcgcgctg ctgggcaccc acggagcctc     240
cggggctgcc ggcttcgtcc aggcgccgct gtcccagcag aggtgggtgg ggggcagtgt     300
ggagctgcac tgcgaggccg tgggcagccc ggtgcccgag atccagtggt ggtttgaagg     360
gcagggtccc aacgacacct gctcccagct ctgggacggc gccggctgg accgcgtcca      420 catccacgcc acctaccacc agcacgcggc cagcaccatc tccatcgaca cgctcgtgga     480
ggaggacacg ggcacttacg agtgccgggc cagcaacgac ccggatcgca accacctgac     540
ccgggcgccc agggtcaagt gggtccgcgc ccaggcagtc gtgctagtcc tggaacccgg     600
cacagtcttc actaccgtag aagaccttgg ctccaagata ctcctcacct gctccttgaa     660
tgacagcgcc acagaggtca cagggcaccg ctggctgaag gggggcgtgg tgctgaagga     720
ggacgcgctg cccggccaga aaacggagtt caaggtggac tccgacgacc agtggggaga     780
gtactcctgc gtcttcctcc ccgagcccat gggcacggcc aacatccagc tccacggggcc    840 tcccagagtg aaggctgtga gtcgtcaga acacatcaac gaggggggaga cggccatgct    900 ggtctgcaag tcagagtccg tgccacctgt cactgactgg gcctggtaca agatcactga    960
ctctgaggac aaggccctca tgaacggctc cgagagcagg ttcttcgtga gttcctcgca    1020
gggccggtca gagctacaca ttgagaacct gaacatggag gccgaccccg gccagtaccg    1080
gtgcaacggc accagctcca agggctccga ccaggccatc atcacgctcc gcgtgcgcag    1140
ccacctggcc gccctctggc ccttcctggg catcgtggct gaggtgctgg tgctggtcac    1200
catcatcttc atctacgaga agcgccggaa gcccgaggac gtcctggatg atgacgacgc    1260
cggctctgca cccctgaaga gcagcgggca gcaccagaat gacaaaggca agaacgtccg    1320
ccagaggaac tcttcctgag gcaggtggcc gaggacgct cctgctcca cgtctgcgcc      1380 gccgccggag tccactccca gtgcttgcaa gattccaagt tctcacctct aaagaaaac    1440 ccaccccgta gattcccatc atacacttcc ttctttttta aaaaagttgg gttttctcca    1500
ttcaggattc tgttccttag gttttttttcc ttctgaagtg tttcacgaga gcccgggagc    1560
tgctgccctg cggccccgtc tgtggctttc agcctctggg tctgagtcat ggccgggtgg    1620
gcggcacagc cttctccact ggccggagtc agtgccaggt ccttgccctt tgtggaaagt    1680
cacaggtcac acgaggggcc ccgtgtcctg cctgtctgaa gccaatgctg tctggttgcg    1740
```

```
ccattttttgt gcttttatgt ttaatttttat gagggccacg ggtctgtgtt cgactcagcc    1800
tcagggacga ctctgacctc ttggccacag aggactcact tgcccacacc gagggcgacc    1860
ccgtcacagc ctcaagtcac tcccaagccc cctccttgtc tgtgcatccg ggggcagctc    1920
tggagggggt tgctgggga actggcgcca tcgccgggac tccagaaccg cagaagcctc    1980
cccagctcac ccctggagga cggccggctc tctatagcac cagggctcac gtgggaaccc    2040
ccctcccacc caccgccaca ataaagatcg cccccacctc caccctcaaa aaaaaaaaa    2100 aaaaaaa                                                                2107

<210> SEQ ID NO 10
<211> LENGTH: 1759
<212> TYPE: DNA
<213> ORGANISM: Homo sapiens

<400> SEQUENCE: 10
gtacatgcga gcgtgtgcgc gcgtgcgcag gcggggcgac cggcgtcccc ggcgctcgcc     60
ccgcccccga gatgacgccg tgcgtgcgcg cgcccggtcc cgcgcctccgc cgcttttttat   120 agcggccgcg ggcggcggcg gcagcggttg gaggttgtag gaccggcgag gaataggaat    180
catgGcggct gcgctgttcg tgctgctggg attcgcgctg ctgggcaccc acggagcctc    240
cggggctgcc ggcacagtct tcactaccgt agaagacctt ggctccaaga tactcctcac    300
ctgctccttg aatgacagcg ccacagaggt cacagggcac cgctggctga agggggggcgt   360 ggtgctgaag gaggacgcgc tgcccggcca gaaaacggag ttcaaggtgg actccgacga   420
ccagtgggga gagtactcct gcgtcttcct ccccgagccc atgggcacgg ccaacatcca    480
gctccacggg cctcccagag tgaaggctgt gaagtcgtca gaacacatca acgaggggga    540
gacggccatg ctggtctgca agtcagagtc cgtgccacct gtcactgact gggcctggta    600
caagatcact gactctgagg acaaggccct catgaacggc tccgagagca ggttcttcgt    660
gagttcctcg cagggccggt cagagctaca cattgagaac ctgaacatgg aggccgaccc    720
cggccagtac cggtgcaacg gcaccagctc caagggctcc gaccaggcca tcatcacgct    780
ccgcgtgcgc agcccacctgg ccgccctctg gccccttcctg ggcatcgtgg ctgaggtgct   840
ggtgctggtc accatcatct tcatctacga gaagcgccgg aagcccgagg acgtcctgga    900
tgatgacgac gccggctctg cacccctgaa gagcagcggg cagcaccaga tgacaaagg    960 caagaacgtc cgccagagga actcttcctg aggcaggtgg cccgaggacg ctccctgctc   1020
cacgtctgcg ccgccgccgg agtccactcc cagtgcttgc aagattccaa gttctcacct   1080
cttaaagaaa acccaccccg tagattccca tcatacactt ccttctttt taaaaaagtt    1140 gggtttttctc cattcaggat tctgttcctt aggtttttt ccttctgaag tgtttcacga   1200
gagcccggga gctgctgccc tgcggccccg tctgtggctt tcagcctctg ggtctgagtc   1260
atggccgggt gggcggcaca gccttctcca ctggccggag tcagtgccag tccttgccc    1320 tttgtggaaa gtcacaggtc acacgagggg ccccgtgtcc tgcctgtctg aagccaatgc    1380
tgtctggttg cgccattttt gtgcttttat gtttaatttt atgagggcca cgggtctgtg    1440
ttcgactcag cctcagggac gactctgacc tcttggccac agaggactca cttgcccaca    1500
ccgagggcga ccccgtcaca gcctcaagtc actcccaagc cccctccttg tctgtgcatc    1560 cgggggcag tctggagggg gtttgctggg gaactggcgc catcgccggg actccagaac    1620
cgcagaagcc tccccagctc accctggag gacggccgg tctctatagc accagggctc    1680
acgtgggaac ccccctccca cccaccgcca caataaagat cgcccccacc tccaccctca    1740
```
aaaaaaaaaa aaaaaaaa                                                  1759

<210> SEQ ID NO 11
<211> LENGTH: 168
<212> TYPE: PRT
<213> ORGANISM: Neisseria meningitidis

<400> SEQUENCE: 11

Met Asn Thr Leu Gln Lys Gly Phe Thr Leu Ile Glu Leu Met Ile Val
1               5                   10                  15

Ile Ala Ile Val Gly Ile Leu Ala Ala Val Ala Leu Pro Ala Tyr Gln
                20                  25                  30

Asp Tyr Thr Ala Arg Ala Gln Val Ser Glu Ala Ile Leu Leu Ala Glu
            35                  40                  45

Gly Gln Lys Ser Ala Val Thr Glu Tyr Tyr Leu Asn His Gly Glu Trp
        50                  55                  60

Pro Gly Asp Asn Ser Ser Ala Gly Val Ala Thr Ser Ala Asp Ile Lys
65                  70                  75                  80

Gly Lys Tyr Val Gln Ser Val Thr Val Ala Asn Gly Val Ile Thr Ala
                85                  90                  95

Gln Met Ala Ser Ser Asn Val Asn Asn Glu Ile Lys Ser Lys Lys Leu
            100                 105                 110

Ser Leu Trp Ala Lys Arg Gln Asn Gly Ser Val Lys Trp Phe Cys Gly
        115                 120                 125

Gln Pro Val Thr Arg Thr Thr Ala Thr Ala Thr Asp Val Ala Ala Ala
    130                 135                 140

Asn Gly Lys Thr Asp Asp Lys Ile Asn Thr Lys His Leu Pro Ser Thr
145                 150                 155                 160

Cys Arg Asp Asp Ser Ser Ala Ser
                165

<210> SEQ ID NO 12
<211> LENGTH: 148
<212> TYPE: PRT
<213> ORGANISM: Neisseria meningitidis

<400> SEQUENCE: 12

Met Lys Ala Ile Gln Lys Gly Phe Thr Leu Ile Glu Leu Met Ile Val
1               5                   10                  15

Ile Ala Ile Val Gly Ile Leu Ala Ala Val Ala Leu Pro Ala Tyr Gln
                20                  25                  30

Asp Tyr Thr Ala Arg Ala Gln Met Ser Glu Ala Leu Thr Leu Ala Glu
            35                  40                  45

Gly Gln Lys Ser Ala Val Ile Glu Tyr Tyr Ser Asp Asn Gly Thr Phe
        50                  55                  60

Pro Asn Ser Asn Thr Ser Ala Gly Ile Ala Ala Ser Asn Glu Ile Lys
65                  70                  75                  80

Gly Lys Tyr Val Ala Ser Val Lys Val Glu Gly Asn Ala Ser Val Ala
                85                  90                  95

Ser Ile Thr Ala Thr Met Asn Ser Asn Val Asn Lys Asp Ile Lys
            100                 105                 110

Gly Lys Thr Leu Val Leu Val Gly Lys Gln Asn Ser Gly Ser Phe Ser
        115                 120                 125

Trp Gly Cys Lys Lys Gly Ser Val Asp Glu Lys Phe Leu Pro Ser Thr
    130                 135                 140

```
Cys Arg Thr Lys
145

<210> SEQ ID NO 13
<211> LENGTH: 129
<212> TYPE: PRT
<213> ORGANISM: Neisseria meningitidis

<400> SEQUENCE: 13

Met Lys Asn Val Gln Lys Gly Phe Thr Leu Leu Glu Leu Met Ile Ala
1               5                   10                  15

Val Ala Ile Leu Gly Ile Leu Thr Leu Ile Thr Tyr Pro Ser Tyr Lys
            20                  25                  30

Thr Tyr Ile Arg Arg Val Arg Leu Ser Glu Val Arg Thr Thr Leu Leu
        35                  40                  45

His Asn Ala Gln Thr Met Glu Arg Tyr Tyr Arg Gln Lys Gly Thr Phe
    50                  55                  60

Lys Thr Tyr Asp Lys Asn Lys Leu Lys Gln Asn Lys Tyr Phe Asn Val
65                  70                  75                  80

Thr Leu Ser Lys Val Ser Pro Asp His Phe Thr Leu Gln Ala Asp Pro
                85                  90                  95

Asn Pro Thr Thr Asn Asp Gly Glu Thr Cys Val Val Thr Leu Asn Asp
            100                 105                 110

Gly Gly Thr Ile Ala Ala Ser Gly Thr Asn Gln Ser Cys Pro Gly Phe
        115                 120                 125

Asp

<210> SEQ ID NO 14
<211> LENGTH: 162
<212> TYPE: PRT
<213> ORGANISM: Neisseria meningitidis

<400> SEQUENCE: 14

Met Met Ser Asn Lys Met Glu Gln Lys Gly Phe Thr Leu Ile Glu Met
1               5                   10                  15

Met Ile Val Val Ala Ile Leu Gly Ile Ile Ser Val Ile Ala Ile Pro
            20                  25                  30

Ser Tyr Gln Ser Tyr Ile Glu Lys Gly Tyr Gln Ser Gln Leu Tyr Thr
        35                  40                  45

Glu Met Val Gly Ile Asn Asn Ile Ser Lys Gln Phe Ile Leu Lys Asn
    50                  55                  60

Pro Leu Asp Asp Asn Gln Thr Ile Lys Ser Lys Leu Glu Arg Phe Val
65                  70                  75                  80

Ser Gly Tyr Lys Met Asn Pro Lys Ile Ala Glu Lys Tyr Asn Val Ser
                85                  90                  95

Val His Phe Val Asn Lys Glu Lys Pro Arg Ala Tyr Ser Leu Val Gly
            100                 105                 110

Val Pro Lys Thr Gly Thr Gly Tyr Thr Leu Ser Val Trp Met Asn Ser
        115                 120                 125

Val Gly Asp Gly Tyr Lys Cys Arg Asp Ala Ala Ser Ala Arg Ala His
    130                 135                 140

Leu Glu Thr Leu Ser Ser Asp Val Gly Cys Glu Ala Phe Ser Asn Arg
145                 150                 155                 160

Lys Lys

<210> SEQ ID NO 15
```

<211> LENGTH: 1025
<212> TYPE: PRT
<213> ORGANISM: Neisseria meningitidis

<400> SEQUENCE: 15

```
Met Asn Lys Thr Leu Lys Arg Gln Val Phe Arg His Thr Ala Leu Tyr
1               5                   10                  15

Ala Ala Ile Leu Met Phe Ser His Thr Gly Gly Gly Ala Gln Ala
            20                  25                  30

Gln Thr Ser Lys Tyr Ala Ile Met Asn Glu Arg Asn Gln Leu Glu
        35                  40                  45

Val Lys Gln Glu Gly Ser Tyr Ser Thr Leu Arg Glu Lys Asp Arg Glu
50                  55                  60

Arg Lys Phe Asp Phe Asn Ala Asn Arg Gly Gly Gly Ser Val Phe
65              70                  75                  80

Phe Asp Asn Thr Asp Thr Leu Val Ser Arg Gln Ser Gly Thr Ala Val
                85                  90                  95

Phe Gly Thr Ala Thr Tyr Leu Pro Pro Tyr Gly Lys Val Ser Gly Phe
            100                 105                 110

Asp Ala Asp Gly Leu Asn Lys Arg Gly Asn Ala Ala Gly Trp Ile Arg
        115                 120                 125

Thr Thr Arg Ile Ala Leu Ala Gly Tyr Ser Tyr Lys Gly Val Val Cys
130                 135                 140

Arg Ser Gly Thr Gly Cys Pro Lys Leu Val Tyr Lys Thr Arg Phe Ser
145                 150                 155                 160

Phe Asp Asn Pro Asp Leu Val Lys Asn Ala Gly Arg Leu Asp Arg His
                165                 170                 175

Thr Asp Pro Ser Arg Glu Asn Ser Pro Ile Tyr Lys Leu Lys Asp Tyr
            180                 185                 190

Pro Trp Leu Gly Val Ser Phe Asn Leu Gly Ala Glu Gly Thr Thr Lys
        195                 200                 205

Asp Gly Lys Thr Ile Asn Lys Leu Val Ser Ser Phe Asp Glu Lys Asn
210                 215                 220

Ser Ser Asn Asn Asn Leu Val Tyr Thr Thr Glu Gly Arg Asp Ile Ser
225                 230                 235                 240

Leu Gly Asp Trp Gln Arg Glu Lys Thr Ala Met Ala Tyr Tyr Leu Asn
                245                 250                 255

Ala Lys Leu His Leu Leu Asp Lys Lys Gly Ile Lys Asp Ile Thr Asn
            260                 265                 270

Lys Thr Val Gln Leu Gly Val Leu Arg Pro Ser Ile Asp Val Arg Leu
        275                 280                 285

Gln Arg Asn Thr Gly Leu Thr Gly Leu Leu Asn Phe Trp Ala Ser Trp
290                 295                 300

Asp Ile Lys Asp Asn Gly Gln Ile Pro Val Lys Leu Gly Leu Pro Glu
305                 310                 315                 320

Val Lys Ala Gly Arg Cys Ile Asn Ala Asn Pro Asn Lys Ser Thr
                325                 330                 335

Lys Ala Pro Ser Pro Ala Leu Thr Ala Pro Ala Leu Trp Phe Gly Pro
            340                 345                 350

Val Gln Asn Gly Lys Met Glu Met Tyr Ser Ala Ser Val Ser Thr Tyr
        355                 360                 365

Pro Asp Ser Ser Ser Arg Ile Phe Leu Gln Asn Leu Lys Arg Lys
370                 375                 380

Asn Asp Pro Asn Lys Pro Gly Arg Tyr Ser Leu Ala Thr Leu Asn Lys
```

```
385                 390                 395                 400
Ser Asp Ile Glu Ser Arg Glu Pro Thr Phe Thr Gly Arg Gln Thr Val
                405                 410                 415
Ile Arg Leu Asp Lys Gly Val His Gln Ile Lys Leu Lys Gly Asn Glu
                420                 425                 430
Val Glu Gly Phe Lys Gly Asn Asn Gly Asn Asp Thr Phe Gly Ile Val
                435                 440                 445
Ser Glu Gly Ser Phe Met Pro Asp Asp Ser Glu Trp Lys Lys Val Leu
    450                 455                 460
Leu Pro Trp Thr Val Arg Gly Ser Ala Asp Asp Asn Arg Phe Lys Ser
465                 470                 475                 480
Ile Asn Gln Glu Ser Ser Lys Tyr Ser Gln Arg Tyr Arg Ile Arg Asp
                485                 490                 495
Asn Asn Gly Asn Arg Asn Leu Gly Asp Ile Val Asn Ser Pro Ile Val
                500                 505                 510
Ala Val Gly Glu Tyr Leu Ala Thr Ser Ala Asn Asp Gly Met Val His
                515                 520                 525
Ile Phe Lys Lys Asn Gly Gly Asp Asp Arg Asn Tyr Ser Leu Lys
    530                 535                 540
Leu Ser Tyr Ile Pro Gly Thr Met Pro Arg Lys Asp Ile Gln Asn Thr
545                 550                 555                 560
Glu Ser Thr Leu Ala Lys Glu Leu Arg Thr Phe Ala Glu Lys Gly Tyr
                565                 570                 575
Val Gly Asp Arg Tyr Gly Val Asp Gly Gly Phe Val Leu Arg Glu Val
                580                 585                 590
Glu Leu Ser Gly Lys Lys His Val Phe Met Phe Gly Ala Met Gly Phe
                595                 600                 605
Gly Gly Arg Gly Ala Tyr Ala Leu Asp Leu Thr Lys Ala Asp Ser Asn
                610                 615                 620
Asn Pro Thr Ala Val Ser Leu Phe Asp Val Lys Asn Asp Lys Asn Ser
625                 630                 635                 640
Asn Asn Gly Val Gln Leu Gly Tyr Thr Val Gly Thr Pro Gln Ile Gly
                645                 650                 655
Lys Thr His Asp Gly Lys Tyr Ala Ala Phe Leu Ala Ser Gly Tyr Ala
                660                 665                 670
Thr Lys Glu Ile Thr Ser Asn Asp Asn Lys Thr Ala Leu Tyr Val Tyr
                675                 680                 685
Asp Leu Glu Ser Asn Gly Thr Leu Ile Lys Lys Ile Glu Val Pro Gly
    690                 695                 700
Gly Lys Gly Gly Leu Ser Ser Pro Thr Leu Val Asp Lys Asp Leu Asp
705                 710                 715                 720
Gly Thr Val Asp Ile Ala Tyr Ala Gly Asp Arg Gly Gly Lys Met Tyr
                725                 730                 735
Arg Phe Asp Leu Ser Gly Asn Asn Leu Asn Ser Trp Thr Val Arg Thr
                740                 745                 750
Ile Phe Glu Gly Thr Lys Pro Ile Thr Ser Ala Pro Ala Ile Ser Gln
                755                 760                 765
Leu Lys Asp Lys Arg Val Val Ile Phe Gly Thr Gly Ser Asp Leu Ser
    770                 775                 780
Glu Asp Asp Val Asp Asn Asn Asp Met Gln Ser Ile Tyr Gly Ile Phe
785                 790                 795                 800
Asp Asn Asp Thr Asp Thr Gly Val Ala Lys Asp Gly Gln Gly Asn Gly
                805                 810                 815
```

Leu Leu Glu Gln Val Leu Ser Glu Glu Asn Lys Thr Leu Phe Leu Thr
            820                 825                 830

Asp Tyr Lys Arg Ser Asp Gly Ser Gly Ser Lys Gly Trp Val Val Lys
        835                 840                 845

Leu Lys Glu Gly Gln Arg Val Thr Val Lys Pro Thr Val Val Leu Arg
850                 855                 860

Thr Ala Phe Val Thr Ile His Lys Tyr Thr Gly Thr Asp Lys Cys Gly
865                 870                 875                 880

Ala Glu Thr Ala Ile Leu Gly Ile Asn Thr Ala Asp Gly Gly Lys Leu
                885                 890                 895

Thr Lys Lys Ser Ala Arg Pro Ile Val Pro Ala Ala Asn Thr Ala Val
            900                 905                 910

Ala Gln Tyr Ser Gly His Lys Gln Thr Ala Lys Gly Lys Ser Ile Pro
        915                 920                 925

Ile Gly Cys Met Trp Lys Asn Asn Glu Thr Val Cys Pro Asn Gly Tyr
    930                 935                 940

Val Tyr Asp Lys Pro Val Asn Val Arg Tyr Leu Asp Glu Lys Lys Thr
945                 950                 955                 960

Asp Gly Phe Ser Thr Thr Ala Asp Gly Asp Ala Gly Ser Gly Ile
                965                 970                 975

Asp Pro Asp Gly Lys Arg Ala Gly Lys Asn Asn Arg Cys Phe Ser Gln
            980                 985                 990

Lys Gly Val Arg Thr Leu Leu Met Asn Asp Leu Asp Ser Leu Asp Ile
        995                 1000                1005

Thr Gly Pro Thr Cys Gly Met Lys Arg Ile Ser Trp Arg Glu Val
    1010                1015                1020

Phe Phe
    1025

<210> SEQ ID NO 16
<211> LENGTH: 149
<212> TYPE: PRT
<213> ORGANISM: Neisseria meningitidis

<400> SEQUENCE: 16

Met Thr Asp Asn Arg Gly Phe Thr Leu Val Glu Leu Ile Ser Val Val
1               5                   10                  15

Leu Ile Leu Ser Val Leu Ala Leu Ile Val Tyr Pro Ser Tyr Arg Asn
            20                  25                  30

Tyr Val Glu Lys Ala Lys Ile Asn Ala Val Arg Ala Ala Leu Leu Glu
        35                  40                  45

Asn Ala His Phe Met Glu Lys Phe Tyr Leu Gln Asn Gly Arg Phe Lys
    50                  55                  60

Gln Thr Ser Thr Lys Trp Pro Ser Leu Pro Ile Lys Glu Ala Glu Gly
65                  70                  75                  80

Phe Cys Ile Arg Leu Asn Gly Ile Ala Arg Gly Ala Leu Asp Ser Lys
                85                  90                  95

Phe Met Leu Lys Ala Val Ala Ile Asp Lys Asp Lys Asn Pro Phe Ile
            100                 105                 110

Ile Lys Met Asn Glu Asn Leu Val Thr Phe Ile Cys Lys Lys Ser Ala
        115                 120                 125

Ser Ser Cys Ser Asp Gly Leu Asp Tyr Phe Lys Gly Asn Asp Lys Asp
    130                 135                 140

Cys Lys Leu Phe Lys
145

<210> SEQ ID NO 17
<211> LENGTH: 280
<212> TYPE: PRT
<213> ORGANISM: Neisseria meningitidis

<400> SEQUENCE: 17

Met Thr Arg Ser Lys Pro Val Asn Arg Thr Ala Phe Cys Cys Leu Ser
1               5                   10                  15

Leu Thr Ala Ala Leu Ile Leu Thr Ala Cys Ser Ser Gly Gly Gly Gly
            20                  25                  30

Val Ala Ala Asp Ile Gly Ala Val Leu Ala Asp Ala Leu Thr Ala Pro
        35                  40                  45

Leu Asp His Lys Asp Lys Ser Leu Gln Ser Leu Thr Leu Asp Gln Ser
    50                  55                  60

Val Arg Lys Asn Glu Lys Leu Lys Leu Ala Ala Gln Gly Ala Glu Lys
65                  70                  75                  80

Thr Tyr Gly Asn Gly Asp Ser Leu Asn Thr Gly Lys Leu Lys Asn Asp
                85                  90                  95

Lys Val Ser Arg Phe Asp Phe Ile Arg Gln Ile Glu Val Asp Gly Gln
            100                 105                 110

Leu Ile Thr Leu Glu Ser Gly Glu Phe Gln Val Tyr Lys Gln Ser His
        115                 120                 125

Ser Ala Leu Thr Ala Leu Gln Thr Glu Gln Val Gln Asp Ser Glu His
    130                 135                 140

Ser Gly Lys Met Val Ala Lys Arg Gln Phe Arg Ile Gly Asp Ile Ala
145                 150                 155                 160

Gly Glu His Thr Ser Phe Asp Lys Leu Pro Glu Gly Gly Arg Ala Thr
                165                 170                 175

Tyr Arg Gly Thr Ala Phe Gly Ser Asp Asp Ala Ser Gly Lys Leu Thr
            180                 185                 190

Tyr Thr Ile Asp Phe Ala Ala Lys Gln Gly His Gly Lys Ile Glu His
        195                 200                 205

Leu Lys Ser Pro Glu Leu Asn Val Asp Leu Ala Ala Ser Asp Ile Lys
    210                 215                 220

Pro Asp Lys Lys Arg His Ala Val Ile Ser Gly Ser Val Leu Tyr Asn
225                 230                 235                 240

Gln Ala Glu Lys Gly Ser Tyr Ser Leu Gly Ile Phe Gly Gly Gln Ala
                245                 250                 255

Gln Glu Val Ala Gly Ser Ala Glu Val Glu Thr Ala Asn Gly Ile Arg
            260                 265                 270

His Ile Gly Leu Ala Ala Lys Gln
        275                 280

<210> SEQ ID NO 18
<211> LENGTH: 279
<212> TYPE: PRT
<213> ORGANISM: Neisseria meningitidis

<400> SEQUENCE: 18

Met Thr Arg Ser Lys Pro Val Asn Arg Thr Ala Phe Cys Cys Leu Ser
1               5                   10                  15

Leu Thr Ala Ala Leu Ile Leu Thr Ala Cys Ser Ser Gly Gly Gly Gly
            20                  25                  30

Val Ala Ala Asp Ile Gly Ala Gly Leu Ala Asp Ala Leu Thr Ala Pro

```
            35                  40                  45
Leu Asp His Lys Asp Lys Ser Leu Gln Ser Leu Thr Leu Asp Gln Ser
 50                  55                  60

Val Arg Lys Asn Glu Lys Leu Lys Leu Ala Ala Gln Gly Ala Glu Lys
 65                  70                  75                  80

Thr Tyr Gly Asn Gly Asp Ser Leu Asn Thr Gly Lys Leu Lys Asn Asp
                 85                  90                  95

Lys Val Ser Arg Phe Asp Phe Ile Arg Gln Ile Glu Val Asp Gly Gln
                100                 105                 110

Leu Ile Thr Leu Glu Ser Gly Glu Phe Gln Ile Tyr Lys Gln Asp His
                115                 120                 125

Ser Ala Val Val Ala Leu Gln Ile Glu Lys Ile Asn Asn Pro Asp Lys
                130                 135                 140

Ile Asp Ser Leu Ile Asn Gln Arg Ser Phe Leu Val Ser Gly Leu Gly
145                 150                 155                 160

Gly Glu His Thr Ala Phe Asn Gln Leu Pro Gly Gly Lys Ala Glu Tyr
                165                 170                 175

His Gly Lys Ala Phe Ser Ser Asp Asp Ala Gly Gly Lys Leu Thr Tyr
                180                 185                 190

Thr Ile Asp Phe Ala Ala Lys Gln Gly His Gly Lys Ile Glu His Leu
                195                 200                 205

Lys Thr Pro Glu Gln Asn Val Glu Leu Ala Ala Ala Glu Leu Lys Ala
                210                 215                 220

Asp Glu Lys Ser His Ala Val Ile Leu Gly Asp Thr Arg Tyr Gly Ser
225                 230                 235                 240

Glu Glu Lys Gly Thr Tyr His Leu Ala Leu Phe Gly Asp Arg Ala Gln
                245                 250                 255

Glu Ile Ala Gly Ser Ala Thr Val Lys Ile Gly Glu Lys Val His Glu
                260                 265                 270

Ile Gly Ile Ala Gly Lys Gln
                275

<210> SEQ ID NO 19
<211> LENGTH: 395
<212> TYPE: PRT
<213> ORGANISM: Neisseria meningitidis

<400> SEQUENCE: 19

Met Arg Lys Lys Leu Thr Ala Leu Val Leu Ser Ala Leu Pro Leu Ala
 1               5                  10                  15

Ala Val Ala Asp Val Ser Leu Tyr Gly Glu Ile Lys Ala Gly Val Glu
                 20                  25                  30

Gly Arg Asn Tyr Gln Leu Gln Leu Thr Glu Ala Gln Ala Ala Asn Gly
                 35                  40                  45

Gly Ala Ser Gly Gln Val Lys Val Thr Lys Val Thr Lys Ala Lys Ser
 50                  55                  60

Arg Ile Arg Thr Lys Ile Ser Asp Phe Gly Ser Phe Ile Gly Phe Lys
 65                  70                  75                  80

Gly Ser Glu Asp Leu Gly Glu Gly Leu Lys Ala Val Trp Gln Leu Glu
                 85                  90                  95

Gln Asp Val Ser Val Ala Gly Gly Ala Thr Gln Trp Gly Asn Arg
                100                 105                 110

Glu Ser Phe Ile Gly Leu Ala Gly Glu Phe Gly Thr Leu Arg Ala Gly
                115                 120                 125
```

```
Arg Val Ala Asn Gln Phe Asp Asp Ala Ser Gln Ala Ile Asp Pro Trp
130                 135                 140

Asp Ser Asn Asn Asp Val Ala Ser Gln Leu Gly Ile Phe Lys Arg His
145                 150                 155                 160

Asp Asp Met Pro Val Ser Val Arg Tyr Asp Ser Pro Glu Phe Ser Gly
                165                 170                 175

Phe Ser Gly Ser Val Gln Phe Val Pro Ala Gln Asn Ser Lys Ser Ala
            180                 185                 190

Tyr Lys Pro Ala Tyr Trp Thr Thr Val Asn Thr Gly Ser Ala Thr Thr
        195                 200                 205

Thr Thr Phe Val Pro Ala Val Val Gly Lys Pro Gly Ser Asp Val Tyr
210                 215                 220

Tyr Ala Gly Leu Asn Tyr Lys Asn Gly Phe Ala Gly Asn Tyr Ala
225                 230                 235                 240

Phe Lys Tyr Ala Arg His Ala Asn Val Gly Arg Asp Ala Phe Glu Leu
                245                 250                 255

Phe Leu Leu Gly Ser Gly Ser Asp Gln Ala Lys Gly Thr Asp Pro Leu
            260                 265                 270

Lys Asn His Gln Val His Arg Leu Thr Gly Gly Tyr Glu Glu Gly Gly
        275                 280                 285

Leu Asn Leu Ala Leu Ala Ala Gln Leu Asp Leu Ser Glu Asn Gly Asp
290                 295                 300

Lys Thr Lys Asn Ser Thr Thr Glu Ile Ala Ala Thr Ala Ser Tyr Arg
305                 310                 315                 320

Phe Gly Asn Ala Val Pro Arg Ile Ser Tyr Ala His Gly Phe Asp Phe
                325                 330                 335

Ile Glu Arg Gly Lys Lys Gly Glu Asn Thr Ser Tyr Asp Gln Ile Ile
            340                 345                 350

Ala Gly Val Asp Tyr Asp Phe Ser Lys Arg Thr Ser Ala Ile Val Ser
        355                 360                 365

Gly Ala Trp Leu Lys Arg Asn Thr Gly Ile Gly Asn Tyr Thr Gln Ile
370                 375                 380

Asn Ala Ala Ser Val Gly Leu Arg His Lys Phe
385                 390                 395

<210> SEQ ID NO 20
<211> LENGTH: 497
<212> TYPE: PRT
<213> ORGANISM: Neisseria meningitidis

<400> SEQUENCE: 20

Met Phe Lys Arg Ser Val Ile Ala Met Ala Cys Ile Val Ala Leu Ser
1               5                   10                  15

Ala Cys Gly Gly Gly Gly Gly Ser Pro Asp Val Lys Ser Ala Asp
                20                  25                  30

Thr Leu Ser Lys Pro Ala Ala Pro Val Val Thr Glu Asp Val Gly Glu
            35                  40                  45

Glu Val Leu Pro Lys Glu Lys Lys Asp Glu Glu Ala Val Ser Gly Ala
        50                  55                  60

Pro Gln Ala Asp Thr Gln Asp Ala Thr Ala Gly Lys Gly Gly Gln Asp
65                  70                  75                  80

Met Ala Ala Val Ser Ala Glu Asn Thr Gly Asn Gly Gly Ala Ala Thr
                85                  90                  95

Thr Asp Asn Pro Glu Asn Lys Asp Glu Gly Pro Gln Asn Asp Met Pro
            100                 105                 110
```

Gln Asn Ala Ala Asp Thr Asp Ser Ser Thr Pro Asn His Thr Pro Ala
            115                 120                 125

Pro Asn Met Pro Thr Arg Asp Met Gly Asn Gln Ala Pro Asp Ala Gly
130                 135                 140

Glu Ser Ala Gln Pro Ala Asn Gln Pro Asp Met Ala Asn Ala Ala Asp
145                 150                 155                 160

Gly Met Gln Gly Asp Asp Pro Ser Ala Gly Glu Asn Ala Gly Asn Thr
            165                 170                 175

Ala Asp Gln Ala Ala Asn Gln Ala Glu Asn Asn Gln Val Gly Gly Ser
            180                 185                 190

Gln Asn Pro Ala Ser Ser Thr Asn Pro Asn Ala Thr Asn Gly Gly Ser
            195                 200                 205

Asp Phe Gly Arg Ile Asn Val Ala Asn Gly Ile Lys Leu Asp Ser Gly
            210                 215                 220

Ser Glu Asn Val Thr Leu Thr His Cys Lys Asp Lys Val Cys Asp Arg
225                 230                 235                 240

Asp Phe Leu Asp Glu Glu Ala Pro Pro Lys Ser Glu Phe Glu Lys Leu
            245                 250                 255

Ser Asp Glu Glu Lys Ile Asn Lys Tyr Lys Lys Asp Glu Gln Arg Glu
            260                 265                 270

Asn Phe Val Gly Leu Val Ala Asp Arg Val Glu Lys Asn Gly Thr Asn
            275                 280                 285

Lys Tyr Val Ile Ile Tyr Lys Asp Lys Ser Ala Ser Ser Ser Ser Ala
            290                 295                 300

Arg Phe Arg Arg Ser Ala Arg Ser Arg Arg Ser Leu Pro Ala Glu Met
305                 310                 315                 320

Pro Leu Ile Pro Val Asn Gln Ala Asp Thr Leu Ile Val Asp Gly Glu
            325                 330                 335

Ala Val Ser Leu Thr Gly His Ser Gly Asn Ile Phe Ala Pro Glu Gly
            340                 345                 350

Asn Tyr Arg Tyr Leu Thr Tyr Gly Ala Glu Lys Leu Ser Gly Gly Ser
            355                 360                 365

Tyr Ala Leu Ser Val Gln Gly Glu Pro Ala Lys Gly Glu Met Leu Ala
            370                 375                 380

Gly Thr Ala Val Tyr Asn Gly Glu Val Leu His Phe His Met Glu Asn
385                 390                 395                 400

Gly Arg Pro Ser Pro Ser Gly Gly Arg Phe Ala Ala Lys Val Asp Phe
            405                 410                 415

Gly Ser Lys Ser Val Asp Gly Ile Ile Asp Ser Gly Asp Asp Leu His
            420                 425                 430

Met Gly Thr Gln Lys Phe Lys Ala Val Ile Asp Gly Asn Gly Phe Lys
            435                 440                 445

Gly Thr Trp Thr Glu Asn Gly Gly Asp Val Ser Gly Arg Phe Tyr
450                 455                 460

Gly Pro Ala Gly Glu Glu Val Ala Gly Lys Tyr Ser Tyr Arg Pro Thr
465                 470                 475                 480

Asp Ala Glu Lys Gly Gly Phe Gly Val Phe Ala Gly Lys Lys Glu Gln
            485                 490                 495

Asp

<210> SEQ ID NO 21
<211> LENGTH: 364
<212> TYPE: PRT

<213> ORGANISM: Neisseria meningitidis

<400> SEQUENCE: 21

```
Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
            20                  25                  30

Lys Lys Ala Ala Thr Val Ala Ile Val Ala Ala Tyr Asn Asn Gly Gln
        35                  40                  45

Glu Ile Asn Gly Phe Lys Ala Gly Glu Thr Ile Tyr Asp Ile Gly Glu
    50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
    130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Ala Gly Thr Ala
225                 230                 235                 240

Asn Thr Ala Ala Asp Lys Ala Glu Ala Val Ala Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360
```

<210> SEQ ID NO 22
<211> LENGTH: 313
<212> TYPE: PRT
<213> ORGANISM: Neisseria meningitidis

<400> SEQUENCE: 22

Met Lys Thr Leu Leu Leu Ile Pro Leu Val Leu Thr Ala Cys Gly
1               5                   10                  15

Thr Leu Thr Gly Ile Pro Ala His Gly Gly Gly Lys Arg Phe Ala Val
            20                  25                  30

Glu Gln Glu Leu Val Ala Ala Ser Ser Arg Ala Ala Val Lys Glu Met
        35                  40                  45

Asp Leu Ser Ala Leu Lys Gly Arg Lys Ala Ala Leu Tyr Val Ser Val
    50                  55                  60

Met Gly Asp Gln Gly Ser Gly Asn Ile Ser Gly Gly Arg Tyr Ser Ile
65                  70                  75                  80

Asp Ala Leu Ile Arg Gly Gly Tyr His Asn Asn Pro Glu Ser Ala Thr
                85                  90                  95

Gln Tyr Ser Tyr Pro Ala Tyr Asp Thr Thr Ala Thr Thr Lys Ser Asp
            100                 105                 110

Ala Leu Ser Ser Val Thr Thr Ser Thr Ser Leu Leu Asn Ala Pro Ala
        115                 120                 125

Ala Ala Leu Thr Lys Asn Ser Gly Arg Lys Gly Glu Arg Ser Ala Gly
    130                 135                 140

Leu Ser Val Asn Gly Thr Gly Asp Tyr Arg Asn Glu Thr Leu Leu Ala
145                 150                 155                 160

Asn Pro Arg Asp Val Ser Phe Leu Thr Asn Leu Ile Gln Thr Val Phe
                165                 170                 175

Tyr Leu Arg Gly Ile Glu Val Val Pro Pro Glu Tyr Ala Asp Thr Asp
            180                 185                 190

Val Phe Val Thr Val Asp Val Phe Gly Thr Val Arg Ser Arg Thr Glu
        195                 200                 205

Leu His Leu Tyr Asn Ala Glu Thr Leu Lys Ala Gln Thr Lys Leu Glu
    210                 215                 220

Tyr Phe Ala Val Asp Arg Asp Ser Arg Lys Leu Leu Ile Ala Pro Lys
225                 230                 235                 240

Thr Ala Ala Tyr Glu Ser Gln Tyr Gln Glu Gln Tyr Ala Leu Trp Met
                245                 250                 255

Gly Pro Tyr Ser Val Gly Lys Thr Val Lys Ala Ser Asp Arg Leu Met
            260                 265                 270

Val Asp Phe Ser Asp Ile Thr Pro Tyr Gly Asp Thr Thr Ala Gln Asn
        275                 280                 285

Arg Pro Asp Phe Lys Gln Asn Asn Gly Lys Lys Pro Asp Val Gly Asn
    290                 295                 300

Glu Val Ile Arg Arg Lys Gly Gly
305                 310

<210> SEQ ID NO 23
<211> LENGTH: 313
<212> TYPE: PRT
<213> ORGANISM: Neisseria meningitidis

<400> SEQUENCE: 23

Met Lys Thr Leu Leu Leu Ile Pro Leu Val Leu Thr Ala Cys Gly
1               5                   10                  15

Thr Leu Thr Gly Ile Pro Ala His Gly Gly Gly Lys Arg Phe Ala Val
            20                  25                  30

Glu Gln Glu Leu Val Ala Ala Ser Ser Arg Ala Ala Val Lys Glu Met
        35                  40                  45

```
Asp Leu Ser Ala Leu Lys Gly Arg Lys Ala Ala Leu Tyr Val Ser Val
 50                  55                  60

Met Gly Asp Gln Gly Ser Gly Asn Ile Ser Gly Gly Arg Tyr Ser Ile
 65                  70                  75                  80

Asp Ala Leu Ile Arg Gly Gly Tyr His Asn Asn Pro Glu Ser Thr Thr
                 85                  90                  95

Gln Tyr Ser Tyr Pro Ala Tyr Asp Thr Thr Ala Thr Thr Lys Ala Asp
                100                 105                 110

Ala Leu Ser Ser Val Thr Thr Ser Thr Leu Leu Asn Ala Pro Ala
             115                 120                 125

Ala Ala Leu Thr Lys Asn Ser Gly Arg Lys Gly Glu Arg Ser Ala Gly
130                 135                 140

Leu Ser Val Asn Gly Thr Gly Asp Tyr Arg Asn Glu Thr Leu Leu Ala
145                 150                 155                 160

Asn Pro Arg Asp Val Ser Phe Leu Thr Asn Leu Ile Gln Thr Val Phe
                165                 170                 175

Tyr Leu Arg Gly Ile Glu Val Val Pro Pro Glu Tyr Ala Asp Thr Asp
                180                 185                 190

Val Phe Val Thr Val Asp Val Phe Gly Thr Val Arg Ser Arg Thr Glu
                195                 200                 205

Leu His Leu Tyr Asn Ala Glu Thr Leu Lys Ala Gln Thr Lys Leu Glu
210                 215                 220

Tyr Phe Ala Val Asp Arg Asp Ser Arg Lys Leu Leu Ile Ala Pro Lys
225                 230                 235                 240

Thr Ala Ala Tyr Glu Ser Gln Tyr Gln Glu Gln Tyr Ala Leu Trp Met
                245                 250                 255

Gly Pro Tyr Ser Val Gly Lys Thr Val Lys Ala Ser Asp Arg Leu Met
                260                 265                 270

Val Asp Phe Ser Asp Ile Thr Pro Tyr Gly Asp Thr Thr Ala Gln Asn
                275                 280                 285

Arg Pro Asp Phe Lys Gln Asn Asn Gly Lys Asn Pro Asp Val Gly Asn
                290                 295                 300

Glu Val Ile Arg Arg Lys Gly Gly
305                 310

<210> SEQ ID NO 24
<211> LENGTH: 320
<212> TYPE: PRT
<213> ORGANISM: Neisseria meningitidis

<400> SEQUENCE: 24

Met Gln Ala Arg Leu Leu Ile Pro Ile Leu Phe Ser Val Phe Ile Leu
 1               5                   10                  15

Ser Ala Cys Gly Thr Leu Thr Gly Ile Pro Ser His Gly Gly Gly Lys
                 20                  25                  30

Arg Phe Ala Val Glu Gln Glu Leu Val Ala Ala Ser Ala Arg Ala Ala
             35                  40                  45

Val Lys Asp Met Asp Leu Gln Ala Leu His Gly Arg Lys Val Ala Leu
 50                  55                  60

Tyr Ile Ala Thr Met Gly Asp Gln Gly Ser Gly Ser Leu Thr Gly Gly
 65                  70                  75                  80

Arg Tyr Ser Ile Asp Ala Leu Ile Arg Gly Glu Tyr Ile Asn Ser Pro
                 85                  90                  95

Ala Val Arg Thr Asp Tyr Thr Tyr Pro Arg Tyr Glu Thr Thr Ala Glu
                100                 105                 110
```

```
Thr Thr Ser Gly Gly Leu Thr Gly Leu Thr Thr Ser Leu Ser Thr Leu
        115                 120                 125

Asn Ala Pro Ala Arg Ser Arg Thr Gln Ser Asp Gly Ser Gly Ser Arg
130                 135                 140

Ser Ser Leu Gly Leu Asn Ile Gly Gly Met Gly Asp Tyr Arg Asn Glu
145                 150                 155                 160

Thr Leu Thr Thr Asn Pro Arg Asp Thr Ala Phe Leu Ser His Leu Val
            165                 170                 175

Gln Thr Val Phe Phe Leu Arg Gly Ile Asp Val Val Ser Pro Ala Asn
        180                 185                 190

Ala Asp Thr Asp Val Phe Ile Asn Ile Asp Val Phe Gly Thr Ile Arg
        195                 200                 205

Asn Arg Thr Glu Met His Leu Tyr Asn Ala Glu Thr Leu Lys Ala Gln
        210                 215                 220

Thr Lys Leu Glu Tyr Phe Ala Val Asp Arg Thr Asn Lys Lys Leu Leu
225                 230                 235                 240

Ile Lys Pro Lys Thr Asn Ala Phe Glu Ala Val Tyr Lys Glu Asn Tyr
            245                 250                 255

Ala Leu Trp Met Gly Pro Tyr Lys Val Ser Lys Gly Ile Lys Pro Thr
        260                 265                 270

Glu Gly Leu Met Val Asp Phe Ser Asp Ile Arg Pro Tyr Gly Asn His
        275                 280                 285

Thr Gly Asn Ser Ala Pro Ser Val Glu Thr Asp Asn Ser His Glu Gly
        290                 295                 300

Tyr Gly Tyr Ser Asp Glu Val Val Arg Gln His Arg Gln Gly Gln Pro
305                 310                 315                 320

<210> SEQ ID NO 25
<211> LENGTH: 174
<212> TYPE: PRT
<213> ORGANISM: Neisseria meningitidis

<400> SEQUENCE: 25

Met Lys Lys Ala Leu Ala Ala Leu Ile Ala Leu Ala Leu Pro Ala Ala
1               5                   10                  15

Ala Leu Ala Glu Gly Ala Ser Gly Phe Tyr Val Gln Ala Asp Ala Ala
            20                  25                  30

His Ala Lys Ala Ser Ser Ser Leu Gly Ser Ala Lys Gly Phe Ser Pro
        35                  40                  45

Arg Ile Ser Ala Gly Tyr Arg Ile Asn Asp Leu Arg Phe Ala Val Asp
50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
            85                  90                  95

Val Lys Pro Tyr Leu Gly Ala Arg Leu Ser Leu Asn Arg Ala Ser Val
        100                 105                 110

Asp Leu Gly Gly Ser Asp Ser Phe Ser Gln Thr Ser Thr Gly Leu Gly
        115                 120                 125

Val Leu Ala Gly Val Ser Tyr Ala Val Thr Pro Asn Val Asp Leu Asp
        130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Val Gly Val Arg Val Lys Phe
```

-continued

```
                165                 170
```

<210> SEQ ID NO 26
<211> LENGTH: 792
<212> TYPE: PRT
<213> ORGANISM: Neisseria meningitidis

<400> SEQUENCE: 26

```
Met Lys Pro Leu Gln Met Leu Pro Ile Ala Ala Leu Val Gly Ser Ile
1               5                   10                  15

Phe Gly Asn Pro Val Phe Ala Ala Asp Glu Ala Ala Thr Glu Thr Thr
            20                  25                  30

Pro Val Lys Ala Glu Val Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Asp Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Leu Pro Glu Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Lys
    210                 215                 220

Arg Gly Tyr Pro Val Glu Gly Ala Gly Ser Gly Ala Asn Ile Arg Gly
225                 230                 235                 240

Ser Ala Arg Gly Ile Pro Asp Pro Ser Gln His Lys Tyr His Ser Phe
                245                 250                 255

Leu Gly Lys Ile Ala Tyr Gln Ile Asn Asp Asn His Arg Ile Gly Ala
            260                 265                 270

Ser Leu Asn Gly Gln Gln Gly His Asn Tyr Thr Val Glu Glu Ser Tyr
        275                 280                 285

Asn Leu Leu Ala Ser Tyr Trp Arg Glu Ala Asp Asp Val Asn Arg Arg
    290                 295                 300

Arg Asn Thr Asn Leu Phe Tyr Glu Trp Thr Pro Glu Ser Asp Arg Leu
305                 310                 315                 320

Ser Met Val Lys Ala Asp Val Asp Tyr Gln Lys Thr Lys Val Ser Ala
                325                 330                 335

Val Asn Tyr Lys Gly Ser Phe Pro Ile Glu Asp Ser Ser Thr Leu Thr
            340                 345                 350

Arg Asn Tyr Asn Gln Lys Asp Leu Asp Glu Ile Tyr Asn Arg Ser Met
        355                 360                 365
```

```
Asp Thr Arg Phe Lys Arg Ile Thr Leu Arg Leu Asp Ser His Pro Leu
    370             375             380

Gln Leu Gly Gly Gly Arg His Arg Leu Ser Phe Lys Thr Phe Ala Ser
385             390             395             400

Arg Arg Asp Phe Glu Asn Leu Asn Arg Asp Asp Tyr Tyr Phe Ser Gly
                405             410             415

Arg Val Val Arg Thr Ser Ser Ile Gln His Pro Val Lys Thr Thr
            420             425             430

Asn Tyr Gly Phe Ser Leu Ser Asp Gln Ile Gln Trp Asn Asp Val Phe
        435             440             445

Ser Ser Arg Ala Gly Ile Arg Tyr Asp His Thr Lys Met Thr Pro Gln
450             455             460

Glu Leu Asn Ala Glu Cys His Ala Cys Asp Lys Thr Pro Pro Ala Ala
465             470             475             480

Asn Thr Tyr Lys Gly Trp Ser Gly Phe Val Gly Leu Ala Ala Gln Leu
            485             490             495

Asn Gln Ala Trp Arg Val Gly Tyr Asp Ile Thr Ser Gly Tyr Arg Val
        500             505             510

Pro Asn Ala Ser Glu Val Tyr Phe Thr Tyr Asn His Gly Ser Gly Asn
            515             520             525

Trp Leu Pro Asn Pro Asn Leu Lys Ala Glu Arg Ser Thr Thr His Thr
530             535             540

Leu Ser Leu Gln Gly Arg Ser Glu Lys Gly Thr Leu Asp Ala Asn Leu
545             550             555             560

Tyr Gln Ser Asn Tyr Arg Asn Phe Leu Ser Glu Glu Gln Lys Leu Thr
            565             570             575

Thr Ser Gly Asp Val Ser Cys Thr Gln Met Asn Tyr Tyr Gly Met
        580             585             590

Cys Ser Asn Pro Tyr Ser Glu Lys Leu Glu Trp Gln Met Gln Asn Ile
    595             600             605

Asp Lys Ala Arg Ile Arg Gly Ile Glu Leu Thr Gly Arg Leu Asn Val
    610             615             620

Asp Lys Val Ala Ser Phe Val Pro Glu Gly Trp Lys Leu Phe Gly Ser
625             630             635             640

Leu Gly Tyr Ala Lys Ser Lys Leu Ser Gly Asp Asn Ser Leu Leu Ser
            645             650             655

Thr Gln Pro Leu Lys Val Ile Ala Gly Ile Asp Tyr Glu Ser Pro Ser
        660             665             670

Glu Lys Trp Gly Val Phe Ser Arg Leu Thr Tyr Leu Gly Ala Lys Lys
    675             680             685

Val Lys Asp Ala Gln Tyr Thr Val Tyr Glu Asn Lys Gly Trp Gly Thr
    690             695             700

Pro Leu Gln Lys Lys Val Lys Asp Tyr Pro Trp Leu Asn Lys Ser Ala
705             710             715             720

Tyr Val Phe Asp Met Tyr Gly Phe Tyr Lys Pro Val Lys Asn Leu Thr
                725             730             735

Leu Arg Ala Gly Val Tyr Asn Val Phe Asn Arg Lys Tyr Thr Thr Trp
            740             745             750

Asp Ser Leu Arg Gly Leu Tyr Ser Tyr Ser Thr Thr Asn Ser Val Asp
        755             760             765

Arg Asp Gly Lys Gly Leu Asp Arg Tyr Arg Ala Pro Ser Arg Asn Tyr
770             775             780

Ala Val Ser Leu Glu Trp Lys Phe
```

<210> SEQ ID NO 27
<211> LENGTH: 720
<212> TYPE: PRT
<213> ORGANISM: Neisseria meningitidis

<400> SEQUENCE: 27

Met Asn Asn Pro Leu Val Asn Gln Ala Ala Met Val Leu Pro Val Phe
1               5                   10                  15

Leu Leu Ser Ala Cys Leu Gly Gly Gly Ser Phe Asp Leu Asp Ser
            20                  25                  30

Val Asp Thr Glu Ala Pro Arg Pro Ala Pro Lys Tyr Gln Asp Val Ser
        35                  40                  45

Ser Glu Lys Pro Gln Ala Gln Lys Asp Gln Gly Gly Tyr Gly Phe Ala
    50                  55                  60

Met Arg Phe Lys Arg Arg Asn Trp Tyr Pro Gln Ala Asn Pro Lys Glu
65                  70                  75                  80

Asp Glu Ile Lys Leu Ser Glu Asn Asp Trp Glu Ala Thr Gly Leu Pro
                85                  90                  95

Gly Asn Pro Lys Asn Leu Pro Glu Arg Gln Lys Ser Val Ile Glu Lys
            100                 105                 110

Val Lys Thr Gly Ser Asp Ser Asn Ile Tyr Ser Ser Pro Tyr Leu Thr
        115                 120                 125

Gln Ser Asn His Gln Asn Gly Ser Ala Asn Gln Pro Lys Asn Glu Val
    130                 135                 140

Lys Asp Tyr Lys Glu Phe Lys Tyr Val Tyr Ser Gly Trp Phe Tyr Lys
145                 150                 155                 160

His Ala Lys Leu Glu Ile Ile Lys Glu Asn Asn Leu Ile Lys Gly Ala
                165                 170                 175

Lys Ser Gly Asp Asp Gly Tyr Ile Phe Tyr His Gly Glu Lys Pro Ser
            180                 185                 190

Arg Gln Leu Pro Val Ser Gly Glu Val Thr Tyr Lys Gly Val Trp His
    195                 200                 205

Phe Val Thr Asp Thr Lys Gln Gly Gln Lys Phe Asn Asp Ile Leu Gly
210                 215                 220

Thr Ser Lys Lys Gln Gly Asp Arg Tyr Ser Gly Phe Pro Gly Asp Asp
225                 230                 235                 240

Gly Glu Glu Tyr Ser Asn Lys Asn Glu Ala Thr Leu Gln Gly Ser Gln
                245                 250                 255

Glu Gly Tyr Gly Phe Thr Ser Asn Leu Lys Val Asp Phe Asn Lys Lys
            260                 265                 270

Lys Leu Thr Gly Glu Leu Ile Arg Asn Asn Arg Val Thr Asn Ala Thr
    275                 280                 285

Ala Ser Asp Lys His Thr Thr Gln Tyr Tyr Ser Leu Glu Ala Gln Val
290                 295                 300

Thr Gly Asn Arg Phe Asn Gly Lys Ala Met Ala Thr Asp Lys Pro Gly
305                 310                 315                 320

Asn Gly Glu Thr Lys Gln His Pro Phe Val Ser Asp Ser Ser Ser Leu
                325                 330                 335

Ser Gly Gly Phe Phe Gly Pro Lys Gly Glu Glu Leu Gly Phe Arg Phe
            340                 345                 350

Leu Ser Asp Asp Lys Lys Val Ala Val Val Gly Ser Ala Lys Thr Lys
    355                 360                 365

-continued

```
Asp Lys Asp Ala Asn Gly Asn Thr Glu Ala Ala Ser Gly Gly Thr Gly
    370                 375                 380

Ala Ala Ala Ser Gly Gly Ala Ala Ala Met Pro Ser Glu Asn Gly Lys
385                 390                 395                 400

Leu Thr Thr Val Leu Asp Ala Val Glu Leu Thr Arg Gly Gly Lys Ala
                405                 410                 415

Ile Lys Asn Leu Asp Asn Phe Ser Asn Ala Ala Gln Leu Val Val Asp
            420                 425                 430

Gly Ile Met Ile Pro Leu Leu Pro Lys Asp Ser Glu Ser Gly Asn Asn
        435                 440                 445

Gln Ala Asp Lys Gly Lys Asn Gly Lys Asn Gly Lys Asn Gly Gly Thr
450                 455                 460

Asp Phe Thr Tyr Lys Thr Thr Tyr Thr Pro Lys Ser Asp Glu Lys Asp
465                 470                 475                 480

Thr Gln Ala Gly Thr Pro Thr Asn Gly Ala Gln Thr Ala Ser Asn Thr
                485                 490                 495

Ala Gly Asp Thr Asn Gly Lys Thr Lys Thr Tyr Glu Val Glu Val Cys
            500                 505                 510

Cys Ser Asn Leu Asn Tyr Leu Lys Tyr Gly Met Leu Thr Arg Lys Asn
        515                 520                 525

Ser Lys Ser Ala Met Gln Ala Gly Glu Ser Ser Gln Ala Asp Ala
530                 535                 540

Lys Thr Glu Gln Val Glu Gln Ser Met Phe Leu Gln Gly Glu Arg Thr
545                 550                 555                 560

Asp Glu Lys Glu Ile Pro Lys Glu Gln Asn Val Val Tyr Arg Gly Ser
                565                 570                 575

Trp Tyr Gly His Ile Ala Asn Asp Thr Ser Trp Ser Gly Asn Ala Ser
            580                 585                 590

Asp Lys Glu Gly Gly Asn Arg Ala Glu Phe Thr Val Asp Phe Ala Asp
        595                 600                 605

Lys Lys Ile Thr Gly Lys Leu Thr Ala Glu Asn Arg Gln Ala Gln Thr
610                 615                 620

Phe Thr Ile Glu Gly Met Ile Gln Gly Asn Gly Phe Glu Gly Thr Ala
625                 630                 635                 640

Lys Thr Ala Glu Ser Gly Phe Asp Leu Asp Gln Lys Asn Thr Thr Arg
                645                 650                 655

Thr Pro Lys Ala Tyr Ile Thr Asp Ala Lys Val Lys Gly Gly Phe Tyr
            660                 665                 670

Gly Pro Lys Ala Glu Glu Leu Gly Gly Trp Phe Ala Tyr Pro Gly Asp
        675                 680                 685

Lys Gln Thr Lys Asn Ala Thr Ala Thr Ser Ser Asp Gly Lys Ser Ala
690                 695                 700

Ser Ser Ala Thr Val Val Phe Gly Ala Lys Arg Gln Gln Pro Val Arg
705                 710                 715                 720

<210> SEQ ID NO 28
<211> LENGTH: 972
<212> TYPE: PRT
<213> ORGANISM: Neisseria meningitidis

<400> SEQUENCE: 28

Pro Pro Pro Asn Leu His Thr Gly Asp Phe Thr Asn Pro Asn Asp Ala
1               5                   10                  15

Tyr Lys Asn Leu Ile Asn Leu Lys Pro Ala Ile Glu Ala Gly Tyr Thr
            20                  25                  30
```

-continued

Gly Arg Gly Val Glu Val Gly Ile Val Asp Thr Gly Glu Ser Val Gly
        35                  40                  45

Ser Ile Ser Phe Pro Glu Leu Tyr Gly Arg Lys Glu His Gly Tyr Asn
    50                  55                  60

Glu Asn Tyr Lys Asn Tyr Thr Ala Tyr Met Arg Lys Glu Ala Pro Glu
65                  70                  75                  80

Asp Gly Gly Lys Asp Ile Glu Ala Ser Phe Asp Asp Ala Val
                85                  90                  95

Ile Glu Thr Glu Ala Lys Pro Thr Asp Ile Arg His Val Lys Glu Ile
                100                 105                 110

Gly His Ile Asp Val Val Ser His Ile Ile Gly Gly Arg Ser Val Asp
            115                 120                 125

Gly Arg Pro Ala Gly Gly Ile Ala Pro Asp Ala Thr Leu His Ile Met
        130                 135                 140

Asn Thr His Asp Gly Thr Lys Asn Glu Ile Met Ser Ala Ala Ile Arg
145                 150                 155                 160

Asn Ala Trp Val Lys Leu Gly Glu Arg Gly Val Arg Ile Val Asn Asn
                165                 170                 175

Ser Phe Gly Thr Thr Ser Arg Ala Gly Thr Ala Asp Leu Phe Gln Ile
            180                 185                 190

Ala Asn Ser Glu Glu Gln Tyr Arg Gln Ala Leu Leu Asp Tyr Ser Gly
        195                 200                 205

Gly Asp Lys Thr Asp Glu Gly Ile Arg Leu Met Gln Gln Ser Asp Tyr
    210                 215                 220

Gly Asn Leu Ser Tyr His Ile Arg Asn Lys Asn Met Leu Phe Ile Phe
225                 230                 235                 240

Ser Ala Ser Asn Asp Ala Gln Ala Gln Pro Asn Thr Leu Thr Leu Leu
                245                 250                 255

Pro Phe Tyr Glu Lys Asp Ala Gln Lys Gly Ile Ile Thr Val Ala Gly
            260                 265                 270

Val Asp Arg Ser Gly Glu Lys Phe Asn Gly Ser Asn His Cys Gly Ile
        275                 280                 285

Thr Ala Met Trp Cys Leu Ser Ala Pro Tyr Glu Ala Ser Val Arg Phe
290                 295                 300

Thr Arg Thr Asn Pro Ile Gln Ile Ala Gly Thr Ser Phe Ser Ala Pro
305                 310                 315                 320

Ile Val Thr Gly Thr Ala Ala Leu Leu Leu Gln Lys Tyr Pro Trp Met
                325                 330                 335

Ser Asn Asp Asn Leu Arg Thr Thr Leu Leu Thr Thr Ala Gln Asp Ile
            340                 345                 350

Gly Ala Val Gly Val Asp Ser Lys Phe Gly Trp Gly Leu Leu Asp Ala
        355                 360                 365

Gly Lys Ala Met Asn Gly Pro Ala Ser Phe Pro Phe Gly Asp Phe Thr
    370                 375                 380

Ala Asp Thr Lys Gly Thr Ser Asp Ile Ala Tyr Ser Phe Arg Asn Asp
385                 390                 395                 400

Ile Ser Gly Thr Gly Gly Leu Ile Lys Lys Gly Gly Ser Gln Leu Gln
                405                 410                 415

Leu His Gly Asn Asn Thr Tyr Thr Gly Lys Thr Val Ile Glu Gly Gly
            420                 425                 430

Ser Leu Val Leu Tyr Gly Asn Asn Glu Ser Asp Met Arg Val Glu Thr
        435                 440                 445

-continued

Lys Gly Ala Leu Ile Tyr Asn Gly Ala Ala Ser Gly Ser Leu Asn
450                 455                 460

Ser Asp Gly Ile Val Tyr Leu Ala Asp Thr Asp Arg Ser Gly Ala Asn
465                 470                 475                 480

Glu Thr Val His Ile Lys Gly Asp Leu Gln Leu Gly Gly Glu Gly Thr
                485                 490                 495

Leu Tyr Thr Arg Leu Gly Lys Leu Leu Lys Val Asp Gly Thr Ala Met
                500                 505                 510

Thr Gly Gly Lys Leu Tyr Met Ser Ala Arg Gly Lys Gly Ala Gly Tyr
                515                 520                 525

Leu Asn Arg Thr Gly Gln Arg Val Pro Phe Leu Ser Ala Ala Lys Ile
530                 535                 540

Gly Arg Asp Tyr Ser Phe Phe Thr Asn Ile Glu Thr Asp Gly Gly Leu
545                 550                 555                 560

Leu Ala Ser Leu Asp Ser Val Glu Lys Thr Ala Gly Ser Glu Gly Asp
                565                 570                 575

Thr Leu Ser Tyr Tyr Val Arg Arg Gly Asn Ala Ala Arg Thr Ala Ser
                580                 585                 590

Ala Ala Ala His Ser Ala Pro Ala Gly Leu Lys His Ala Val Glu Gln
                595                 600                 605

Gly Gly Ser Asn Leu Glu Asn Leu Met Val Glu Leu Asp Ala Ser Glu
610                 615                 620

Ser Ser Ala Thr Pro Glu Thr Val Glu Thr Ala Ala Asp Arg Thr
625                 630                 635                 640

Asp Met Pro Gly Ile Arg Pro Tyr Gly Ala Thr Phe Arg Ala Ala Ala
                645                 650                 655

Ala Val Gln His Ala Asn Ala Asp Gly Val Arg Ile Phe Asn Ser
                660                 665                 670

Leu Ala Ala Thr Val Tyr Ala Asp Ser Thr Ala Ala His Ala Asp Met
                675                 680                 685

Gln Gly Arg Arg Leu Lys Ala Val Ser Asp Gly Leu Asp His Asn Ala
690                 695                 700

Thr Gly Leu Arg Val Ile Ala Gln Thr Gln Gln Asp Gly Gly Thr Trp
705                 710                 715                 720

Glu Gln Gly Gly Val Glu Gly Lys Met Arg Gly Ser Thr Gln Thr Val
                725                 730                 735

Gly Ile Ala Ala Lys Thr Gly Glu Asn Thr Ala Ala Thr Leu
                740                 745                 750

Gly Met Gly His Ser Thr Trp Ser Glu Asn Ser Ala Asn Ala Lys Thr
                755                 760                 765

Asp Ser Ile Ser Leu Phe Ala Gly Ile Arg His Asp Ala Gly Asp Ile
770                 775                 780

Gly Tyr Leu Lys Gly Leu Phe Ser Tyr Gly Arg Tyr Lys Asn Ser Ile
785                 790                 795                 800

Ser Arg Ser Thr Gly Ala Asp Glu His Ala Glu Gly Ser Val Asn Gly
                805                 810                 815

Thr Leu Met Gln Leu Gly Ala Leu Gly Gly Val Asn Val Pro Phe Ala
                820                 825                 830

Ala Thr Gly Asp Leu Thr Val Glu Gly Gly Leu Arg Tyr Asp Leu Leu
                835                 840                 845

Lys Gln Asp Ala Phe Ala Glu Lys Gly Ser Ala Leu Gly Trp Ser Gly
850                 855                 860

Asn Ser Leu Thr Glu Gly Thr Leu Val Gly Leu Ala Gly Leu Lys Leu

```
                     865                 870                 875                 880
Ser Gln Pro Leu Ser Asp Lys Ala Val Leu Phe Ala Thr Ala Gly Val
                885                 890                 895

Glu Arg Asp Leu Asn Gly Arg Asp Tyr Thr Val Thr Gly Gly Phe Thr
                900                 905                 910

Gly Ala Thr Ala Ala Gly Lys Thr Gly Ala Arg Asn Met Pro His
                915                 920                 925

Thr Arg Leu Val Ala Gly Leu Gly Ala Asp Val Glu Phe Gly Asn Gly
                930                 935                 940

Trp Asn Gly Leu Ala Arg Tyr Ser Tyr Ala Gly Ser Lys Gln Tyr Gly
945                 950                 955                 960

Asn His Ser Gly Arg Val Gly Val Gly Tyr Arg Phe
                965                 970
```

<210> SEQ ID NO 29
<211> LENGTH: 52
<212> TYPE: PRT
<213> ORGANISM: Neisseria meningitidis

<400> SEQUENCE: 29

```
Phe Thr Leu Ile Glu Leu Met Ile Val Ile Ala Ile Val Gly Ile Leu
1               5                   10                  15

Ala Ala Val Ala Leu Pro Ala Tyr Gln Asp Tyr Thr Ala Arg Ala Gln
                20                  25                  30

Val Ser Glu Ala Ile Leu Leu Ala Glu Gly Gln Lys Ser Ala Val Thr
            35                  40                  45

Glu Tyr Tyr Leu
            50
```

<210> SEQ ID NO 30
<211> LENGTH: 53
<212> TYPE: PRT
<213> ORGANISM: Neisseria meningitidis

<400> SEQUENCE: 30

```
Phe Thr Leu Leu Glu Leu Met Ile Ala Val Ala Ile Leu Gly Ile Leu
1               5                   10                  15

Thr Leu Ile Thr Tyr Pro Ser Tyr Lys Thr Tyr Ile Arg Arg Val Arg
                20                  25                  30

Leu Ser Glu Val Arg Thr Thr Leu Leu His Asn Ala Gln Thr Met Glu
            35                  40                  45

Arg Tyr Tyr Arg Gln
            50
```

<210> SEQ ID NO 31
<211> LENGTH: 117
<212> TYPE: PRT
<213> ORGANISM: Neisseria meningitidis

<400> SEQUENCE: 31

```
Ser Ala Val Thr Glu Tyr Tyr Leu Asn His Gly Glu Trp Pro Gly Asp
1               5                   10                  15

Asn Ser Ser Ala Gly Val Ala Thr Ser Ala Asp Ile Lys Gly Lys Tyr
                20                  25                  30

Val Gln Ser Val Thr Val Ala Asn Gly Val Ile Thr Ala Gln Met Ala
            35                  40                  45

Ser Ser Asn Val Asn Asn Glu Ile Lys Ser Lys Lys Leu Ser Leu Trp
        50                  55                  60
```

Ala Lys Arg Gln Asn Gly Ser Val Lys Trp Phe Cys Gly Gln Pro Val
 65                  70                  75                  80

Thr Arg Thr Thr Ala Thr Ala Thr Asp Val Ala Ala Asn Gly Lys
                 85                  90                  95

Thr Asp Asp Lys Ile Asn Thr Lys His Leu Pro Ser Thr Cys Arg Asp
            100                 105                 110

Asp Ser Ser Ala Ser
        115

<210> SEQ ID NO 32
<211> LENGTH: 76
<212> TYPE: PRT
<213> ORGANISM: Neisseria meningitidis

<400> SEQUENCE: 32

Thr Met Glu Arg Tyr Tyr Arg Gln Lys Gly Thr Phe Lys Thr Tyr Asp
 1               5                  10                  15

Lys Asn Lys Leu Lys Gln Asn Lys Tyr Phe Asn Val Thr Leu Ser Lys
                20                  25                  30

Val Ser Pro Asp His Phe Thr Leu Gln Ala Asp Pro Asn Pro Thr Thr
            35                  40                  45

Asn Asp Gly Glu Thr Cys Val Val Thr Leu Asp Gly Gly Thr Ile Ala
 50                  55                  60

Ala Ser Gly Thr Asn Gln Ser Cys Pro Gly Phe Asp
 65                  70                  75

<210> SEQ ID NO 33
<211> LENGTH: 35
<212> TYPE: PRT
<213> ORGANISM: Neisseria meningitidis

<400> SEQUENCE: 33

Cys Gly Gln Pro Val Thr Arg Thr Thr Ala Thr Ala Thr Asp Val Ala
 1               5                  10                  15

Ala Ala Asn Gly Lys Thr Asp Asp Lys Ile Asn Thr Lys His Leu Pro
                20                  25                  30

Ser Thr Cys
        35

<210> SEQ ID NO 34
<211> LENGTH: 27
<212> TYPE: PRT
<213> ORGANISM: Neisseria meningitidis

<400> SEQUENCE: 34

Gly Glu Thr Cys Val Val Thr Leu Asn Asp Gly Gly Thr Ile Ala Ala
 1               5                  10                  15

Ser Gly Thr Asn Gln Ser Cys Pro Gly Phe Asp
                20                  25

<210> SEQ ID NO 35
<211> LENGTH: 396
<212> TYPE: PRT
<213> ORGANISM: Artificial Sequence
<220> FEATURE:
<223> OTHER INFORMATION: Fusion protein PilE-fHBP

<400> SEQUENCE: 35

Ser Ala Val Thr Glu Tyr Tyr Leu Asn His Gly Glu Trp Pro Gly Asp
 1               5                  10                  15

```
Asn Ser Ser Ala Gly Val Ala Thr Ser Ala Asp Ile Lys Gly Lys Tyr
            20                  25                  30

Val Gln Ser Val Thr Val Ala Asn Gly Val Ile Thr Ala Gln Met Ala
        35                  40                  45

Ser Ser Asn Val Asn Asn Glu Ile Lys Ser Lys Lys Leu Ser Leu Trp
50                  55                  60

Ala Lys Arg Gln Asn Gly Ser Val Lys Trp Phe Cys Gly Gln Pro Val
65                  70                  75                  80

Thr Arg Thr Thr Ala Thr Ala Thr Asp Val Ala Ala Asn Gly Lys
                85                  90                  95

Thr Asp Asp Lys Ile Asn Thr Lys His Leu Pro Ser Thr Cys Arg Asp
            100                 105                 110

Asp Ser Ser Ala Ser Met Thr Arg Ser Lys Pro Val Asn Arg Thr Ala
        115                 120                 125

Phe Cys Cys Leu Ser Leu Thr Ala Ala Leu Ile Leu Thr Ala Cys Ser
130                 135                 140

Ser Gly Gly Gly Val Ala Ala Asp Ile Gly Ala Gly Leu Ala Asp
145                 150                 155                 160

Ala Leu Thr Ala Pro Leu Asp His Lys Asp Lys Ser Leu Gln Ser Leu
                165                 170                 175

Thr Leu Asp Gln Ser Val Arg Lys Asn Glu Lys Leu Lys Leu Ala Ala
            180                 185                 190

Gln Gly Ala Glu Lys Thr Tyr Gly Asn Gly Asp Ser Leu Asn Thr Gly
        195                 200                 205

Lys Leu Lys Asn Asp Lys Val Ser Arg Phe Asp Phe Ile Arg Gln Ile
210                 215                 220

Glu Val Asp Gly Gln Leu Ile Thr Leu Glu Ser Gly Glu Phe Gln Ile
225                 230                 235                 240

Tyr Lys Gln Asp His Ser Ala Val Val Ala Leu Gln Ile Glu Lys Ile
                245                 250                 255

Asn Asn Pro Asp Lys Ile Asp Ser Leu Ile Asn Gln Arg Ser Phe Leu
            260                 265                 270

Val Ser Gly Leu Gly Gly Glu His Thr Ala Phe Asn Gln Leu Pro Gly
        275                 280                 285

Gly Lys Ala Glu Tyr His Gly Lys Ala Phe Ser Ser Asp Asp Ala Gly
290                 295                 300

Gly Lys Leu Thr Tyr Thr Ile Asp Phe Ala Ala Lys Gln Gly His Gly
305                 310                 315                 320

Lys Ile Glu His Leu Lys Thr Pro Glu Gln Asn Val Glu Leu Ala Ala
                325                 330                 335

Ala Glu Leu Lys Ala Asp Glu Lys Ser His Ala Val Ile Leu Gly Asp
            340                 345                 350

Thr Arg Tyr Gly Ser Glu Glu Lys Gly Thr Tyr His Leu Ala Leu Phe
        355                 360                 365

Gly Asp Arg Ala Gln Glu Ile Ala Gly Ser Ala Thr Val Lys Ile Gly
370                 375                 380

Glu Lys Val His Glu Ile Gly Ile Ala Gly Lys Gln
385                 390                 395

<210> SEQ ID NO 36
<211> LENGTH: 314
<212> TYPE: PRT
<213> ORGANISM: Artificial Sequence
<220> FEATURE:
```

<223> OTHER INFORMATION: Fusion protein PilE-fHBP

<400> SEQUENCE: 36

| | | | | | | | | | | | | | | |

```
Val Ser Pro Asp His Phe Thr Leu Gln Ala Asp Pro Asn Pro Thr Thr
     35                  40                  45

Asn Asp Gly Glu Thr Cys Val Val Thr Leu Asp Gly Gly Thr Ile Ala
 50                  55                  60

Ala Ser Gly Thr Asn Gln Ser Cys Pro Gly Phe Asp Met Thr Arg Ser
 65                  70                  75                  80

Lys Pro Val Asn Arg Thr Ala Phe Cys Cys Leu Ser Leu Thr Ala Ala
                 85                  90                  95

Leu Ile Leu Thr Ala Cys Ser Ser Gly Gly Gly Val Ala Ala Asp
             100                 105                 110

Ile Gly Ala Gly Leu Ala Asp Ala Leu Thr Ala Pro Leu Asp His Lys
         115                 120                 125

Asp Lys Ser Leu Gln Ser Leu Thr Leu Asp Gln Ser Val Arg Lys Asn
130                 135                 140

Glu Lys Leu Lys Leu Ala Ala Gln Gly Ala Glu Lys Thr Tyr Gly Asn
145                 150                 155                 160

Gly Asp Ser Leu Asn Thr Gly Lys Leu Lys Asn Asp Lys Val Ser Arg
                165                 170                 175

Phe Asp Phe Ile Arg Gln Ile Glu Val Asp Gly Gln Leu Ile Thr Leu
             180                 185                 190

Glu Ser Gly Glu Phe Gln Ile Tyr Lys Gln Asp His Ser Ala Val Val
         195                 200                 205

Ala Leu Gln Ile Glu Lys Ile Asn Asn Pro Asp Lys Ile Asp Ser Leu
     210                 215                 220

Ile Asn Gln Arg Ser Phe Leu Val Ser Gly Leu Gly Gly Glu His Thr
225                 230                 235                 240

Ala Phe Asn Gln Leu Pro Gly Gly Lys Ala Glu Tyr His Gly Lys Ala
                245                 250                 255

Phe Ser Ser Asp Asp Ala Gly Gly Lys Leu Thr Tyr Thr Ile Asp Phe
             260                 265                 270

Ala Ala Lys Gln Gly His Gly Lys Ile Glu His Leu Lys Thr Pro Glu
         275                 280                 285

Gln Asn Val Glu Leu Ala Ala Ala Glu Leu Lys Ala Asp Glu Lys Ser
     290                 295                 300

His Ala Val Ile Leu Gly Asp Thr Arg Tyr Gly Ser Glu Glu Lys Gly
305                 310                 315                 320

Thr Tyr His Leu Ala Leu Phe Gly Asp Arg Ala Gln Glu Ile Ala Gly
                325                 330                 335

Ser Ala Thr Val Lys Ile Gly Glu Lys Val His Glu Ile Gly Ile Ala
             340                 345                 350

Gly Lys Gln
        355

<210> SEQ ID NO 38
<211> LENGTH: 306
<212> TYPE: PRT
<213> ORGANISM: Artificial Sequence
<220> FEATURE:
<223> OTHER INFORMATION: Fusion protein PilV-fHBP

<400> SEQUENCE: 38

Gly Glu Thr Cys Val Val Thr Leu Asn Asp Gly Gly Thr Ile Ala Ala
 1               5                  10                  15

Ser Gly Thr Asn Gln Ser Cys Pro Gly Phe Asp Met Thr Arg Ser Lys
                 20                  25                  30
```

Pro Val Asn Arg Thr Ala Phe Cys Cys Leu Ser Leu Thr Ala Ala Leu
         35                  40                  45

Ile Leu Thr Ala Cys Ser Ser Gly Gly Gly Val Ala Ala Asp Ile
 50                  55                  60

Gly Ala Gly Leu Ala Asp Ala Leu Thr Ala Pro Leu Asp His Lys Asp
 65                  70                  75                  80

Lys Ser Leu Gln Ser Leu Thr Leu Asp Gln Ser Val Arg Lys Asn Glu
             85                  90                  95

Lys Leu Lys Leu Ala Ala Gln Gly Ala Glu Lys Thr Tyr Gly Asn Gly
            100                 105                 110

Asp Ser Leu Asn Thr Gly Lys Leu Lys Asn Asp Lys Val Ser Arg Phe
            115                 120                 125

Asp Phe Ile Arg Gln Ile Glu Val Asp Gly Gln Leu Ile Thr Leu Glu
            130                 135                 140

Ser Gly Glu Phe Gln Ile Tyr Lys Gln Asp His Ser Ala Val Val Ala
145                 150                 155                 160

Leu Gln Ile Glu Lys Ile Asn Asn Pro Asp Lys Ile Asp Ser Leu Ile
                165                 170                 175

Asn Gln Arg Ser Phe Leu Val Ser Gly Leu Gly Gly Glu His Thr Ala
            180                 185                 190

Phe Asn Gln Leu Pro Gly Gly Lys Ala Glu Tyr His Gly Lys Ala Phe
            195                 200                 205

Ser Ser Asp Asp Ala Gly Gly Lys Leu Thr Tyr Thr Ile Asp Phe Ala
210                 215                 220

Ala Lys Gln Gly His Gly Lys Ile Glu His Leu Lys Thr Pro Glu Gln
225                 230                 235                 240

Asn Val Glu Leu Ala Ala Ala Glu Leu Lys Ala Asp Glu Lys Ser His
                245                 250                 255

Ala Val Ile Leu Gly Asp Thr Arg Tyr Gly Ser Glu Glu Lys Gly Thr
            260                 265                 270

Tyr His Leu Ala Leu Phe Gly Asp Arg Ala Gln Glu Ile Ala Gly Ser
            275                 280                 285

Ala Thr Val Lys Ile Gly Glu Lys Val His Glu Ile Gly Ile Ala Gly
            290                 295                 300

Lys Gln
305

<210> SEQ ID NO 39
<211> LENGTH: 18
<212> TYPE: RNA
<213> ORGANISM: Artificial Sequence
<220> FEATURE:
<223> OTHER INFORMATION: Control siRNA

<400> SEQUENCE: 39
auguauuggc cuguauag                                                    18

The invention claimed is:

1. A method for treating a meningococcal bacteremia and/or infection in an individual in need thereof, comprising administering a therapeutically effective amount of an antibody that specifically binds to a type IV pilus-associated protein consisting of SEQ ID NO: 32 or SEQ ID NO: 34 or a fragment thereof, wherein said antibody is in a pharmaceutically acceptable carrier.

2. The method according to claim 1, further comprising administering at least one anti-bacterial compound, either sequentially or simultaneously.

3. The method according to claim 2, wherein said anti-bacterial compound comprises or consists of a meningococcal PilE, PilV, PilX, PilC, ComP, fHbp, PorA, NHBA, NadA, MafA, NspA, HmbR, TbpB, AusP, or a fragment thereof.

4. The method according to claim 1, wherein the type IV pilus-associated protein consisting of a) of SEQ ID NO: 32, or b) a fragment consisting of at least 10, 15, 20, 25, 30, 35, 40, 45, 50, 55, 60, 65, 70 or 75 consecutive amino acids of the sequence SEQ ID NO: 32.

5. The method according to claim 1, wherein the type IV pilus-associated protein consisting of a) SEQ ID NO: 34, or b) a fragment consisting of at least 10, 15, 20, or 25 consecutive amino acids of the sequence SEQ ID NO: 34.

* * * * *

UNITED STATES PATENT AND TRADEMARK OFFICE
CERTIFICATE OF CORRECTION

PATENT NO. : 10,000,545 B2
APPLICATION NO. : 14/405444
DATED : June 19, 2018
INVENTOR(S) : Nassif et al.

Page 1 of 2

It is certified that error appears in the above-identified patent and that said Letters Patent is hereby corrected as shown below:

In the Specification

Column 16, Lines 20-23:
Please change:
"a) the sequence TMERYYRQKGTFKTYD-KNKLKQNKYFNVTLSKVSPDHFTLQADP-NPTTNDGETCVVTLDGGTIAASGTNQSCPGFD (SEQ ID NO :32), or"

To:
--a) the sequence TMERYYRQKGTFKTYDKNKLKQNKYFNVTLSKVSPDHFTLQADPNPTTNDGETCVVTLNDGGTIAASGTNQSCPGFD (SEQ ID NO :32), or--

Column 83:
Please change:

```
<210>  SEQ ID NO 32
<211>  LENGTH: 76
<212>  TYPE: PRT
<213>  ORGANISM: Neisseria meningitidis

<400>  SEQUENCE: 32

Thr Met Glu Arg Tyr Tyr Arg Gln Lys Gly Thr Phe Lys Thr Tyr Asp
 1               5                  10                  15

Lys Asn Lys Leu Lys Gln Asn Lys Tyr Phe Asn Val Thr Leu Ser Lys
             20                  25                  30

Val Ser Pro Asp His Phe Thr Leu Gln Ala Asp Pro Asn Pro Thr Thr
         35                  40                  45

Asn Asp Gly Glu Thr Cys Val Val Thr Leu Asp Gly Gly Thr Ile Ala
     50                  55                  60

Ala Ser Gly Thr Asn Gln Ser Cys Pro Gly Phe Asp
 65                  70                  75
```
" "

Signed and Sealed this
Fifteenth Day of October, 2019

Andrei Iancu
*Director of the United States Patent and Trademark Office*

CERTIFICATE OF CORRECTION (continued)
U.S. Pat. No. 10,000,545 B2

To:

```
<210> SEQ ID NO 32
<211> LENGTH: 77
<212> TYPE: PRT
<213> ORGANISM: Neisseria meningitidis

<400> SEQUENCE: 32

Thr Met Glu Arg Tyr Tyr Arg Gln Lys Gly Thr Phe Lys Thr Tyr Asp
1               5                   10                  15

Lys Asn Lys Leu Lys Gln Asn Lys Tyr Phe Asn Val Thr Leu Ser Lys
                20                  25                  30

Val Ser Pro Asp His Phe Thr Leu Gln Ala Asp Pro Asn Pro Thr Thr
            35                  40                  45

Asn Asp Gly Glu Thr Cys Val Val Thr Leu Asn Asp Gly Gly Thr Ile
    50                  55                  60

Ala Ala Ser Gly Thr Asn Gln Ser Cys Pro Gly Phe Asp
65                  70                  75
```
--